(12) United States Patent
Buller et al.

(10) Patent No.: US 11,879,143 B2
(45) Date of Patent: *Jan. 23, 2024

(54) ENGINEERED BETA-SUBUNIT OF TRYPTOPHAN SYNTHASE FOR PRODUCTION OF NON-CANONICAL AMINO ACIDS

(71) Applicant: California Institute of Technology, Pasadena, CA (US)

(72) Inventors: Andrew Richard Buller, Pasadena, CA (US); Sabine Brinkmann-Chen, Alhambra, CA (US); Michael Herger, Pasadena, CA (US); David K. Romney, Pasadena, CA (US); Javier Murciano Calles, Jaen (ES); Paul van Roye, Darmstadt (DE)

(73) Assignee: California Institute of Technology, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/691,452

(22) Filed: Nov. 21, 2019

(65) Prior Publication Data

US 2020/0149078 A1   May 14, 2020

Related U.S. Application Data

(63) Continuation of application No. 15/094,458, filed on Apr. 8, 2016, now Pat. No. 10,513,719.

(60) Provisional application No. 62/236,030, filed on Oct. 1, 2015, provisional application No. 62/144,783, filed on Apr. 8, 2015.

(51) Int. Cl.
*C12P 13/22* (2006.01)
*C12N 9/88* (2006.01)
*C12P 13/04* (2006.01)

(52) U.S. Cl.
CPC ............. *C12P 13/227* (2013.01); *C12N 9/88* (2013.01); *C12P 13/04* (2013.01); *C12Y 402/0102* (2013.01)

(58) Field of Classification Search
None
See application file for complete search history.

(56) References Cited

U.S. PATENT DOCUMENTS

| | | | |
|---|---|---|---|
| 5,374,543 | A | 12/1994 | Murdock |
| 6,441,274 | B1 | 8/2002 | Cahoon et al. |
| 10,513,719 | B2 | 12/2019 | Buller et al. |
| 2016/0298152 | A1* | 10/2016 | Buller .................. C12P 13/227 |
| 2018/0057806 | A1 | 3/2018 | Romney et al. |
| 2018/0327793 | A1 | 11/2018 | Boville et al. |

FOREIGN PATENT DOCUMENTS

WO    9534657 A2    12/1995

OTHER PUBLICATIONS

Uniprot, Accession No. O28672, 2014, www.uniprot.org (Year: 2014).*
Dunn, Allosteric regulation of substrate channeling and catalysis in the tryptophan synthase bienzyme complex, Archives Biochem. Biophys. 519, 2012, 154-66. (Year: 2012).*
Lane et al., The catalytic mechanism of tryptophan synthase in *Escherichia coli*, Eur. J. Biochem. 129, 1983, 571. (Year: 1983).*
Lee et al., Conformational Changes in the Tryptophan Synthase from a Hyperthermophile upon alpha2beta2 Complex Formation, Biochemistry 44, 2005, 11417-27. (Year: 2005).*
Schneider et al., Loop Closure and Intersubunit Communication in Tryptophan Synthase, Biochemistry 37, 1998, 5394-5406. (Year: 1998).*
Rhee et al., Exchange of K+ or Cs+ for Na+ Induces Local and Long-Range Changes in the Three-Dimensional Structure of the Tryptophan Synthase α2β2 Complex, Biochemistry 35, 1996, 4211-21. (Year: 1996).*
Uniprot, Accession No. P0A2K1, 2016, www.uniprot.org. (Year: 2016).*
Buller et al. (Directed evolution of the tryptophan synthase β-subunit for stand-alone function recapitulates allosteric activation, Proc. Natl. Acad. Sci. USA 112, Nov. 2015, 14599-604 and Supplemental Information. (Year: 2015).*
Uniprot Q8U093, 2015, www.uniprot.org. (Year: 2015).*
Herger et al., Synthesis of beta-Branched Tryptophan Analogues Using an Engineered Subunit of Tryptophan Synthase, J. Am. Chem. Soc. 138, Jun. 2016, 8388-91. (Year: 2016).*
Uniprot, Accession No. Q9YGB0, 2014, www.uniprot.org. (Year: 2014).*
Ahmed et al., "Aliphatic Alcohols Stabilize an Alternative Conformation of the Tryptophan Synthase α2β2 Complex from *Salmonella typhimurium*", Journal of Biological Chemistry, vol. 269, No. 23, Jun. 10, 1994, pp. 16486-16492.
Brzovic et al., "Substitution of Glutamic Acid 109 by Aspartic Acid Alters the Substrate Specificity and Catalytic Activity of the Beta-Subunit in the Tryptophan Synthase Bienzyme Complex from *Salmonella typhimurium*", Biochemistry, vol. 31, No. 4, Feb. 4, 1992, pp. 1180-1190.
Buller et al., "Directed Evolution of The Tryptophan Synthase β-Subunit For Stand-Alone Function Recapitulates Allosteric Activation", Proceedings of the National Academy of Sciences of the United States of America; vol. 112, No. 47, Apr. 30, 2019, pp. 14599-14604.
Evran et al., "Directed Evolution of (βα)(8)-Barrel Enzymes: Establishing Phosphoribosylanthranilate Isomerisation Activity on the Scaffold of the Tryptophan Synthase α-Subunit", Protein Engineering, Design & Selection, vol. 25, No. 6, Jun. 25, 2012, pp. 285-293.

(Continued)

*Primary Examiner* — Todd M Epstein
(74) *Attorney, Agent, or Firm* — Kilpatrick Townsend & Stockton LLP

(57) ABSTRACT

This disclosure relates to modified tryptophan synthase and more particularly to modified beta-subunits of tryptophan synthase. The disclosure further relates to cells expressing such modified subunits and methods of producing non-canonical amino acids.

16 Claims, 13 Drawing Sheets

Specification includes a Sequence Listing.

(56) References Cited

OTHER PUBLICATIONS

Ferrari et al., "βD305A Mutant of Tryptophan Synthase Shows Strongly Perturbed Allosteric Regulation and Substrate Specificity", Biochemistry, vol. 40, No. 25, Jun. 1, 2001, pp. 7421-7432.
Goss et al., "A Convenient Enzymatic Synthesis of L-Halotryptophans", Chemical Communications, vol. 47, Oct. 5, 2006, pp. 4924-4925.
Guo et al., "Protein Tolerance to Random Amino Acid Change", Proceedings of the National Academy of Sciences, vol. 101, No. 25, Jun. 22, 2004, pp. 9205-9210.
Phillips, "Synthetic Applications of Tryptophan Synthase", Tetrahedron Asymmetry, vol. 15, No. 18, Sep. 20, 2004, pp. 2787-2792.
Rowlett et al., "Mutations in the Contact Region Between the α and β Subunits of Tryptophan Synthase Alter Subunit Interaction and Intersubunit Communication", Biochemistry, vol. 37, No. 9, Feb. 13, 1998, pp. 2961-2968.
Smith et al., "The First One-Pot Synthesis of L-7-Iodotryptophan from 7-Iodoindole and Serine, and an Improved Synthesis of Other L-7-Halotryptophans", Org. Lett., vol. 16, No. 10, May 7, 2014, pp. 2622-2625.
"Uniprot Accession No. A0A2H0HIJ2", Available Online at: www.uniprot.org, 2018.
"Uniprot Accession No. A9AAU5", Available Online at: https://www.uniprot.org/uniprot/A9AAU5, 2008.
Aljamali et al., "Review Paper in Heterocyclic Compounds", J. Plastic and Polymer, vol. 1, 2015, pp. 49-64.
Anderson et al., "Serine Modulates Substrate Channeling in Tryptophan Synthase", J. Biol. Chem., vol. 266, No. 13, May 5, 1991, pp. 8020-8033.
Ishida et al., "Overexpression in *Escherichia coli* of the AT-rich trpA and trpB Genes From the Hyperthermophilic Archaeon Pyrococcus Furiosus", FEMS Microbiol. Lett., vol. 216, No. 2, Nov. 5, 2002, pp. 179-183.
Metzler, David E., "Equilibria Between Pyridoxal and Amino Acids and their Imines," J. Am. Chem. Soc., vol. 79, No. 2, Jan. 20, 1957, pp. 485-490.
Drewe, William Frederick, Jr., et al., "Detection and Identification of Intermediates in the Reaction of L-Serine with *Escherichia coli* Tryptophan Synthase via Rapid-Scanning Ultraviolet-Visible Spectroscopy," *Biochemistry*, vol. 24, No. 15, Jul. 16, 1985, pp. 3977-3987.
Hur, Oscar et al., "Proton Transfers in the β-Reaction Catalyzed by Tryptophan Synthase," *Biochemistry*, vol. 41, No. 31, Aug. 6, 2002, pp. 9991-10001.

\* cited by examiner

```
OB2 MUTATIONS                                                                                                  L            G
Pyrococcus furiosus    ----------------MWFGEFGGQYVPETLIEPLKELEKAYKRFKDDEEFNRQLNYYLKTWA  47
Archaeoglobus fulgidus MRCWLENLSGGRKMKFGEFGGRFVPEVLIPPLEELEKAYDRFKDDEEFKARLEYYLKSYA  60
Thermotoga maritima    ----------------MKGYFGPYGGQYVPEILMPALEELEAAYEEIMKDESFWKEFNDLLRDYA  49
Escherichia coli       ------------MTTLLNPYFGEFGGMYVPQILMPALRQLEEAFVSAQKDPEFQAQFNDLLKNYA  53
                                        ** .* :**  :**.:*  *  *.: *.  .: :*  .:  : .*

OB2 MUTATIONS                                  V
Pyrococcus furiosus    GRPTPLYYAKRLTEKIGGAKIYLKREDLVHGGAHKTNNAIGQALLAKFMGKTRLIAETGA  107
Archaeoglobus fulgidus GRPTPLYFAENLSREL-GVKIYLKREDLLHGGAHKINNTIGQALLAKFMGKKRVIAETGA  119
Thermotoga maritima    GRPTPLYFARRLSEKY-GARIYLKREDLLHTGAHKINNAIGQVLLAKKMGKTRIIAETGA  108
Escherichia coli       GRPTALFKCQNITAGT-NTTLYLKREDLLHGGAHKTNQVLGQALLAKRMGKTEIIAETGA  112
                       ****  :  ...: :   ::*******:* *****.*  ** :****.:***. :*******

OB2 MUTATIONS
Pyrococcus furiosus    GQHGVATAMAGALLGMKVDIYMGAEDVERQKMNVFRMKLLGANVIPVNSGSRTLKDAINE  167
Archaeoglobus fulgidus GQHGVATAMAAALLGLEAEIYMGAEDYERQKMNVFRMELLGAKVTAVESGSRTLKDAINE  179
Thermotoga maritima    GQHGVATATAAALFGMECVIYMGEEDTIRQKPNVERMKLLGAKVPVKSGSRTLKDAINE  168
Escherichia coli       GQHGVASALASALLGLKCRIYMGAKDVERQSPNVFRMRLMGAEVIPVHSGSATLKDACNE  172
                       ****** :   :**:   ::***. *  :**  **.** *:.*  * :**:****:  **

OB2 MUTATIONS
Pyrococcus furiosus    ALRDWVATFEYTHYLIGSVVGPHPYPTIVRDFQSVIGREAKAQILEAEGQLPDVIVACVG  227
Archaeoglobus fulgidus ALRDWVESFEHTHYLIGSVVGPHPFPTIVRDFQAVIGKEARRQIIEAEGGMPDAIIACVG  239
Thermotoga maritima    ALRDWITNLQTTYYVIGSVVGPHPYPIIVRNFQKVIGEETKKQILEKEGRLPDYIVACVG  228
Escherichia coli       ALRDWSGSYETAHYMLGTAAGPHPYPTIVREFQRMIGEETKAQILEREGRLPDAVIACVG  232
                       *****    :  :*::* :.*.***:* :**.**: :**  :   :**: **  *::*

OB2 MUTATIONS                                                          S
Pyrococcus furiosus    GGSNAMGIFYPFVNDKKVKLVGVEAGGKGLESGKHSASLNAGQVGVFHGMLSYFLQDEEG  287
Archaeoglobus fulgidus GGSNAMGIFHPFLND-DVRLIGVEAGGEIESGRHSASLTAGSKGVLHGMLSYFLQDEEG  298
Thermotoga maritima    GGSNAAGIFYPFIDS-GVKLIGVEAGGEGLETGKHAASLLKGKIGYLHGSKTEVLQDDWG  287
Escherichia coli       GGSNAIGMFADFINETNVGLIGVEPGGHGIETGEHGAPLKHGRVGIYFGMKAPMMQTEDG  292
                       ***** *:* :*::   * :***: * .:*:*:*.: *   :  : .*       ::*
```

FIG. 2

| OB2 MUTATIONS | | |
|---|---|---|
| |                                       S                                                              A | |
| *Pyrococcus furiosus* | QIKPTHSIAPGLDYPGVGPEHAYLKKIQRAEYTVTDEEALKAFHELSRTEGIIPALESA | 347 |
| *Archaeoglobus fulgidus* | MMLDTHSVSAGLDYPGVGPEHAYLKETGRCEYTVNDEEALRAFKTLSKLEGIIPALESA | 358 |
| *Thermotoga maritima* | QVQVTHSVSAGLDYSGVGPEHAYWRETGKVLYDAVTDEEALDAFIELSRLEGIIPALESS | 347 |
| *Escherichia coli* | QIEESYSISAGLDFPSVGPQHAYLNSTGRADYVSITDDEALEAFKTLCLHEGIIPALESS | 352 |
| | : ::*:: *:. . :  * :::.:  **********: | |

| OB2 MUTATIONS | | |
|---|---|---|
| *Pyrococcus furiosus* | HAVAYAMKLAKE-MSRDEIIVNLSGRGDKLDIVLKVSGNV----- | 388 |
| *Archaeoglobus fulgidus* | HAIAYAMKMAEE-MQRDDVLVVNLSGRGDKDMDIVRRRLA----- | 397 |
| *Thermotoga maritima* | HALAYLKKIN----IKGKVVVVNLSGRGDKDLESVLNHPYVRERIR | 389 |
| *Escherichia coli* | HALAHALKMMRENPDKEQLLVVNLSGRGDKDIFTVHDILKARGEI- | 397 |
| | *:  :         . .:::*********:     *    | |

FIG. 2 (continued)

ENGINEERED BETA-SUBUNIT OF TRYPTOPHAN SYNTHASE FOR PRODUCTION OF NON-CANONICAL AMINO ACIDS

CROSS REFERENCE TO RELATED APPLICATIONS

This application is a continuation of U.S. patent application Ser. No. 15/094,458, filed Apr. 8, 2016, which claims priority under 35 U.S.C. 119 to U.S. Provisional Application Ser. No. 62/144,783, filed Apr. 8, 2015, and U.S. Provisional Application No. 62/236,030, filed Oct. 1, 2015, the disclosures of which are incorporated herein by reference.

STATEMENT REGARDING FEDERALLY SPONSORED RESEARCH

This invention was made with government support under Grant No. GM110851 awarded by the National Institutes of Health. The government has certain rights in the invention.

INCORPORATION BY REFERENCE OF SEQUENCE LISTING

Accompanying this filing is a Sequence Listing entitled "sequence_ST25.txt", created on Apr. 8, 2016 and having 186 kB of data, machine formatted on IBM-PC, MS-Windows operating system. The sequence listing is hereby incorporated by reference in its entirety for all purposes.

TECHNICAL FIELD

This invention relates to modified tryptophan synthase and more particularly to modified beta-subunits of tryptophan synthase. The invention further relates to cells expressing such modified subunits and methods of producing non-canonical amino acids.

BACKGROUND

Heteromeric enzyme complexes catalyzing a rich array of useful reactions are often allosterically regulated by their protein partners, such that the catalytic subunits are much less active when isolated. Utilizing isolated enzyme subunits, however, is desirable for biosynthetic applications, wherein expressing large complexes increases the metabolic load on the host cell and complicates efforts to engineer activity, substrate specificity, stability, and other properties.

Tryptophan synthase (TrpS; EC 4.2.1.20) is a heterodimeric complex that catalyzes the formation of L-tryptophan (Trp) from L-serine (Ser) and indole glycerol phosphate (IGP) (see, FIG. 1A). The mechanism of this transformation has been extensively studied for TrpS from *Escherichia coli* and *Salmonella typhimurium*, where it has been shown the enzyme consists of two subunits, TrpA (α-subunit) and TrpB ((β-subunit), both of which have low catalytic efficiencies in isolation. The activities of both subunits increase upon complex formation and are further regulated by an intricate and well-studied allosteric mechanism. IGP binding to the α-subunit stimulates pyridoxal phosphate (PLP)-dependent aminoacrylate formation in the β-subunit [E(A-A); FIG. 1B], which in turn promotes retro-aldol cleavage of IGP in the α-subunit, releasing indole. This tightly choreographed mechanism serves to prevent the free diffusion of indole, which is only released from the α-subunit when the complex is in a closed conformation that forms a 25-Å tunnel through which indole diffuses into the β-subunit. Here, indole reacts with E(A-A) in a C—C bond-forming reaction, yielding L-tryptophan as product (FIG. 1B). These allosteric effects are mediated through the rigid-body motion of the communication (COMM) domain and a monovalent cation (MVC) binding site within the β-subunit (FIG. 1A), which undergo complex conformational transitions associated with open, partially closed, and fully closed states during the catalytic cycle.

SUMMARY

The disclosure provides a recombinant polypeptide selected from the group consisting of: (a) a polypeptide comprising a sequence that is at least 57% identical to SEQ ID NO:2 and comprises an activating mutation at residues corresponding to residue 144 and 166 of SEQ ID NO:2, wherein the polypeptide can catalyze the production of tryptophan or a non-canonical amino acid or unnatural amino acid from an indole or indole derivative and L-serine or L-threonine independent of any other tryptophan synthase subunit; (b) a polypeptide comprising a sequence that is at least 60% identical to SEQ ID NO:2 and having at least one activating mutation including a mutation corresponding to residue 292, wherein the polypeptide can catalyze the production of tryptophan or a non-canonical amino acid or unnatural amino acid from an indole or indole derivative and L-serine or L-threonine independent of any other tryptophan synthase subunit. In one embodiment, the mutation corresponding to residue 292 is a T-S mutation. In yet another embodiment, the polypeptide that is at least 60% identical to SEQ ID NO:2 comprises a polypeptide that has a sequence of SEQ ID NO:4 or 6, and wherein SEQ ID NO:4 has a mutation at position 303 and wherein SEQ ID NO:6 has a mutation at position 292. In a further embodiment, the mutations at 303 and 292 are I303S and T292S, respectively. In still a further embodiment, the polypeptide comprises one or more additional mutations at residues: (i) 12, 17, 68, 274, and 321 of SEQ ID NO:2; (ii) 25, 30, 80, 285 and 332 of SEQ ID NO:4; and (iii) 14, 19, 69, and 274 of SEQ ID NO:6. In yet a further embodiment, the polypeptide comprises the following residues at the following positions, wherein at least one position identified in (i)-(iii) is: substituting an L at position 12, 25, or 14, of SEQ ID NO:2, 4, or 6, respectively; and/or substituting G at position 17, 30, or 19 SEQ ID NO:2, 4, or 6, respectively; and/or substituting a V at position 68, 80, or 69 of SEQ ID NO:2, 4, or 6, respectively; and/or substituting S or L at position 274, 285, or 274 of SEQ ID NO:2, 4, or 6, respectively; and/or substituting S at position 292, 303, or 292 of SEQ ID NO:2, 4, or 6, respectively; and/or substituting A at position 321 or 332 of SEQ ID NO:2 or 4, respectively. In another embodiment, the polypeptide comprises one or more additional mutations corresponding to a residue selected from the group consisting of residue 2, 4, 5, 10, 11, 13, 16, 20, 21, 35, 36, 41, 59, 67, 89, 95, 123, 127, 144, 146, 150, 166, 178, 180, 181, 182, 220, 233, 267, 272, 284, 323, 384 and any combination thereof of SEQ ID NO:2. In another embodiment, the polypeptide comprises (i) a sequence of SEQ ID NO:10 that include up to 50, 25, 10, or 5 conservative amino acid substitutions excluding residues 292 of SEQ ID NO:10; or (ii) a sequence that is at least 80%, 90%, 95%, 98%, or 100% identical to SEQ ID NO:10 and comprises an S at position 292. In another embodiment, the polypeptide comprises (i) a sequence of SEQ ID NO:12 that include up to 50, 25, 10, or 5 conservative amino acid substitutions excluding residues 12, 17, 68, 274, 292 and 321 of SEQ ID NO:12; or (ii) a sequence that is at least 80%, 90%, 95%, 98%, or 100% identical to SEQ ID NO:12 and comprises the following amino acids residues: L12, G17, V68, S292, S274 and A321. In yet another embodiment, the polypeptide comprises (i) a sequence of SEQ ID NO:14 that include up to 50, 25, 10, or 5 conservative amino acid substitutions excluding residues 17, 68, 95, 274, 292 and 321 of SEQ ID NO:14; or (ii) a sequence that is at least 80%, 90%, 95%, 98%, or 100% identical to SEQ ID NO:14 and comprises the following amino acids residues: G17, V68, L95, S274, S292 and A321. In another embodiment, the polypeptide comprises (i) a sequence of SEQ ID NO:16 that include up to 50, 25, 10, or 5 conservative amino acid substitutions excluding residues 17, 68, 274, 292, and 321 of SEQ ID NO:16; or (ii) a sequence that is at least 80%, 90%, 95%, 98%, or 100% identical to SEQ ID NO:16 and comprises the following amino acids residues: G17, V68, S274, S292 and A321. In still another embodiment, the polypeptide comprises (i) a sequence of SEQ ID NO:18 that include up to 50, 25, 10, or 5 conservative amino acid substitutions excluding residues 16, 17, 68, 95, 274, 292, 321 and 384 of SEQ ID NO:18; or (ii) a sequence that is at least 80%, 90%, 95%, 98%, or 100% identical to SEQ ID NO:18 and comprises the following amino acids residues: V16, G17, V68, L95, S274, S292, A321 and A384. In another embodiment, the polypeptide comprises (i) a sequence of SEQ ID NO:20 that include up to 50, 25, 10, or 5 conservative amino acid substitutions excluding residues 144 and 166 of SEQ ID NO:20; or (ii) a sequence that is at least 80%, 90%, 95%, 98%, or 100% identical to SEQ ID NO:20 and comprises the following amino acids residues: T144 and D166. In another embodiment, the polypeptide comprises (i) a sequence of SEQ ID NO:22 that include up to 50, 25, 10, or 5 conservative amino acid substitutions excluding residues 25, 30, 80, 285, 303, and 332 of SEQ ID NO:22; or (ii) a sequence that is at least 80%, 90%, 95%, 98%, or 100% identical to SEQ ID NO:22 and comprises the following amino acids residues: L25, G30, V80, S285, S303 and A332. In still another embodiment, the polypeptide comprises (i) a sequence of SEQ ID NO:24 that include up to 50, 25, 10, or 5 conservative amino acid substitutions excluding residues 156 and 178 of SEQ ID NO:24; or (ii) a sequence that is at least 80%, 90%, 95%, 98%, or 100% identical to SEQ ID NO:24 and comprises the following amino acids residues: T156 and D178. In another embodiment, the polypeptide comprises (i) a sequence of SEQ ID NO:26 that include up to 50, 25, 10, or 5 conservative amino acid substitutions excluding residues 292 of SEQ ID NO:26; or (ii) a sequence that is at least 80%, 90%, 95%, 98%, or 100% identical to SEQ ID NO:26 and comprises an S at position 292. In yet another embodiment, the polypeptide comprises (i) a sequence of SEQ ID NO:28 that include up to 50, 25, 10, or 5 conservative amino acid substitutions excluding residues 19 of SEQ ID NO:28; or (ii) a sequence that is at least 80%, 90%, 95%, 98%, or 100% identical to SEQ ID NO:28 and comprises an G at position 19. In yet another embodiment, the polypeptide comprises (i) a sequence of SEQ ID NO:30 that include up to 50, 25, 10, or 5 conservative amino acid substitutions excluding residues 19 and 292 of SEQ ID NO:30; or (ii) a sequence that is at least 80%, 90%, 95%, 98%, or 100% identical to SEQ ID NO:30 and comprises the following amino acids residues: G19 and S292. In another embodiment, the polypeptide comprises (i) a sequence of SEQ ID NO:32 that include up to 50, 25, 10, or 5 conservative amino acid substitutions excluding residues 19 and 69 of SEQ ID NO:32; or (ii) a sequence that is at least 80%, 90%, 95%, 98%, or 100% identical to SEQ ID NO:32 and comprises the following amino acids residues: G19 and V69. In still another embodiment, the polypeptide comprises (i) a sequence of SEQ ID NO:34 that include up to 50, 25, 10, or 5 conservative amino acid substitutions excluding residues 19, 69 and 292 of SEQ ID NO:34; or (ii) a sequence that is at least 80%, 90%, 95%, 98%, or 100% identical to SEQ ID NO:34 and comprises the following amino acids residues: G19, V69 and S292. In another embodiment, the polypeptide comprises (i) a sequence of SEQ ID NO:36 that include up to 50, 25, 10, or 5 conservative amino acid substitutions excluding residues 145 and 167 of SEQ ID NO:36; or (ii) a sequence that is at least 80%, 90%, 95%, 98%, or 100% identical to SEQ ID NO:36 and comprises the following amino acids residues: T145 and D167. In yet another embodiment, the polypeptide comprises (i) a sequence of SEQ ID NO:38 that include up to 50, 25, 10, or 5 conservative amino acid substitutions excluding residues 69 and 292 of SEQ ID NO:38; or (ii) a sequence that is at least 80%, 90%, 95%, 98%, or 100% identical to SEQ ID NO:38 and comprises the following amino acids residues: V69 and S292. In another embodiment, the polypeptide comprises (i) a sequence of SEQ ID NO:40 that include up to 50, 25, 10, or 5 conservative amino acid substitutions excluding residues 149 and 171 of SEQ ID NO:40; or (ii) a sequence that is at least 80%, 90%, 95%, 98%, or 100% identical to SEQ ID NO:40 and comprises the following amino acids residues: T149 and D171.

The disclosure also provides an isolated nucleic acid encoding any of the foregoing recombinant polypeptides.

The disclosure provides a vector comprising the nucleic acid molecule of the disclosure. In one embodiment, the vector is an expression vector.

The disclosure also provides host cells transfected with an isolated nucleic acid or vector of the disclosure.

The disclosure also provides a method for producing tryptophan, a non-canonical amino acid and/or an unnatural amino acid comprising contacting an indole or indole analog and L-serine or L-threonine with a polypeptide of the disclosure.

The disclosure also provides a method for producing a β-methyl-tryptophan or analog thereof, the method comprising: (a) providing L-threonine, an indole or indole analog and a polypeptide (e.g., a mutant TrpB) of the disclosure; and (b) admixing the components of (a) in a reaction for a time and under conditions to the β-methyl-tryptophan or analog thereof. In one embodiment, the indole analog is a compound according to

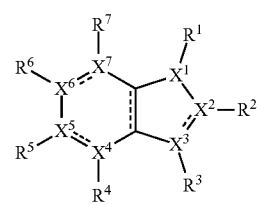

Formula I wherein $X_1$-$X_7$ are independently either a carbon, nitrogen, oxygen, or sulfur; $R_1$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen. In a further embodiment, the indole analog is selected from the group consisting of:

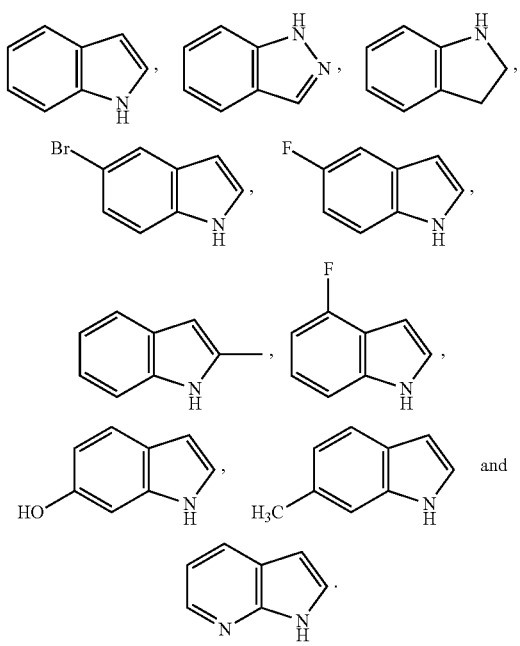

In another embodiment, the β-methyl-tryptophan or analog thereof is selected from the group consisting of:

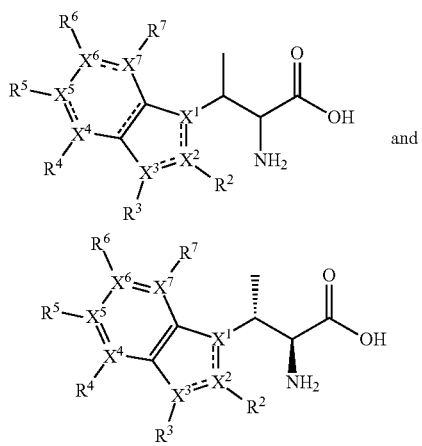

wherein $X_1$-$X_7$ are independently either a carbon, nitrogen, oxygen, or sulfur; $R_2$-$R_7$ are each independently selected from the group consisting of H, —OH, alkyl, aryl, alkoxy, alkenes, alkynes, and substitutions of the foregoing, sulfur-containing group, nitrogen-containing groups, oxygen-containing group, or halogen. In a further embodiment, the β-methyl-tryptophan or analog thereof is selected from the group consisting of:

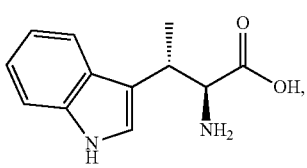

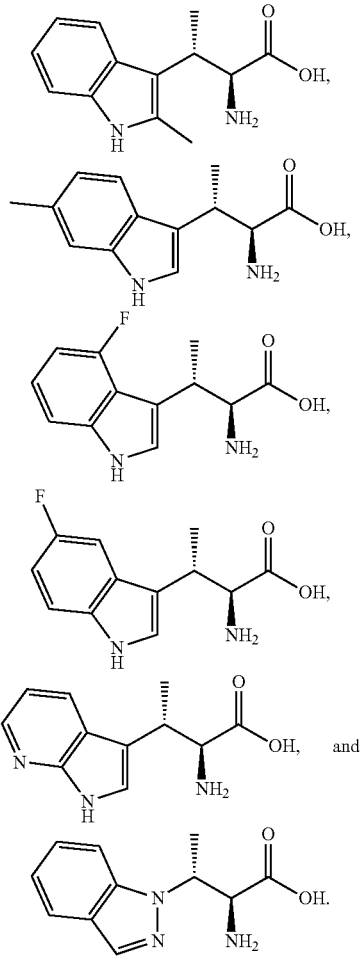

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 2 shows a multiple sequence alignment of Pf (SEQ ID NO:2), Af (SEQ ID NO:4), Tm (SEQ ID NO:6) and Ec (SEQ ID NO:8) TrpB homologs. The mutated residues in PfTrpB$^{OB2}$ are shown above the first line. Symbols under sequences: (*) identify identical residues, (:) report for residues of equal nature, and (.) recognize roughly similar residues.

Like reference symbols in the various drawings indicate like elements.

DETAILED DESCRIPTION

Figure 1A:
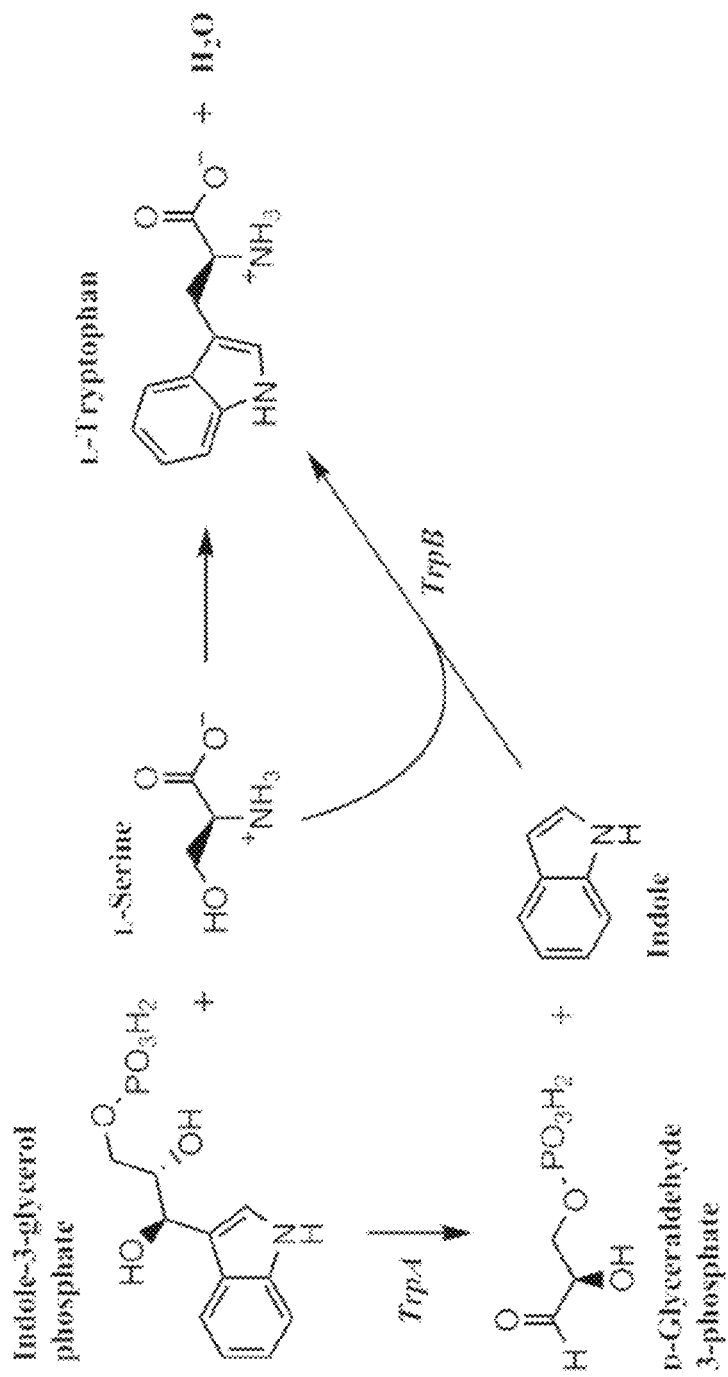
FIG. 1A shows the last two steps in the biosynthesis of L-Trp catalyzed by the multi-enzyme complex tryptophan synthase. IGP is cleaved into G3P and indole by TrpA. The latter serves as nucleophile in the TrpB-catalyzed replacement reaction of the L-Ser hydroxyl to give L-Trp. G3P and water are released as side products of the overall reaction.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

TrpS is a naturally promiscuous enzyme complex: the model system from *S. typhimurium* catalyzes its β-substitution reaction with most haloindoles, methylindoles, and aminoindoles, along with an assortment of nonindole nucleophiles for C—S, C—N, and C—C bond formation. Such noncanonical amino acids (NCAAs) have diverse applications in chemical biology, serve as intermediates in the synthesis of natural products, and are privileged scaffolds for the development of pharmaceuticals. Despite its natural ability to produce these desirable compounds, TrpS has enjoyed only limited application. Optimized methods are restricted by low substrate concentrations and yields typically below 50%. To produce NCAAs, researchers have used the *S. typhimurium* TrpS complex (StTrpS), which suffers from poor thermostability and low tolerance to organic solvents. Although only the reactivity of the β-subunit, coupling of L-serine and indole, is necessary and desirable for synthetic applications, using TrpB as an isolated enzyme has not been feasible. Outside of its native complex, TrpB loses up to 95% of its native activity and is subject to inactivation.

Tryptophan synthase is typically found as a bi-enzyme complex linearly arranged. The smaller α-subunit (27 kDa) adopts a TIM β/α barrel. The PLP-dependent β-subunit (43 kDa) is of a fold type II conformation and features a monovalent cation-binding site adjacent to its catalytic center. The active sites of the subunits are interconnected by a substrate tunnel for efficient channeling of the common metabolite, indole. A great degree of allosteric regulation by an intricate network of interactions is necessary to synchronize the catalytic activities in the spatially separated active sites of the tryptophan synthase complex. A variety of analytical tools have been sought out to gain a more detailed mechanical and chemical understanding of the allosteric regulation mechanisms involved in catalysis, including biochemical solution experiments, mutational studies, and X-ray crystallography. The most essential feature allowing for the high enzymatic efficiency of tryptophan synthase is the direct channeling of the common intermediate, indole, through the hydrophobic 25-Å long substrate tunnel interconnecting the active sites of the subunits.

The interest in non-canonical amino acids (NCAA) has been exponentially growing ever since the possibility of their site-specific introduction into enzymes both in vivo and in vitro through nonsense codon suppression. A large and diverse library of unnatural amino acids (UAAs) has been established to address unresolved questions in protein structure and function with unreached precision. The applications are numerous, including incorporation of biophysical probes, such as fluorescent tags and spin labels, production of "caged" proteins with photoreactive side chains, assessing protein stability, and improving natural enzyme activity.

Furthermore, compounds of peptidic structure are often found in nature and employed in drugs by the pharmaceutical industry. However, chemical synthesis of these substances can be challenging. As part of the green-chemistry movement the enzymatic synthesis of non-canonical peptidic compounds has gained in importance. In addition to the mild conditions and nontoxic reagents, enzymatic reactions often occur with high enantiomeric purity and remarkable rate acceleration.

Tryptophan synthase has also been extensively employed for the enzymatic synthesis of a variety of tryptophan analogues, including methylated, halogenated, and aminated L-tryptophans, dihydroisotryptophan, and selenatryptophan. The common basic approach of the aforementioned cases consists of creating batch reactions of indole analogues and L-Ser catalyzed by native tryptophan synthases.

Tryptophan synthase comprises a polymeric polypeptide of two alpha and two beta subunits referred to a TrpA (tryptophan-α) and TrpB (tryptophan-β) that form an α-ββ-α complex. The α and β subunits have molecular masses of 27 and 43 kDa, respectively. The α subunit has a TIM barrel conformation. The β subunit has a fold type II conformation and a binding site adjacent to the active site for monovalent cations. Their assembly into a complex leads to structural changes in both subunits resulting in reciprocal activation. There are two main mechanisms for intersubunit communication. First, the COMM domain of the β-subunit (residues Gly97 to Gly187 of PfTrpB) and the α-loop2 of the α-subunit interact. Additionally, there are interactions between the αGly181 and βSer178 residues. The active sites are regulated allosterically and undergo transitions between open, inactive, and closed, active, states.

As used herein an "indole analog" refers to any number of known derivatives of indole as set forth in Formula I:

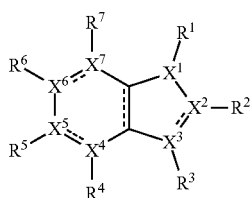

wherein $X_1$-$X_7$ are independently either a carbon, nitrogen, oxygen, or sulfur; $R_1$-$R_7$ are each independently selected from the group consisting of H, —OH, alkyl, aryl, alkoxy, alkenes, alkynes, and substitutions of the foregoing, sulfur-containing group (e.g., thioalkoxy), nitrogen-containing groups (e.g., amide, amino, nitro, azide, and cyano), oxygen-containing group (e.g., ketone, aldehyde, ester, ether, carboxylic acid, and acyl halide), or halogen (e.g., Br, F, iodine). In one embodiment, the indole analog is selected from the group consisting of:

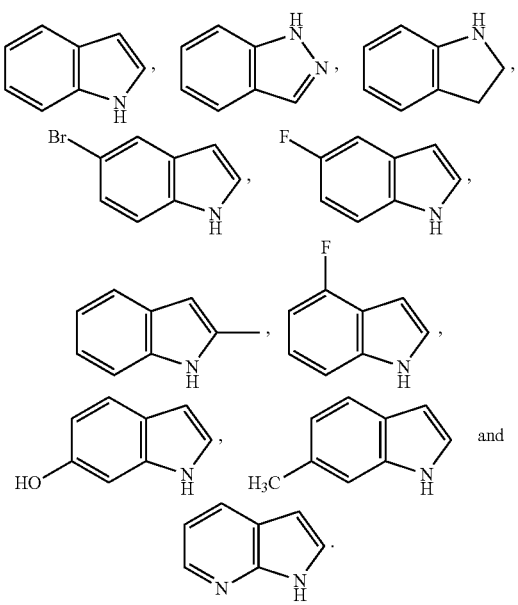

As used herein a "mutant TrpB" or "engineered TrpB" refers to the β-subunit of tryptophan synthase (TrpS) that has been recombinantly modified to differ from the wild-type sequence. A mutant TrpB typically has a desired substrates specificity, turnover number, product production, stability etc. that differ from a wild-type enzyme or subunit. A mutant TrpB can be derived from a number of homologs of diverse origin, wherein the mutant TrpB differs from a wild-type of parental polypeptide by one or more (e.g., 2, 3, 4, 5, 6, 7, 8, 9, 10, 15, 20, 25, 30 or more, up to about 50) mutations and wherein the mutant TrpB can generate NCAA or UAA amino acids from an indole analog and a serine or threonine substrate and/or wherein the mutant TrpB functions independent of the TrpA subunit.

A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Modified amino acids are amino acids that are chemically modified. Non-limiting examples of a modified amino acid include a glycosylated amino acid, a sulfated amino acid, a prenylated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "parental polypeptide" refers to a polypeptide used to generate a recombinant or mutant polypeptide. The term "parental polypeptide" describes a polypeptide that occurs in nature, i.e. a "wild-type" cell that has not been genetically modified. The term "parental polypeptide" also describes a polypeptide that serves as the "parent" for further engineering. For example, a wild-type polypeptide can be mutant to have a first mutation or set of mutations that can provide a desired biological activity or be "silent mutations". This first mutant polypeptide can then act as a parental polypeptide in the generation of second mutation or set of mutations that can provide a desired biological activity or be silent mutations.

The term "polynucleotide," "nucleic acid" or "recombinant nucleic acid" refers to polynucleotides such as deoxyribonucleic acid (DNA), and, where appropriate, ribonucleic acid (RNA).

A "protein" or "polypeptide", which terms are used interchangeably herein, comprises one or more chains of chemical building blocks called amino acids that are linked together by chemical bonds called peptide bonds. A protein or polypeptide can function as an enzyme. An "enzyme" means any substance, composed wholly or largely of protein, that catalyzes or promotes, more or less specifically, one or more chemical or biochemical reactions.

As used herein "TrpB" refers to a diverse set of homologs of the β-subunit of tryptophan synthase. A wild-type TrpB can be used as a parental polypeptide for mutation. For example, the TrpB from *Pyroccous furiosus* (PfTrpB) is used as a reference sequence in the disclosure and comprises or consists of the sequence as set forth in SEQ ID NO:2. Homologs of PfTrpB are known and include, for example, TrpB from *Archaeoglobus fulgidus* (Af), which has 72% sequence identity to PfTrpB, and TrpB from *Escherichia coli* (Ec), which has 57% sequence identity to PfTrpB. Accordingly, wild-type TrpB sequences having at least 57% sequence identity to SEQ ID NO:2 can be used as a parental polypeptide for mutations to form mutant TrpB. The disclosure demonstrates that a diverse set of TrpB homologs based on a phylogenetic analysis of TrpB, including *Archaeoglobus fulgidus* (AfTrpB, 72% sequence identity), *Thermotoga maritima* (TmTrpB, 64%), and *Escherichia coli* (EcTrpB, 57%) are useful in obtaining desirable mutant TrpBs. A multiple-sequence alignment with PfTrpB is shown in FIG. 2.

The engineered/mutant tryptophan beta-subunits (TrpBs) described throughout the present disclosure were acquired by accumulating point mutations in directed evolution experiments from a parental polypeptide. An alternative method for making libraries for directed evolution to obtain modified TrpBs with new or altered properties is recombination, or chimeragenesis, in which portions of homologous TrpBs are swapped to form functional chimeras. Therefore, the amino acid mutations made in this way are less disruptive, on average, than random mutations. A structure-based algorithm, such as SCHEMA, identifies fragments of proteins that can be recombined to minimize disruptive interactions that would prevent the protein from folding into its active form.

Provided herein are variants of TrpB that catalyze the synthesis of NCAAs and UAAs. The reaction uses indole analogs and L-serine or L-threonine or analogs thereof.

The term "total turnover number" (TTN) is the total number of substrate molecules converted to product (or turned over) by an enzyme over its lifetime or during a specified time period. TTN is an important figure of merit for a catalyst because it allows for the calculation of the total amount of product that can be made from a given quantity of catalyst.

The modified TrpB subunits used as catalyst can function at ambient temperature or higher (e.g., from 20° C. to 95° C., typically about 75° C.) and ambient pressure.

The mutant TrpBs of the disclosure have enormous potential for applications in drug discovery, chemical synthesis, pharmaceutical preparations, and biotechnology. However, tailoring TrpBs to accept nonnatural substrates, as required by many applications, is difficult in this catalytic system, which involves multiple subunits having allosteric interactions. Compared to their natural counterparts, engineered/mutant TrpBs of the disclosure have improved catalytic and coupling efficiencies.

The phrase "TrpB activity" refers to the biological activity of TrpB or mutants thereof. For example, TrpB activity includes the ability of the TrpB polypeptide to produce NCAAs or UAAs from an indole or derivative thereof and L-serine or L-threonine.

The term "substrate" or "suitable substrate" means any substance or compound that is converted or meant to be converted into another compound by the action of an enzyme catalyst. The term includes indole and indole derivatives as well as serine or threonine and derivatives thereof.

As will be described in more detail below, the disclosure is based, at least in part, on the generation and expression of novel enzymes that catalyze the conversion of indole or indole derivatives and serine or threonine to NCAAs or UAAs. In one embodiment, polypeptides that have been engineered to convert an indole and serine or threonine to an NCAA or UAA are provided.

While the TrpB mutants will be described in more detail below, it is understood that polypeptides of the disclosure may contain one or more modified amino acids. Amino acid(s) are modified, for example, co-translationally or post-translationally during recombinant production (e.g., N-linked glycosylation at N—X—S/T motifs during expression in mammalian cells) or modified by synthetic means.

The disclosure demonstrates the engineering of TrpB through directed evolution to provide a β-subunit that has biological activity independent of TrpA and which can produce tryptophan and/or NCAAs or UAAs from suitable substrates. For example, the evolution of TrpB into TrpB mutants shows that members of the TrpB family can be evolved by point mutations and screening for function on various substrates and various products production.

Referring to the sequence comparison of various TrpB subunits in FIG. 2, SEQ ID NO:2 includes the amino acid sequence of TrpB isolated from *Pyroccocus furiosus* designated PfTrpB. SEQ ID NO:4 provides the amino acid sequence of wild-type TrpB from *Archaeoglobus fulgidus*. This wild-type TrpB designated AfTrpB shares 72% amino acid sequence identity to PfTrpB (SEQ ID NO:2). SEQ ID NO:6 includes the amino acid sequence of wild-type TrpB from *Thermotoga maritima*. This wild-type TrpB is designated TmTrpB and shares 64% amino acid sequence identity to PfTrpB (SEQ ID NO:2). SEQ ID NO:8 includes the amino acid sequence of wild-type TrpB from *Escherichia coli*. This wild-type TrpB is designated EcTrpB and shares 57% amino acid sequence identity to PfTrpB (SEQ ID NO:2).

The TrpBs set forth in SEQ ID NOs:2, 4, 6, and 8 are closely related to one another and show a high degree of sequence identity and activity. The sequences can be aligned and conserved amino acids identified based upon the alignment. The alignment provided in FIG. 2 identifies "equivalent positions" in the sequences. An equivalent position denotes a position which, on the basis of the alignment of the sequence of the parent TrpB in question with the "reference" TrpB amino acid sequence in question (e.g. SEQ ID NO: 2) so as to achieve juxtapositioning of amino acid residues which are common to both, corresponds most closely to a particular position in the reference sequence in question. This process can cause gaps or insertions to appear in the sequences. In the alignment of FIG. 2, equivalent positions are shown lined up vertically with one another. For example, position 47 in SEQ ID NO: 2 is equivalent to position 60 in SEQ ID NO: 4 and position 49 in SEQ ID NO: 6 and position 53 in SEQ ID NO:8.

Provided herein are engineered mutant TrpB polypeptides capable of producing NCAAs and UAAs. Protein engineering of TrpBs from other sources can be expected to lead to a similar result using the basic alignment and mutation tools described herein. It is well known in the art that amino acid substitutions having a particular effect (e.g. that confer activity toward a new substrate) can have the same effect in closely related proteins. For example, the alignment of these four homologs illustrates the high degree of sequence similarity among the four TrpBs. Moreover, it will be readily apparent based upon the "mutation" row, which exemplary mutations can be and have been made. It has been shown on multiple occasions that amino acid substitutions at equivalent positions in these enzymes have equivalent effects on function. For example, the substitution of M144T and N166D in PfTrpB increases the $k_{cat}$ by at least 2-fold. The same substitution of the equivalent position in AfTrpB, TmTrpB, and EcTrpB, which is M156T/N178D, M145T/N167D, and M149T/N171D (respectively), has the same effect. Additionally, these TrpB polypeptides can be subjected to rounds of directed evolution using the techniques and screens described herein to obtain and/or increase substrate specificity and product generation.

Accordingly, in one embodiment, a mutant TrpB polypeptide is provided that comprises at least 57% identity to SEQ ID NO:2 and comprises activating mutations at position 144 and 166. In one embodiment, the activating mutations are an M144T and N166D mutation. In another embodiment, the mutant TrpB comprises 50, 25, 10, 5 or fewer conservative substitutions to SEQ ID NO:8 and a M149T and N171D mutation. In another embodiment, the mutant TrpB comprises 50, 25, 10, 5 or fewer conservative substitutions to SEQ ID NO:6 and a M145T and N167D mutation. In another embodiment, the mutant TrpB comprises 50, 25, 10, 5 or fewer conservative substitutions to SEQ ID NO:4 and a M156T and N178D mutation.

In yet another embodiment, a mutant TrpB polypeptide is provided that comprises SEQ ID NO:2 and has at least 50, 25, 10, 5 or fewer conservative substitutions and activating mutations at positions 12, 17, 68, 274, 292 and 321. In a further embodiment, the activating mutations are P12L, E17G, I68V, F274S, T292S and T321A.

In yet another embodiment, a mutant TrpB polypeptide is provided that comprises SEQ ID NO:4 and has at least 50, 25, 10, 5 or fewer conservative substitutions and activating mutations at positions 25, 30, 80, 285, 303 and 332. In a further embodiment, the activating mutations are P25L, E30G, I80V, F285S, T303S and T332A.

In yet another embodiment, a mutant TrpB polypeptide is provided that comprises SEQ ID NO:6 and has at least 50, 25, 10, 5 or fewer conservative substitutions and activating mutations at positions 19, 68 and 292. In a further embodiment, the activating mutations are P19L, I68V, and T292S.

In one embodiment, a mutant TrpB polypeptide is provided that comprises at least 60% sequence identity to SEQ ID NO:2 and comprises at least a mutation at residue 292 of SEQ ID NO:2 or a related position in a homolog of SEQ ID NO:2 (e.g., residue 303 of SEQ ID NO:4, or residue 292 of SEQ ID NO:6). In one embodiment, the residue is replaced with a Serine residue. In a particular embodiment, the mutant TrpB comprises at least 65%, 70%, 75%, 80%, 85%, 88%, 90%, 92%, 95%, 98% or at least 99% identity to SEQ ID NO:2 and comprises a mutation at position 292 or a related position in a homolog of SEQ ID NO:2. In still a further embodiment, the TrpB polypeptide can comprise one or more additional mutations at residues: (a) 12, 17, 68, 274, and 321 of SEQ ID NO:2; (b) 25, 30, 80, 285, and 332 of SEQ ID NO:4; (c) 14, 19, 69, 274, and 321 of SEQ ID NO:6; and (d) 18, 23, 73, 279, and 326 of SEQ ID NO:8. In still a further embodiment, the amino acid sequence of the TrpB mutant includes the following residues at the following positions, wherein at least one position identified in (a)-(d) a specific mutation is provided. In one embodiment, the specific mutation is substituting an L at position 12, 25, 14, or 18 of SEQ ID NO:2, 4, 6, or 8, respectively; and/or substituting G at position 17, 30, 19, or 23 of SEQ ID NO:2, 4, 6, or 8, respectively; and/or substituting a V at position 68 68, 80, 69, or 73 of SEQ ID NO:2, 4, 6, or 8, respectively; and/or substituting S or L at position 274, 285, 274, or 279 of SEQ ID NO:2, 4, 6, or 8, respectively; and/or substituting S at position 292, 303, or 292 of SEQ ID NO:2, 4, or 6, respectively; and/or A at position 321, 332, or 326 of SEQ ID NO:2, 4, or 8, respectively. In still a further embodiment, one or more additional mutations may be present. The one or more additional mutations can be at residues selected from the group consisting of residue 2, 4, 5, 10, 11, 13, 16, 20, 21, 35, 36, 41, 59, 67, 89, 95, 123, 127, 144, 146, 150, 166, 178, 180, 181, 182, 220, 233, 267, 272, 284, 323, 384 of SEQ ID NO:2.

In yet other various embodiments, mutant TrpB polypeptides are provided. The mutant TrpB polypeptides include up to 50, 25, 10, or 5 conservative amino acid substitutions excluding residues: (a) 12, 17, 68, 274, 292 and 321 of SEQ ID NO:2; (b) 25, 30, 80, 285, 303, and 332 of SEQ ID NO:4; (c) 14, 19, 69, 274, 292 and 321 of SEQ ID NO:6; and (d) 18, 23, 73, 279, 297 and 326 of SEQ ID NO:8. The amino acid sequence includes the following residues at the following positions, wherein at at least one position identified in (a)-(d) a specific mutation is provided. In one embodiment, the specific mutation is substituting an L at position 12, 25, 14, or 18 of SEQ ID NO:2, 4, 6, or 8, respectively; and/or substituting G at position 17, 30, 19 or 23 of SEQ ID NO:2, 4, 6, or 8, respectively; and/or substituting a V at position 68 68, 80, 69 or 73 of SEQ ID NO:2, 4, 6, or 8, respectively; and/or substituting S or L at position 274, 285, 274, or 279 of SEQ ID NO:2, 4, 6, or 8, respectively; and/or substituting S at position 292, 303, 292, or 297 of SEQ ID NO:2, 4, 6, or 8, respectively (note that for SEQ ID NO:8 although referred to in this paragraph as a specific mutation, the residue at position 297 is not mutated); and/or A at position 321, 332, 321 or 326 of SEQ ID NO:2, 4, 6, or 8, respectively (note that for SEQ ID NO:6 although referred to in this paragraph as a specific mutation, the residue at position 321 is not mutated). In still a further embodiment, one or more additional mutations may be present. The one or more additional mutations are at residues selected from the group consisting of residue 2, 4, 5, 10, 11, 13, 16, 20, 21, 35, 36, 41, 59, 67, 89, 95, 123, 127, 144, 146, 150, 166, 178, 180, 181, 182, 220, 233, 267, 272, 284, 323, 384 of SEQ ID NO:2.

In another embodiment, the disclosure provides a polypeptide that comprises at least 57% identity to SEQ ID NO:2 and has at least one mutation at (a) a residue selected from the group consisting of 12, 17, 68, 274, 292, 321 and any combination thereof of SEQ ID NO:2; (b) a residue selected from the group consisting of 25, 30, 80, 285, 303, 332, and any combination thereof of SEQ ID NO:4; (c) a residue selected from the group consisting of 14, 19, 69, 274, or 292 and any combination thereof of SEQ ID NO:6; and (d) a residue selected from the group consisting of 18, 23, 73, 279, or 326 and any combination thereof of SEQ ID NO:8. In a further embodiment, at least one position identified in (a)-(d) includes a substitution of L at position 12, 25, 14, or 18 of SEQ ID NO:2, 4, 6, or 8, respectively; and/or substituting G at position 17, 30, 19 or 23 of SEQ ID NO:2, 4, 6, or 8, respectively; and/or substituting a V at position 68 68, 80, 69 or 73 of SEQ ID NO:2, 4, 6, or 8, respectively; and/or substituting S or L at position 274, 285, 274, or 279 of SEQ ID NO:2, 4, 6, or 8, respectively; and/or substituting S at position 292, 303, or 292 of SEQ ID NO:2, 4, or 6, respectively; and/or A at position 321, 332, or 326 of SEQ ID NO:2, 4, or 8, respectively.

In yet another embodiment, a mutant TrpB polypeptide comprises a sequence of SEQ ID NO:10 that include up to 50, 25, 10, or 5 conservative amino acid substitutions excluding residues 292 of SEQ ID NO:10. In still another embodiment, a mutant TrpB polypeptide is provided that comprises a sequence that is at least 80%, 90%, 95%, 98%, or 100% identical to SEQ ID NO:10 and comprises an S at position 292.

In yet another embodiment, a mutant TrpB polypeptide comprises a sequence of SEQ ID NO:12 that include up to 50, 25, 10, or 5 conservative amino acid substitutions excluding residues 12, 17, 68, 274, 292 and 321 of SEQ ID NO:12. In still another embodiment, a mutant TrpB polypeptide is provided that comprises a sequence that is at least 80%, 90%, 95%, 98%, or 100% identical to SEQ ID NO:12 and comprises the following amino acids residues: L12, G17, V68, S292, S274, and A321.

In yet another embodiment, a mutant TrpB polypeptide comprises a sequence of SEQ ID NO:14 that include up to 50, 25, 10, or 5 conservative amino acid substitutions excluding residues 17, 68, 95, 274, 292, and 321 of SEQ ID NO:14. In still another embodiment, a mutant TrpB polypeptide is provided that comprises a sequence that is at least 80%, 90%, 95%, 98%, or 100% identical to SEQ ID NO:14 and comprises the following amino acids residues: G17, V68, L95, S274, S292, and A321.

In yet another embodiment, a mutant TrpB polypeptide comprises a sequence of SEQ ID NO:16 that include up to 50, 25, 10, or 5 conservative amino acid substitutions excluding residues 17, 68, 274, 292, and 321 of SEQ ID NO:16. In still another embodiment, a mutant TrpB polypeptide is provided that comprises a sequence that is at least 80%, 90%, 95%, 98%, or 100% identical to SEQ ID NO:16 and comprises the following amino acids residues: G17, V68, S274, S292, and A321.

In yet another embodiment, a mutant TrpB polypeptide comprises a sequence of SEQ ID NO:18 that include up to 50, 25, 10, or 5 conservative amino acid substitutions excluding residues 16, 17, 68, 95, 274, 292, 321, and 384 of SEQ ID NO:18. In still another embodiment, a mutant TrpB polypeptide is provided that comprises a sequence that is at least 80%, 90%, 95%, 98%, or 100% identical to SEQ ID NO:18 and comprises the following amino acids residues: V16, G17, V68, L95, S274, S292, A321, and A384.

In yet another embodiment, a mutant TrpB polypeptide comprises a sequence of SEQ ID NO:20 that include up to 50, 25, 10, or 5 conservative amino acid substitutions excluding residues 144 and 166 of SEQ ID NO:20. In still another embodiment, a mutant TrpB polypeptide is provided that comprises a sequence that is at least 80%, 90%, 95%, 98%, or 100% identical to SEQ ID NO:20 and comprises the following amino acids residues: T144 and D166.

In yet another embodiment, a mutant TrpB polypeptide comprises a sequence of SEQ ID NO:22 that include up to 50, 25, 10, or 5 conservative amino acid substitutions excluding residues 25, 30, 80, 285, 303, and 332 of SEQ ID NO:22. In still another embodiment, a mutant TrpB polypeptide is provided that comprises a sequence that is at least 80%, 90%, 95%, 98%, or 100% identical to SEQ ID NO:22 and comprises the following amino acids residues: L25, G30, V80, S285, S303, and A332.

In yet another embodiment, a mutant TrpB polypeptide comprises a sequence of SEQ ID NO:24 that include up to 50, 25, 10, or 5 conservative amino acid substitutions excluding residues 156 and 178 of SEQ ID NO:24. In still another embodiment, a mutant TrpB polypeptide is provided that comprises a sequence that is at least 80%, 90%, 95%, 98%, or 100% identical to SEQ ID NO:24 and comprises the following amino acids residues: T156 and D178.

In yet another embodiment, a mutant TrpB polypeptide comprises a sequence of SEQ ID NO:26 that include up to 50, 25, 10, or 5 conservative amino acid substitutions excluding residues 292 of SEQ ID NO:26. In still another embodiment, a mutant TrpB polypeptide is provided that comprises a sequence that is at least 80%, 90%, 95%, 98%, or 100% identical to SEQ ID NO:26 and comprises an S at position 292.

In yet another embodiment, a mutant TrpB polypeptide comprises a sequence of SEQ ID NO:28 that include up to 50, 25, 10, or 5 conservative amino acid substitutions excluding residues 19 of SEQ ID NO:28. In still another embodiment, a mutant TrpB polypeptide is provided that comprises a sequence that is at least 80%, 90%, 95%, 98%, or 100% identical to SEQ ID NO:28 and comprises an G at position 19.

In yet another embodiment, a mutant TrpB polypeptide comprises a sequence of SEQ ID NO:30 that include up to 50, 25, 10, or 5 conservative amino acid substitutions excluding residues 19 and 292 of SEQ ID NO:30. In still another embodiment, a mutant TrpB polypeptide is provided that comprises a sequence that is at least 80%, 90%, 95%, 98%, or 100% identical to SEQ ID NO:30 and comprises the following amino acids residues: G19 and S292.

In yet another embodiment, a mutant TrpB polypeptide comprises a sequence of SEQ ID NO:32 that include up to 50, 25, 10, or 5 conservative amino acid substitutions excluding residues 19 and 69 of SEQ ID NO:32. In still another embodiment, a mutant TrpB polypeptide is provided that comprises a sequence that is at least 80%, 90%, 95%, 98%, or 100% identical to SEQ ID NO:32 and comprises the following amino acids residues: G19 and V69.

In yet another embodiment, a mutant TrpB polypeptide comprises a sequence of SEQ ID NO:34 that include up to 50, 25, 10, or 5 conservative amino acid substitutions excluding residues 19, 69 and 292 of SEQ ID NO:34. In still another embodiment, a mutant TrpB polypeptide is provided that comprises a sequence that is at least 80%, 90%, 95%, 98%, or 100% identical to SEQ ID NO:34 and comprises the following amino acids residues: G19, V69, and S292.

In yet another embodiment, a mutant TrpB polypeptide comprises a sequence of SEQ ID NO:36 that include up to 50, 25, 10, or 5 conservative amino acid substitutions excluding residues 145 and 167 of SEQ ID NO:36. In still another embodiment, a mutant TrpB polypeptide is provided that comprises a sequence that is at least 80%, 90%, 95%, 98%, or 100% identical to SEQ ID NO:36 and comprises the following amino acids residues: T145 and D167.

In yet another embodiment, a mutant TrpB polypeptide comprises a sequence of SEQ ID NO:38 that include up to 50, 25, 10, or 5 conservative amino acid substitutions excluding residues 69 and 292 of SEQ ID NO:38. In still another embodiment, a mutant TrpB polypeptide is provided that comprises a sequence that is at least 80%, 90%, 95%, 98%, or 100% identical to SEQ ID NO:38 and comprises the following amino acids residues: V69 and S292.

In yet another embodiment, a mutant TrpB polypeptide comprises a sequence of SEQ ID NO:40 that include up to 50, 25, 10, or 5 conservative amino acid substitutions excluding residues 149 and 171 of SEQ ID NO:40. In still another embodiment, a mutant TrpB polypeptide is provided that comprises a sequence that is at least 80%, 90%, 95%, 98%, or 100% identical to SEQ ID NO:40 and comprises the following amino acids residues: T149 and D171.

"Conservative amino acid substitution" or, simply, "conservative variations" of a particular sequence refers to the replacement of one amino acid, or series of amino acids, with essentially identical amino acid sequences. One of skill will recognize that individual substitutions, deletions, or additions which alter, add, or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, 8, 10, 12, 14, 16, 18, 20, 22, 24, 26, 28, 30, 32, 34, 36, 28 or 40) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "TrpB mutant activity", "biological activity of TrpB mutant" or "functional activity of TrpB mutant", refers to an activity exerted by a TrpB mutant polypeptide on a TrpB substrate, as determined in vivo or in vitro, according to standard techniques. The biological activity of TrpB mutants is described herein as, for example, the ability to utilize indole or analogs thereof and L-serine or L-threonine in the generation of NCAAs or UAAs. Other measurements are described in the examples below.

One of skill in the art will appreciate that many conservative variations of the nucleic acid constructs, which are disclosed, yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence that encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

It will be appreciated by those skilled in the art that due to the degeneracy of the genetic code, a multitude of nucleotide sequences encoding mutant TrpBs of the disclosure may be produced, some of which bear substantial identity to the nucleic acid sequences explicitly disclosed herein (e.g., SEQ ID NO:1, 3, 5, 7, 9, 11, 13, 15, 17, 19, 21, 23, 25, 27, 29, 31, 33, 35, 37, and 39). For instance, codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

"Conservative variants" are proteins or enzymes in which a given amino acid residue has been changed without altering overall conformation and function of the protein or enzyme, including, but not limited to, replacement of an amino acid with one having similar properties, including polar or non-polar character, size, shape, and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, at least 90%, at least 95%, at least 98%, or at least 99%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/ identity are known in the art such as, for example, the Cluster Method, wherein similarity is based on the MEGA-LIGN algorithm, as well as BLASTN, BLASTP, and FASTA (Lipman and Pearson, 1985; Pearson and Lipman, 1988). When using all of these programs, the preferred settings are those that result in the highest sequence similarity.

"Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that result in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919 (each of which is incorporated by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402 (incorporated by reference herein), and made available to the public at the National Center for Biotechnology Information (NCBI) Website ([www.] ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402 (incorporated by reference herein).

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO:2, position 12 is P, position 13 is E, etc. When a test sequence is optimally aligned with SEQ ID NO:2, a residue in the test sequence that aligns with the P at position 12 is said to "correspond to position 12" of SEQ ID NO:2. Owing to deletions, insertion, truncations, fusions, etc., that must be taken into account when determining an optimal alignment, in general the amino acid residue number in a test sequence as determined by simply counting from the N-terminal end will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Non-conservative modifications of a particular polypeptide are those, which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. Instead, these restricted amino acids are generally chosen from a specific group or selected amino acids or are not substituted or mutated at all.

A polynucleotide, polypeptide, or other component is "isolated" or "purified" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid through the process of mutation. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant or engineered mutant of a naturally occurring gene, is recombinant. For example, an "isolated" nucleic acid molecule is one which is separated from other nucleic acid molecules which are present in the natural source of the nucleic acid. For example, with regards to genomic DNA, the term "isolated" includes nucleic acid molecules which are separated from the chromosome with which the genomic DNA is naturally associated. Typically, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The disclosure envisions multi-unit polypeptides. Such a multi-unit polypeptide would comprise for example: TrpA-mTrpB-mTrpB-TrpA. The tryptophan-α domain (and sequences thereof) of TrpS for each of *Pyrococcus furiosus, Archaeoglobus fulgidus, Thermotoga maritima*, and *Escherichia coli* are well known in the art.

In other embodiments, isolated nucleic acid molecules are provided. In one embodiment, the disclosure provides a novel family of isolated or recombinant polynucleotides referred to herein as "TrpB mutant polynucleotides" or "TrpB mutant nucleic acid molecules." TrpB mutant polynucleotide sequences are characterized by the ability to encode a TrpB mutant polypeptide. In general, the disclosure includes any nucleotide sequence that encodes any of the TrpB mutant polypeptides described herein. In some aspects of the disclosure, a TrpB mutant polynucleotide that encodes a TrpB mutant polypeptide with TrpB mutant activity is provided. The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

In one embodiment, the TrpB mutant polynucleotides comprise recombinant or isolated forms of naturally occurring nucleic acids isolated from an organism, which have been mutated by, for example, directed evolution. Exemplary TrpB polynucleotides include those that encode the wild-type polypeptides set forth in SEQ ID NO: 2, 4, 6, or 8. In another aspect of the disclosure, TrpB mutant polynucleotides are produced by diversifying, e.g., recombining and/or mutating one or more naturally occurring, isolated, or recombinant TrpB polynucleotides. As described in more detail elsewhere herein, it is often possible to generate diversified TrpB mutant polynucleotides encoding TrpB mutant polypeptides with superior functional attributes, e.g., increased catalytic function, increased stability, novel substrate or product production, or higher expression level, than a TrpB polynucleotide used as a substrate or parent in the diversification process. Exemplary polynucleotides include those that encode the TrpB mutant polypeptides set forth in SEQ ID NO: 9, 11, 13, 15, 17, 19, 21, 23, 25, 27, 29, 31, 33, 35, 37 or 39.

The polynucleotides of the disclosure have a variety of uses in, for example recombinant production (i.e., expression) of the TrpB mutant polypeptides of the disclosure and as substrates for further diversity generation, e.g., recombination reactions or mutation reactions to produce new and/or improved TrpB mutant homologues, and the like.

It is important to note that certain specific, substantial, and credible utilities of TrpB mutant polynucleotides do not require that the polynucleotide encodes a polypeptide with substantial TrpB mutant activity or even TrpB mutant activity. For example, TrpB mutant polynucleotides that do not encode active enzymes can be valuable sources of parental polynucleotides for use in diversification procedures to arrive at TrpB mutant polynucleotide with desirable functional properties (e.g., high $k_{cat}$ or $k_{cat}/K_m$, low $K_m$, high stability toward heat or other environmental factors, high transcription or translation rates, resistance to proteolytic cleavage, etc.).

TrpB mutant polynucleotides, including nucleotide sequences that encode TrpB polypeptides and variants thereof, fragments of TrpB mutant polypeptides, related fusion proteins, or functional equivalents thereof, are used in recombinant DNA molecules that direct the expression of the TrpB mutant polypeptides in appropriate host cells, such as bacterial cells. Due to the inherent degeneracy of the genetic code, other nucleic acid sequences which encode substantially the same or a functionally equivalent amino acid sequence can also be used to clone and express the TrpB mutant polynucleotides.

The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72; incorporated by reference herein). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508; incorporated by reference herein) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for S. cerevisiae and mammals are UAA and UGA, respectively. The preferred stop codon for monocotyledonous plants is UGA, whereas insects and E. coli prefer to use UAA as the stop codon (Dalphin et al. (1996) Nucl. Acids Res. 24: 216-218; incorporated by reference herein). Methodology for optimizing a nucleotide sequence for expression in a plant is provided, for example, in U.S. Pat. No. 6,015,891, and the references cited therein (incorporated herein by reference).

Accordingly, in some embodiments, nucleic acid molecules of the disclosure include: (a) a nucleic acid molecule which encodes a polypeptide comprising the amino acid sequence set forth in SEQ ID NO:10, 12, 14, 16, 18, 20, 22, 24, 26, 28, 30, 32, 34, 36, 38 or 40; (b) a nucleic acid molecule which encodes a polypeptide consisting of the amino acid sequence set forth in SEQ ID NO: 10, 12, 14, 16, 18, 20, 22, 24, 26, 28, 30, 32, 34, 36, 38 or 40; (c) a nucleic acid molecule which hybridizes under stringent conditions to a polynucleotide consisting of SEQ ID NO:1, 3, 5, 7, 9, 11, 13, 15, 17, 19, 21, 23, 25, 27, 29, 31, 33, 35, 37, or 39 and which encodes a TrpB mutant polypeptide that as an independent subunit catalyze the production of NCAAs or UAAs from an indole or indole derivative and L-serine or L-threonine; or (d) a nucleic acid molecule which hybridizes under stringent conditions to a polynucleotide consisting of SEQ ID NO:1, 3, 5, 7, 9, 11, 13, 15, 17, 19, 21, 23, 25, 27, 29, 31, 33, 35, 37, or 39 and which encodes a polypeptide that comprises the amino acid sequence set forth in SEQ ID NO: 10, 12, 14, 16, 18, 20, 22, 24, 26, 28, 30, 32, 34, 36, 38 or 40.

In one embodiment, an isolated nucleic acid molecule that includes a nucleic acid molecule of the disclosure and a nucleotide sequence encoding a heterologous polypeptide or peptide is provided. For example, a coding sequence for a tag (e.g., a polyHis Tag) can be linked to a polynucleotide of the disclosure.

In general, the disclosure includes any TrpB mutant polypeptide encoded by a modified TrpB polynucleotide derived by mutation, recursive sequence recombination, and/or diversification of the polynucleotide sequences described herein, wherein the polypeptide has novel substrate specificity (e.g., L-threonine), can catalyze a reaction independent of the TrpA subunit using either L-threonine or L-serine and which can produce NCAAs or UAAs.

A nucleic acid molecule of the disclosure, e.g., a nucleic acid molecule that encodes a polypeptide set forth in any of SEQ NOs:2, 4, 6, 8, 10, 12, 14, 16, 18, 20, 22, 24, 26, 28, 30, 32, 34, 36, 38 or 40, or having the nucleotide sequence of set forth in any of SEQ ID NOs:1, 3, 5, 7, 9, 11, 13, 15, 17, 19, 21, 23, 25, 27, 29, 31, 33, 35, 37, or 39, or a portion thereof, can be isolated using standard molecular biology techniques and the sequence information provided herein.

A nucleic acid of the disclosure can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the disclosure comprises a nucleic acid molecule which is a complement of a nucleotide sequence encoding a polypeptide set forth in any of SEQ NOs: 2, 4, 6, 8, 10, 12, 14, 16, 18, 20, 22, 24, 26, 28, 30, 32, 34, 36, 38 or 40. In still another embodiment, an isolated nucleic acid molecule of the disclosure comprises a nucleotide sequence which is at least about 50%, 54%, 55%, 60%, 62%, 65%, 70%, 75%, 78%, 80%, 85%, 86%, 90%, 95%, 97%, 98% or more identical to the nucleotide sequence encoding a polypeptide set forth in any of SEQ NOs: 2, 4, 6, 8, 10, 12, 14, 16, 18, 20, 22, 24, 26, 28, 30, 32, 34, 36, 38 or 40, or having the nucleotide sequence set forth in any of SEQ ID NOs:1, 3, 5, 7, 9, 11, 13, 15, 17, 19, 21, 23, 25, 27, 29, 31, 33, 35, 37, or 39, or a portion of any of these nucleotide sequences.

In another embodiment, an isolated nucleic acid molecule of the disclosure hybridizes under stringent conditions to a nucleic acid molecule consisting the nucleotide sequence encoding a polypeptide set forth in any of SEQ NOs: 2, 4, 6, 8, 10, 12, 14, 16, 18, 20, 22, 24, 26, 28, 30, 32, 34, 36, 38 or 40, or having the nucleotide sequence set forth in any of SEQ ID NOs: 1, 3, 5, 7, 9, 11, 13, 15, 17, 19, 21, 23, 25, 27, 29, 31, 33, 35, 37, or 39. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.) require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of an indole or indole derivative and L-serine or L-threonine to a NCAA or UAA. Further, the term "hybridizes under stringent conditions" is intended to describe conditions for hybridization and washing under which nucleotide sequences at least 60% or greater in homology to each other typically remain hybridized to each other. Preferably, the conditions are such that sequences at least about 70%, more preferably at least about 80%, even more preferably at least about 85% or 90% homologous to each other typically remain hybridized to each other.

The skilled artisan will appreciate that changes can be introduced by mutation into the nucleotide sequences of any nucleic acid sequence encoding a polypeptide set forth in any of SEQ NOs: 2, 4, 6, 8, 10, 12, 14, 16, 18, 20, 22, 24, 26, 28, 30, 32, 34, 36, 38 or 40, or having the nucleotide sequence set forth in any of SEQ ID NOs: 1, 3, 5, 7, 9, 11, 13, 15, 17, 19, 21, 23, 25, 27, 29, 31, 33, 35, 37, or 39, thereby leading to changes in the amino acid sequence of the encoded proteins. In some cases the alteration will lead to altered function of the polypeptide. In other cases the change will not alter the functional ability of the encoded polypeptide.

Also contemplated are those situations where it is desirable to alter the activity of a parent polypeptide such that the polypeptide has new or increased activity on a particular substrate. It is understood that these amino acid substitutions will generally not constitute "conservative" substitutions. Instead, these substitutions constitute non-conservative substitutions introduced into a sequence in order to obtain a new or improved activity. For example, the polypeptides set forth SEQ ID NOs: 10, 12, 14, 16, 18, 20, 22, 24, 26, 28, 30, 32, 34, 36, 38 and 40 describe specific amino acid substitutions that contribute to the alteration of the activity of a parent polypeptide.

It is also understood that an isolated nucleic acid molecule encoding a polypeptide homologous to the polypeptides of SEQ ID NOs: 2, 4, 6, 8, 10, 12, 14, 16, 18, 20, 22, 24, 26, 28, 30, 32, 34, 36, 38, or 40 can be created by introducing one or more nucleotide substitutions, additions, or deletions into the nucleotide sequence encoding the particular polypeptide, such that one or more amino acid substitutions, additions or deletions are introduced into the encoded protein. Mutations can be introduced into the nucleic acid sequence by standard techniques, such as site-directed mutagenesis and PCR-mediated mutagenesis. In contrast to those positions where it may be desirable to make a non-conservative amino acid substitutions (see above), in some positions it is preferable to make conservative amino acid substitutions.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) "Oligonucleotide-directed mutagenesis: a simple method using two oligonucleotide primers and a single-stranded DNA template" Methods in Enzymol. 154: 329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154:350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999) (each of which is incorporated by reference).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181) (each of which is incorporated by reference). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov.

3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter (each of which is incorporated by reference).

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), or the like, into which a nucleic acid sequence of the disclosure has been inserted, in a forward or reverse orientation. In a preferred aspect of this embodiment, the construct further comprises regulatory sequences including, for example, a promoter operably linked to the sequence. Large numbers of suitable vectors and promoters are known to those of skill in the art, and are commercially available.

Accordingly, in other embodiments, vectors that include a nucleic acid molecule of the invention are provided. In other embodiments, host cells transfected with a nucleic acid molecule of the invention, or a vector that includes a nucleic acid molecule of the invention, are provided. Host cells include eucaryotic cells such as yeast cells, insect cells, or animal cells. Host cells also include prokaryotic cells such as bacterial cells.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can be readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used.

Vectors can be employed to transform an appropriate host to permit the host to express a mutant TrpB polypeptide or protein. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*;

mammalian cells such as CHO, COS, BHK, HEK 293 br Bowes melanoma; or plant cells or explants, etc.

In bacterial systems, a number of expression vectors may be selected depending upon the use intended for the mutant TrpB polypeptide. For example, when large quantities of mutant TrpB polypeptide or fragments thereof are needed for commercial production or for induction of antibodies, vectors which direct high-level expression of fusion proteins that are readily purified can be desirable. Such vectors include, but are not limited to, multifunctional *E. coli* cloning and expression vectors such as BLUESCRIPT (Stratagene), in which the mutant TrpB polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the TrpB polypeptides of the invention. For reviews, see Ausubel (supra) and Grant et al. (1987) Methods in Enzymology 153:516-544 (incorporated herein by reference).

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, etc. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

In other embodiments, methods for producing a cell that converts an indole or indole derivative and L-serine or L-threonine to a NCAA or UAA, are provided. Such methods generally include transforming a cell with an isolated nucleic acid molecule (or vector containing the same) encoding a mutant TrpB polypeptide of the disclosure.

In other embodiments, methods for producing NCAAs or UAAs are provided. The methods include: (a) providing a cell containing a nucleic acid construct comprising a nucleotide sequence that encodes a mutant TrpB, (b) culturing the cell in the presence of a suitable indole or indole derivative and L-serine or L-threonine and under conditions where the mutant TrpB is expressed at an effective level; and (c) producing an NCAA or UAA.

In another embodiment, methods of producing NCAAs or UAAs are provided. The method includes (a) providing L-serine or L-threonine, an indole or indole derivative, and a mutant TrpB of the disclosure. Admixing the components for sufficient time and under suitable conditions to produce the NCAA or UAA.

In another embodiment, methods of producing β-methyl-tryptophan or analogs thereof are provided. The method includes (a) providing L-threonine, an indole or indole derivative, and a mutant TrpB of the disclosure. Admixing the components for sufficient time and under suitable conditions to produce the β-methyl-tryptophan or analog. The disclosure provides that indole or derivatives thereof in, for example, the left column below when combined with L-threonine and a mutant TrpB of the disclosure can produce the β-methyl-tryptophan or analog in the corresponding right column.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel") (each of which is incorporated by reference). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564 (each of which is incorporated by reference). Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein (incorporated by reference herein), in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The invention is illustrated in the following examples, which are provided by way of illustration and are not intended to be limiting.

EXAMPLES

Example 1

Figure 3:
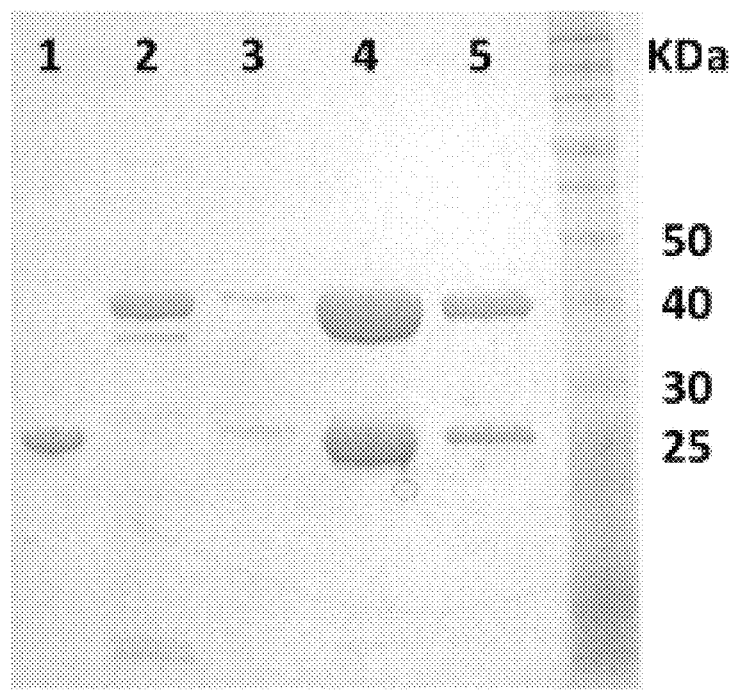
FIG. 3 shows an SDS-PAGE of PfTrpA, PfTrpB, and PfTrpS. 1, PfTrpA, 2, PfTrpB; 3-5, aliquots from 1.5-mL fractions from PfTrpA pull-down using His-tagged PfTrpB; 4-20% gradient, SDS-PAGE. MW from ColorPlus Prestained Protein Ladder (New England Biosystems) is on right.

Cloning, Expression, and Purification of PfTrpA and PfTrpB. The genes encoding PfTrpB (UNIPROT ID Q8U093) and PfTrpA (UNIPROT ID Q8U094) were obtained as gBlocks and cloned into pET22(b)+ for expression in *E. coli* BL21 E. cloni EXPRESS cells (Lucigen). Heterologous protein expression of PfTrpA and PfTrpB was performed in Terrific Broth with 100 µg/mL ampicillin (TBamp) and induced with 500 mM IPTG (final concentration 1 mM). PfTrpB was purified via a HisTrap HP column. PfTrpA was purified via a Q HP HiTrap column (flow-through), followed by ammonium sulfate precipitation, and hydrophobic interaction chromatography on a phenyl Sepharose HP HiTrap column (FIG. 3).

Library Construction and High-Throughput Screening. Error-prone PCR libraries were constructed using standard protocols with either $MnCl_2$ or Mutazyme II (Stratagene). DNA shuffling and site-directed mutagenesis by overlap extension (SOE) PCR were performed to recombine activating mutations. The resulting libraries were cloned into pET22(b)+ with the C-terminal his-tag for expression in *E. coli* BL21 E. cloni EXPRESS cells. High-throughput expression and screening were performed on 96-well scale. Formation of L-tryptophan was recorded at 290 nm.

Kinetics and UV-Vis Spectroscopy. Data were collected between 550 and 250 nm on a UV1800 Shimadzu spectrophotometer (Shimadzu) using 0.25-20 µM of enzyme in 200 mM potassium phosphate (pH 8.0) in a quartz cuvette. Samples were incubated at 75° C. for >3 min to ensure a stable temperature was reached. PfTrpB activity ($k_{cat}$) was measured by monitoring tryptophan formation at 290 nm using $\Delta e290 = 1.89$ $mM^{-1} \cdot cm^{-1}$.

Substrate Selectivity. The relative rate of NCAA production was measured using 20 mM L-serine and 20 mM indole analog (FIG. 4A) in 200 mM potassium phosphate (pH 8.0) with 5% (vol/vol) DMSO. Reactions were incubated at 75° C. for 1 h, quenched, and the relative rate of production formation was measured by comparing the ratio of the product peaks measured via ultra HPLC-MS (UHPLC-MS) Agilent 1290 with 6140 MS detector at 280 nm and then normalizing for the enzyme concentration.

Crystallography. Crystals of PfTrpB and PfTrpS were grown using the sitting drop vapor diffusion method and cryoprotected before diffraction at the Stanford Synchrotron Radiation Laboratories on beamline 12-2. Ligand bound crystals of PfTrpB were prepared by soaking preformed crystals with a concentrated solution of L-Ser or L-Trp. Structures were determined by molecular replacement and models were built using standard procedures.

Identification of Nonnatural Amino Acid Products. Preparative-scale reactions were conducted using $PfTrpB^{0B2}$, which was prepared as a heat-treated lysate. Products were purified directly on C-18 silica, and their identities confirmed by 1H NMR and low-resolution mass spectrometry (LRMS). The optical purity of the products was estimated by derivatization with N-(5-fluoro-2,4-dinitrophenyl)alanamide (FDNP-alanamide).

Selection of the Parent Enzyme, TrpB, from *Pyrococcus furiosus*. A search was performed for an engineering starting point on known thermophilic TrpS enzymes for three reasons: (i) higher operating temperatures afford increased solubility of the hydrophobic substrates, which is useful for preparative reactions; (ii) thermostable enzymes are more tolerant to the introduction of activating but potentially destabilizing mutations; and (iii) thermostable enzyme variants can be screened efficiently. A comparison of published kinetic properties of TrpS from *Thermotoga maritima*, *Thermococcus kodakaraensis*, and *Pyrococcus furiosus* let to the selection of *Pyrococcus furiosus* for its superior kinetic parameters and thermostability (Table 1). PfTrpB heterologously expressed and purified from *E. coli* has a $k_{cat}$ of 0.31 $s^{-1}$ and experiences a 12-fold increase in catalytic efficiency upon addition of purified *P. furiosus* TrpA (PfTrpA) to make the PfTrpS complex (Table 2), similar to values reported previously for *E. coli* TrpB (EcTrpB). Notably, PfTrpB does not show the mechanism-based inactivation that inhibits use of StTrpB for preparation of NCAAs.

TABLE 1

Comparison of TrpB thermophilic enzymes

| Host | $k_{cat}$, $s^{-1}$ | $K_M$, mM L-Ser | $K_M$, µM indole | $k_{cat}$ change with TrpA | Thermal stability indicators |
|---|---|---|---|---|---|
| *Thermotoga maritima* | 4.2 | 110 | 40 | 2.4 | Kinetics measured at 80° C. |

TABLE 1-continued

Comparison of TrpB thermophilic enzymes

| Host | $k_{cat}$, s$^{-1}$ | $K_M$, mM L-Ser | $K_M$, μM indole | $k_{cat}$ change with TrpA | Thermal stability indicators |
|---|---|---|---|---|---|
| Thermococcus kodakarensis | 1.04 ± 0.03 | n/a | 63 ± 5 | 3.3 | 5% activity after 1 h at 80° C. |
| Pyrococcus furiosus | 0.31 ± 0.02 | 1.2 ± 0.1 | 77± 12 | 3.2 | $T_{50}$ = 94.7 ± 1.2 |

Values for PfTrpB are those reported here; the references supply similar data measured by a different group. n/a, not available.

TABLE 2

Biochemical characterization of tryptophan synthases

| Enzyme | Mutations | $k_{cat}$s$^{-1}$ | $K_M$, mM L-serine | $K_M$, μM indole | $k_{cat}/K_M$, mM$^{-1}$s$^{-1}$ indole | $k_{cat}$ change with TrpA* | $T_{50}$, ° C.† |
|---|---|---|---|---|---|---|---|
| PfTrpS | — | 1.0 | 0.6 | 20 | 50 | — | >95 |
| PfTrpB | — | 0.31 | 1.2 | 77 | 4 | 3.2 | 95 |
| PfTrpB$^{2G9}$ | T292S | 1.1 | 0.84 | 14 | 78 | 0.34 | 95 |
| PfTrpB$^{4D11}$ | E17G, I68V, T292S, F274S, T321A | 2.2 | 1.2 | 11 | 200 | 0.3 | 84 |
| PfTrpB$^{0B2}$ | P12L, E17G, I68V, T292S, F274S, T321A | 2.9 | 0.7 | 8.7 | 330 | 0.04 | 87 |

All kinetic data are measured at 75° C. using a previously described (15) continuous assay for Trp production. Additional mutations relative to their parent enzyme are highlighted in bold.
*The effect of PfTrpA was measured by addition of a fivefold stoichiometric excess of PfTrpA under conditions saturating in each substrate.
†T50 is the temperature of half-maximal activity after incubation for 1 h.

Directed Evolution of PfTrpB for Stand-Alone Function. Random mutagenesis was performed by error-prone PCR and a small PfTrpB mutant library (528 clones) was screened for increased Vmax under saturating concentrations of substrate (L-serine and indole). The extreme thermostability of the parent enzyme permitted a 1-h heat treatment of the lysates at high temperature (75° C.) that precipitated the majority of E. coli proteins and ensured that any activated variants retained significant stability. Formation of L-tryptophan took place at 75° C. for up to 1 h (generation 1, 1 h; generations 2 and 3, 6 min). The reactions were then quenched in an ice-water bath, and the production of L-tryptophan was quantified at 290 nm with a plate reader. This procedure identified many activating mutations, with 3.8% (20/528) of the screened variants of generation 1 showing at least 40% greater product formation than the parent. A single mutation, T292S, gave rise to a 3.5-fold increase in $k_{cat}$ compared with PfTrpB, which completely recovered $k_{cat}$ and even exceeded the catalytic efficiency ($k_{cat}$/KM) of the PfTrpS complex (Table 2). Twenty-six other mutations in 19 different variants also contributed activating effects, including W2R, G4C, G4D, ESK, Y10H, P12L, V11A, E13G, E17G, K20E, E21V, E23V, F35S, N35S, Y41C, L59Q, K67I, I68V, M123V, I127S, M144T, L146V, N150T, N166D, Y178C, H180R, Y181C, L182P, D220E, M233V, M233I, N267F, G272D, F274S, F274L, D284E, D284G, T292S, T321A, and T323A.

12 of the most activating mutations identified in the first generation were recombined. Screening a total of 1,408 clones, clone PfTrpB$^{4D11}$ was identified containing mutations E17G, I68V, F274S, T292S, and T321A. The $k_{cat}$ of PfTrpB$^{4D11}$ was 2.2 s$^{-1}$, a seven-fold improvement over wild type (Table 2). PfTrpB$^{4D11}$ served as template for a final round of random mutagenesis, for which 1,144 clones were screened. Clone PfTrpB$^{0B2}$ carried one additional mutation (compared to PfTrpB4D11), P12L, and had a $k_{cat}$ that was 9.4-fold higher than PfTrpB and threefold higher than PfTrpS. PfTrpB0B2 provided an isolated enzyme domain to be as active as in its native complex.

Biochemical Comparison of Evolved PfTrpB Enzymes with PfTrpS. Kinetic analysis of PfTrpB and PfTrpS established that the 12-fold increase in the catalytic efficiency for indole upon complexation is driven by both an increase in $k_{cat}$ and decrease in KM (Table 2). Despite screening the mutant libraries under saturating conditions for both substrates, a steady decrease was observed in the KM for indole in the enzymes with greater activity, which mimics the behavior of the native complex. The KM for L-serine fluctuated during evolution, and in the final round the values for PfTrpB0B2 and PfTrpS were similar.

Figure 1B:
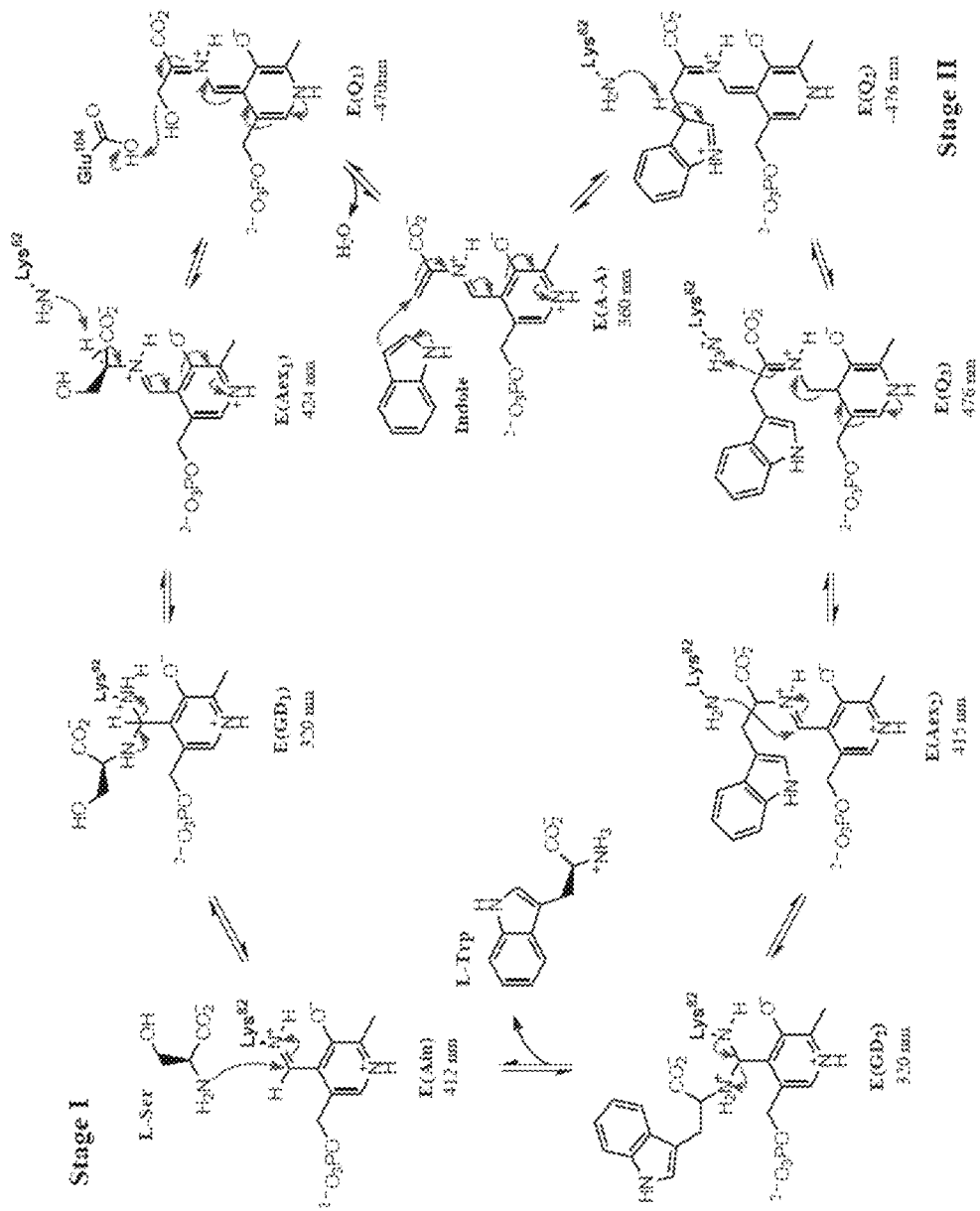
FIG. 1B shows a depiction of the mechanism of the β-replacement reaction in tryptophan synthase divided into α, β-elimination of L-Ser (stage I) and nucleophilic addition of indole (stage II). The wavelengths beneath each intermediate belong to maximum absorbances observed in TrpB from E. coli and S. typhimurium.

Though Michaelis-Menten kinetic analysis provides a simple readout of overall catalytic performance, activity changes upon complex formation and during directed evolution are associated with a shift in the populations of the intermediates in the TrpB catalytic cycle. The PLP cofactor absorbs in the UV-vis region, and different chemical intermediates have characteristic peaks that can be measured readily (FIG. 1B). Under turnover conditions, the recorded spectrum reflects the Boltzmann-weighted average of each of the intermediates in the catalytic cycle. Incubation of PfTrpB with L-serine results in a large increase in absorption at 428 nm, consistent with accumulation of E(Aex1). A peak at 320 nm developed over several minutes, whereas the absorption at 428 nm remained constant, which was attribute to the previously characterized serine deaminase activity that is an artifact of not having a competing nucleophile present. In contrast, L-serine-bound PfTrpS has a λmax near 350 nm, consistent with a shift in the equilibrium to populate the E(A-A). With the engineered proteins, the external aldimine absorbance at 428 nm decreases, and the absorbance bands at 350 nm grow in intensity over the course of directed evolution of Trp synthase activity.

Adding purified PfTrpA to each TrpB variant gave a surprising result: instead of enhancing activity (or doing nothing), PfTrpA inhibited each improved TrpB, an effect that was stronger with each evolutionary step, to the point where PfTrpB0B2 had just 4% of its activity when PfTrpA was added (Table 2).

Structural Analysis of PfTrpB. Whereas the residues that perform the TrpB chemistry are conserved throughout evolution, the conformational motions associated with allosteric signaling have not been characterized outside of StTrpS or in the absence of the α-subunit. A high-resolution structures of wild-type PfTrpB in its ligand-free state, bound to its L-serine substrate, and bound to its L-tryptophan product was obtained (Table 3). Comparison of the ligand-free and Ser-bound structures (at 1.69 Å and 2.0 Å resolution, respectively) reveals motion of the COMM domain into a partially closed state upon serine binding, as well as a hydrogen bond between Asp300 and the Ser-hydroxyl of E(Aex1). This large conformational rearrangement is structurally equivalent to that characterized for StTrpS, with 0.5 Å rmsd between the E(Aex1) forms of TrpB, despite the modest (59%) sequence identity and lack of an α-subunit.

Figure 6A:
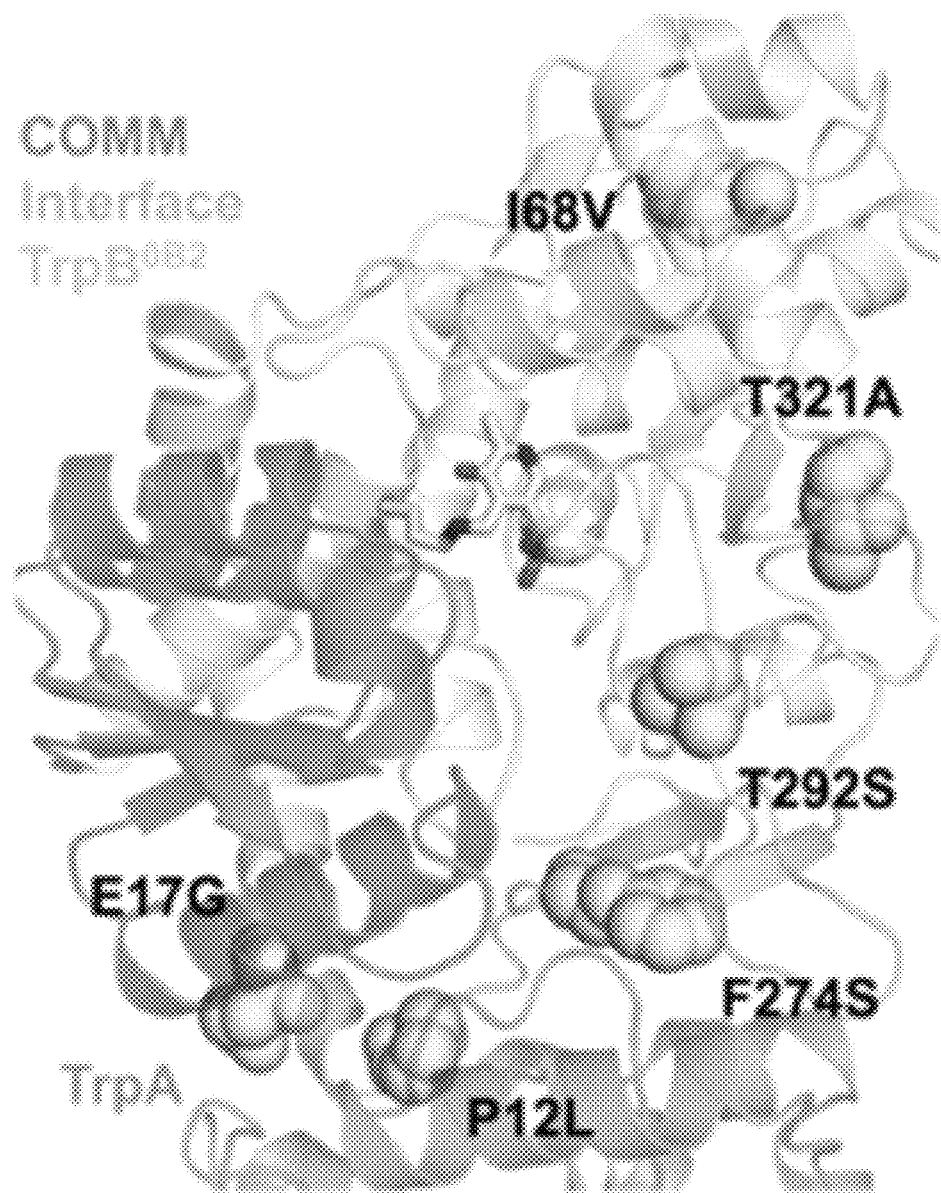
FIG. 6A-D shows distribution of PfTrpB$^{OB2}$ mutations and interaction networks altered by mutational reactivation. (A) PfTrpB residues within 5 Å of PfTrpA and the COMM domain are depicted. (B) A hydrogen bond between D300 and E(Aex1) in the Ser-bound structure (dashes) is formed transiently during the catalytic cycle. When this H-bond is severed, D300 may interact with T292 (no ligands or Trp-bound are depicted). This complex network is centered on a monovalent cation cofactor, shown here as Na+, which is known to mediate allosteric interactions between the α- and β-subunits. (C) Residues F274 and H275 undergo a rotameric shift upon substrate or product binding into an open state. (D) In the closed state (no ligands bound), H275 blocks access to the active site.
Figure 6B:
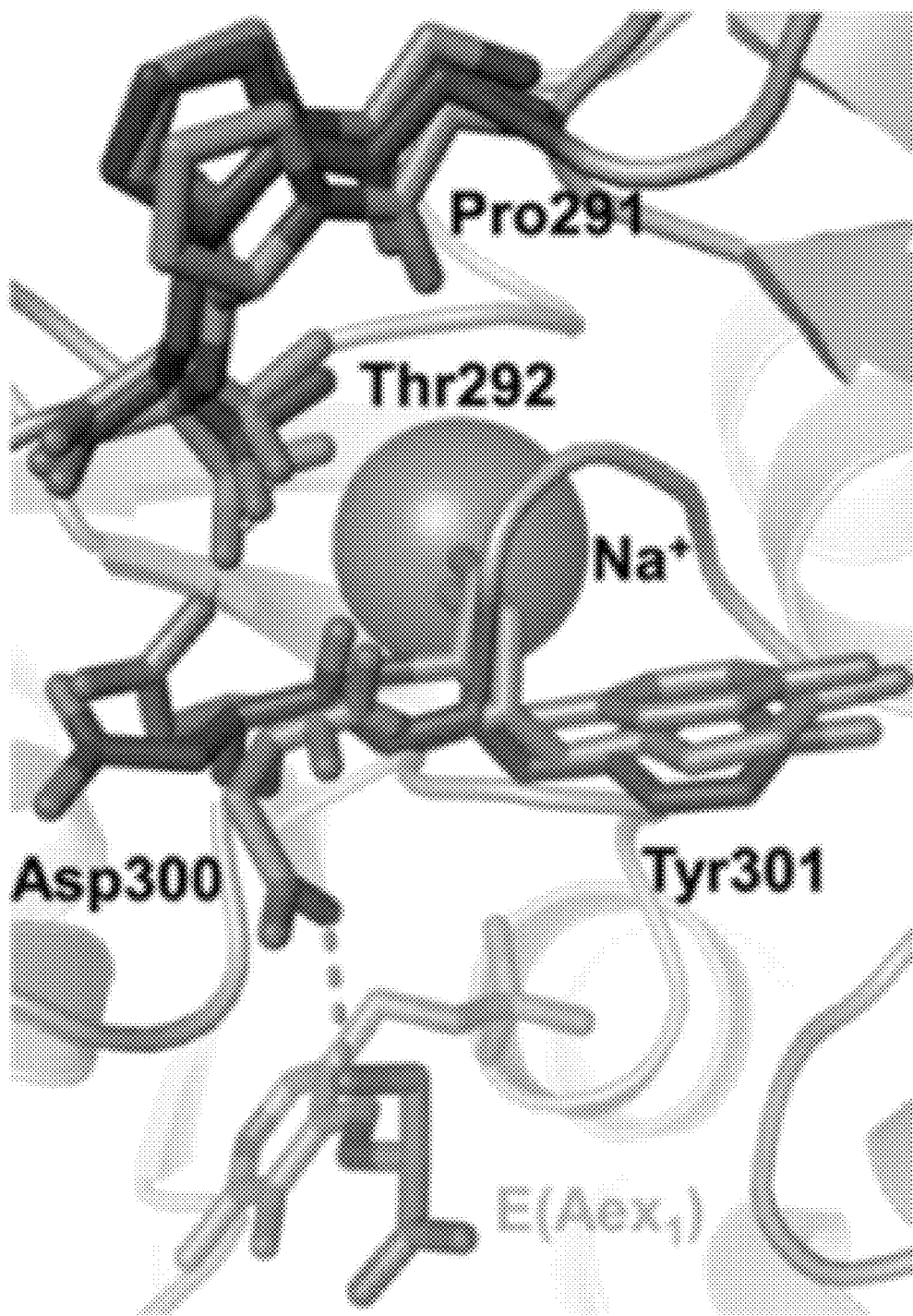
Figure 6C:
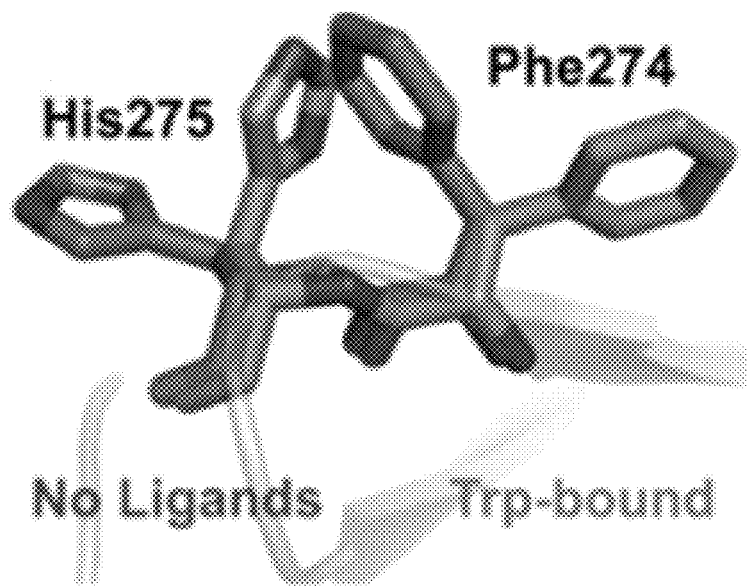
Figure 6D:
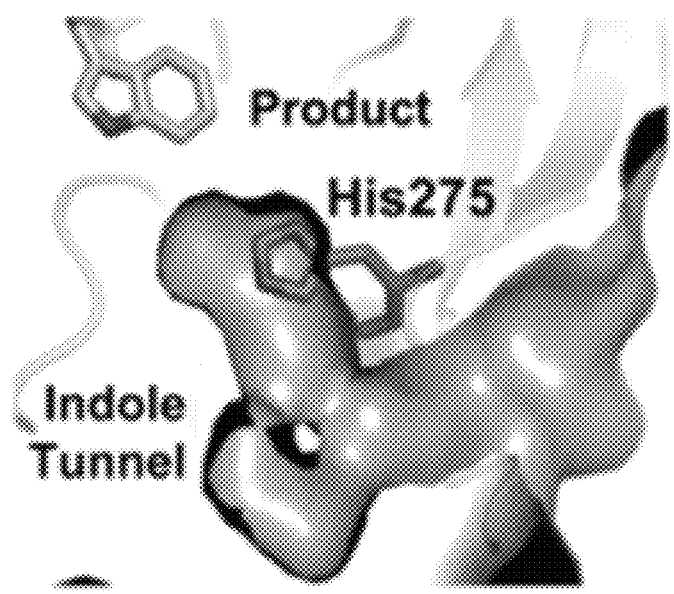

Combined with their similar biochemical properties, this structural conservation constitutes firm experimental support for applying insights gleaned from StTrpS and EcTrpS to the function of PfTrpB. Labeling studies have shown that β-substitution occurs with retention of stereochemistry, indicating the hydroxyl of E(Aex1) must rotate 180° from its crystallographically observed state to eliminate from the same face to which indole is added. The H-bond between E(Aex1) and Asp300 is, therefore, transient during the catalytic cycle and suggests an important role for the H-bond between Thr292 and Asp300 that was observed in the ligand-free structure. Notably, T292S was one of the most activating mutations identified in the first round of directed evolution (Table 2). When L-Ser is incubated with PfTrpB2G9, the UV-vis spectrum clearly shows that the equilibrium is shifted toward E(A-A). It was hypothesized that this mutation alters the energetics of the Asp300-E (Aex1) interaction to favor the fully closed conformational state of the enzyme and thereby accelerate the reaction.

bound structures, a rotameric shift of Phe274 and His275 was observed (FIG. 6C) that may function as a gate within the indole tunnel (FIG. 6D). In the structure of PfTrpS, a hydrogen bond between His275 and Asp43 was observed from the α-subunit, indicating that PfTrpA binding stabilizes this open conformation. In StTrpS, NMR analysis has shown this motion is concerted, and the observation that it is conserved across species is consistent with it having an important role for regulating catalytic function. The location of the F274S mutation is therefore quite striking, because it may alter the energetics of this transition to favor higher activity.

Two mutations, E17G and P12L, map onto the α/β interface of a previously determined 3.0-Å structure of PfTrpS, but this low resolution precluded confident assessment of the side-chain interactions for these residues. A higher-resolution structure was solved at 2.76 Å that revealed a salt bridge between Glu17 of PfTrpB and Arg148 of PfTrpA. Pro12 of PfTrpB is an evolutionarily conserved

TABLE 3

Crystallographic data collection and refinement statistics.

| Protein | PfTrpB | PfTrpB | PfTrpB | PfTrp5 |
|---|---|---|---|---|
| PDH ID code | 5DVZ | 5DW0 | 5OW3 | 5E0K |
| Ligand | None | L-Serine | L-Tryptophan | None |
| Space group | $P2_12_12_1$ | $P2_12_12_1$ | $P2_12_12_1$ | $P2_12_12_1$ |
| Cell dimensions, Å | a,b,c = 87.1, 111.9, 160.8 | a,b,c = 84.2, 109.1, 160.8 | a,b,c = 83.7, 108.9, 160.1 | a,b,c = 87.7, 225.8. 296.2 |
| Cell candles | α = β = γ = 90° | α = β = γ = 90° | α = β = γ = 90° | α = β = γ = 90° |
| Data collection | | | | |
| Wavelength, Å | 0.9795 | 0.9795 | 0.9795 | 0.9795 |
| Beamline | SSRL 12.2 | SSRL 12.2 | SSRL 12.2 | SSRL 12.2 |
| Resolution, Å | 40-1.69 | 40-2.01 | 40-1.74 | 40-2.76 |
| Last bin (4) | (1.72-1.69) | (2.05-2.01) | (1.77-1.74) | (2.81-2.76) |
| No. observations | 865,034 | 942,945 | 1,455,851 | 1,006,477 |
| Completeness (%) | 99.6 (99.9) | 98.0 (67.2) | 98.7 (75.0) | 99.3 (93.7) |
| $R_{pim}$ | 0.050 (0.899) | 0.034 (0.754) | 0.020 (0.752) | 0.082 (1.21) |
| CC(1/2) | 0.995 (0.439) | 0.999 (0.299) | 1.000 (0.425) | 0.990 (0.154) |
| I/σI | 7.3 (0.6) | 15.1 (0.9) | 18.0 (1.0) | 8.0 (0.6) |
| Redundancy | 4.9 (4 9) | 9.8 (5.6) | 9.8 (2.8) | 6.7 (53) |
| Refinement | | | | |
| Total no. of reflections | 161,910 | 91,540 | 140,124 | 142,144 |
| Total no. of atoms | 12,278 | 11,976 | 12,282 | 28,872 |
| Final bin (Å) | (1.73-1.69) | (2.07-2.01) | (1.79-1.74) | (2.83-2.76) |
| $R_{work}$ (%) | 20.2 (39.1) | 17.8 (36.7) | 18.9 (36.1) | 20.4 (37.7) |
| $R_{free}$ (%) | 22.8 (39.0) | 22.1 (36.8) | 22.7 (38.4) | 23.8 (39.2) |
| Average B factor Å$^2$ | 31.8 | 42.7 | 40.5 | |
| Ramachandran plot favored, % | 96.8 | 96.2 | 96.6 | 97.3 |
| Allowed, % | 100 | 100 | 99.9 | 99.8 |
| Outliers, % | 0 | 0 | 0.1 | 0.2 |

Values in parentheses are for the highest-resolution shell. Rmerge is Σ|Io − I|/σIo where Io is the intensity of an individual reflection, and I is the mean intensity for multiply recorded reflections; Rwork is Σ||Fo − Fc||/Fo, where Fo is an observed amplitude, and Fc a calculated amplitude; Rfree is the same statistic calculated over a 5% subset of the data that has not been inducted.

Figure 5A:
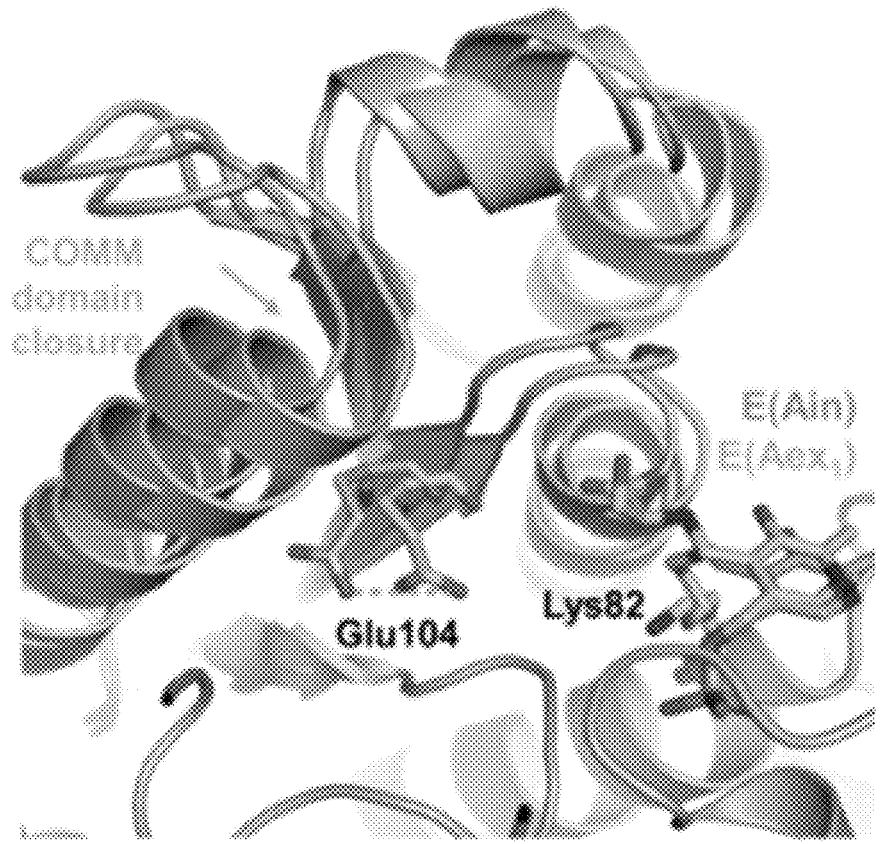
FIG. 5A-C shows structural transitions upon ligand binding in PfTrpB. (A) Superimposition of PfTrpB-E(Ain) and PfTrpB-E(Aex1), respectively. Overlay shows the 2.1-Å displacement of the COMM domain upon E(Aex1) formation. This closure moves the side chain of Glu104 by 3.7 Å, toward its catalytic orientation (dashes). (B) Structure of Ser-bound PfTrpB with a Fo-Fc map of E(Aex1) contoured at 3.0 G. (C) Structure of L-tryptophan-bound PfTrpB with Fo-Fc map of Trp ligand contoured at 3.0 σ.
Figure 5B:
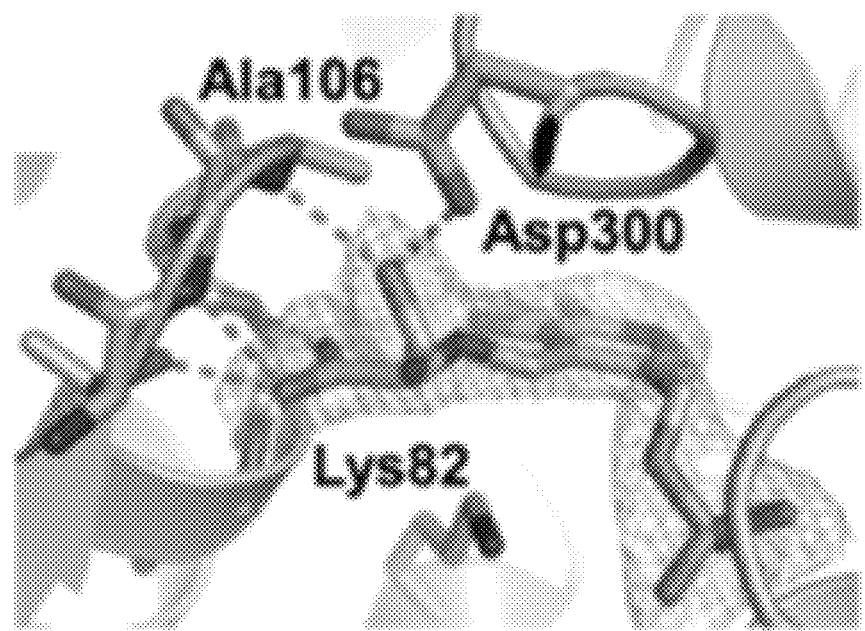
Figure 5C:
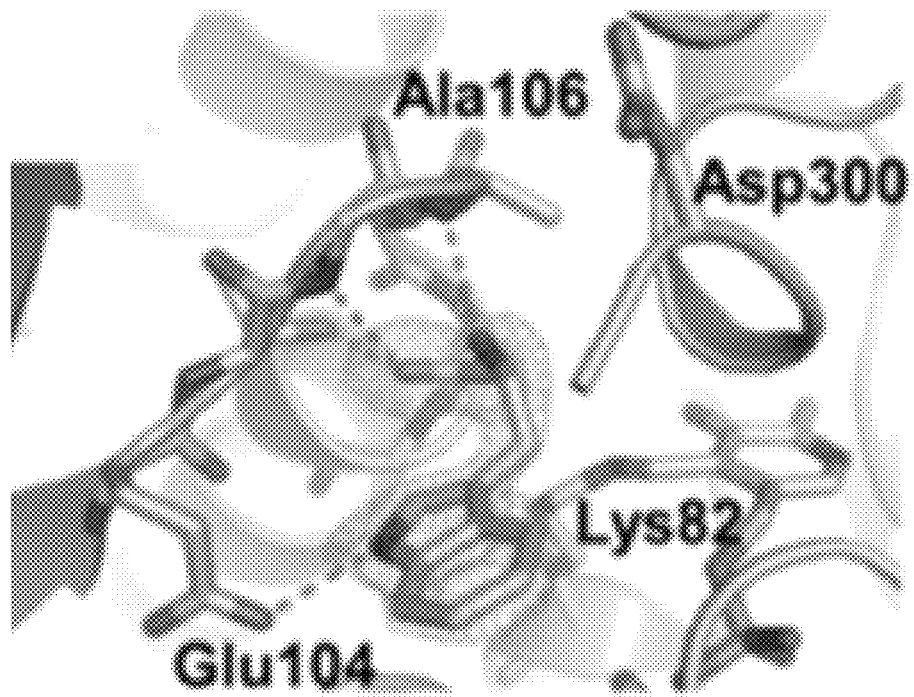

The structure of PfTrpB with L-tryptophan bound in the active site at 1.74 Å resolution shows the product is not covalently linked to the PLP cofactor, but is in a novel ligand-binding pose (FIG. 5C). Residues Thr105 to His110 comprise a carboxylate binding motif that also forms H-bonds to the primary amine of L-tryptophan through the backbone N—H of Ala106. This same residue also H-bonds with the Ser-hydroxyl of E(Aex1). Asp300, however, is not observed to interact with L-tryptophan. A hydrogen bond between Glu104 and the N-1 of L-tryptophan likely also occurs when indole binds. This interaction may serve to increase the nucleophilicity of indole by positioning C-3 close to the acrylate of E(A-A) and by increasing electron density of the arene (FIG. 1B). Glu104 is located in the COMM domain and shifts closer to the active site upon closure (FIG. 5A). In each of the substrate- and product-residue that lies along the indole tunnel between the two subunits, where previous studies have found that mutation to bulkier residues inhibits substrate channeling. Such interactions are clearly disrupted at the α/β interface, but the strong inhibition of PfTrpB0B2 upon PfTrpA addition demonstrates that these proteins still associate. Two mutations present in PfTrpB0B2, I68V and T321A, are distal to sites that undergo an observable structural change upon substrate binding or complex formation, and their contribution to rate enhancement is difficult to rationalize. Overall, 60% of the activating mutations identified through random mutagenesis were located within 5 Å of the α/β interface, the COMM domain, or regions that undergo observable motion upon transition to the closed conformation. These positions comprise just 31% of the protein sequence, indicating modest enrichment within residues in the immediate spatial route between the α/β interface and the β-subunit active site. In contrast to the many mutations that have been identified as deleterious to the allosteric communication in TrpS, the mutations identified here using directed evolution are the first reported to affect allosteric communication and increase the activity of TrpB in isolation.

Figure 4A:
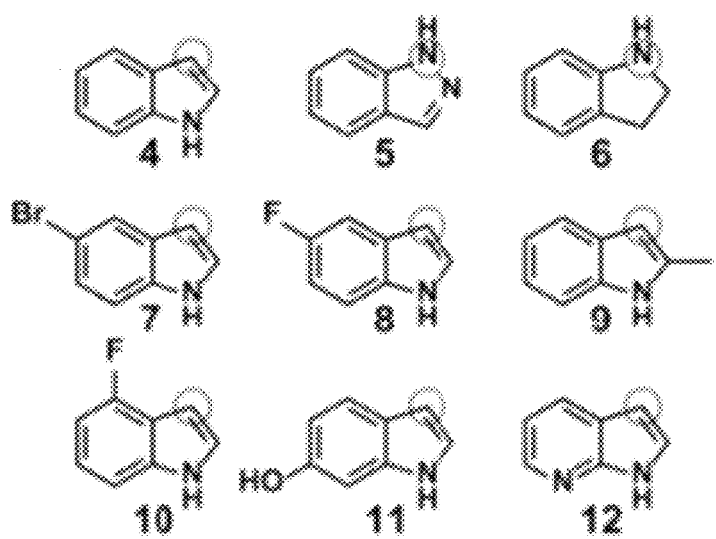
FIG. 4A-B shows substrate profile of native and engineered TrpB enzymes. (A) Indole analogs that have been reported to react with StTrpS were tested for reactivity with the PfTrpB, PfTrpS, and PfTrpB$^{OB2}$ enzymes. The nucleophilic atom is indicated with a gray circle. (B) Relative activities of enzyme complex PfTrpS (black) and PfTrpB$^{OB2}$ (gray) compared with PfTrpB. Reactions performed in duplicate with 20 mM of each substrate and varying enzyme concentrations to ensure incomplete conversion after 1 h. Products were later confirmed in scaled-up reactions using PfTrpB$^{OB2}$.
Figure 4B:
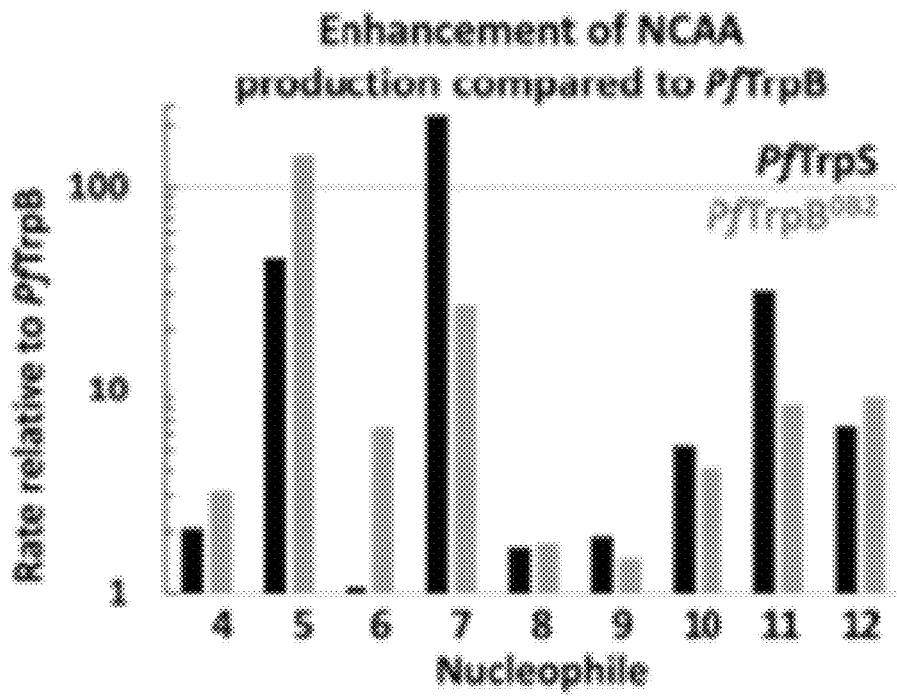

PfTrpB0B2 is a Stand-Alone Catalyst for Production of NCAAs. The selection of TrpB to evolve for high activity outside of its native complex was motivated by practical considerations. Previous studies have shown that StTrpS is a promiscuous enzyme, capable of synthesizing diverse analogs of L-tryptophan. These analogs require subtly different transition state stabilization for catalysis, but the role of allostery in promoting this desirable chemistry has not been studied. A representative panel of substrate analogs was selected to study promiscuous activity in the native and engineered proteins (FIG. 4A). The StTrpS complex reacts with most halogenated and methylated indoles, which only modestly change the steric and electronic properties of the indole ring and afford reactivity at C3. Alternatively, indazole (5) and indoline (6) (see FIG. 4A), which have substantially altered electronic properties, react at N1 for C—N bond formation. The relative rate of PfTrpB compared with PfTrpS was performed and a much larger rate enhancements for TrpB on the indole derivatives than on the native substrate was observed (FIG. 4B), up to a 100-fold increase in the rate of NCAA synthesis with 5-bromoindole (7).

The activity of PfTrpB0B2 was measured on the substrate panel (FIG. 4B) and a substantial increase in activity relative to PfTrpB for all nucleophiles tested was observed. The activity profile is broadly similar to that of PfTrpS, with a few exceptions. The PfTrpS complex reacts approximately eight fold faster than PfTrpB0B2 with bromoindole (7), whereas PfTrpB0B2 reacts approximately six fold faster than PfTrpS with indoline (6) and three fold faster with indazole (5). The identity of each product was confirmed by mass spectrometry and NMR in reactions using PfTrpB0B2. Because the screen was for increases in Vmax during laboratory evolution, the variants selected also have improved expression levels relative to PfTrpB. E. coli cultures produce threefold more soluble and active PfTrpB0B2 than PfTrpB, exceeding 230 mg enzyme per liter culture, facilitating preparative reactions and future use of PfTrpB0B2 as a biocatalyst.

Example 2

Cloning, Expression, and Purification of the Different Orthologs. The genes encoding AfTrpB (UNIPROT ID 028672), TmTrpB (UNIPROT ID P50909) and EcTrpB (UNIPROT ID P0A879) were obtained from IDT and cloned into pET22(b)+ using Gibson Assembly. Protein expression was carried out in *E. coli* BL21 E. cloni Express cells (Lucigen) by inoculating 10-mL Terrific Broth (with 100 µg/mL ampicillin ($TB_{amp}$)) with a single colony and incubated over night at 37° C. and 250 rpm. These overnight cultures were used to scale up to 500-mL $TB_{amp}$ expression cultures, which were grown by shaking at 250 rpm and 37° C. for ~3 h or until an $OD_{600}$ of 0.8 was reached. Then, after chilling the cultures on ice for 20 min, induction was conducted by the addition of IPTG to a final concentration of 1 mM. Induced cultures were allowed to grow at 250 rpm and 20° C. for another 20 h. After centrifugation, pelleted cells were frozen and stored at −20° C. until further use. For protein purification, thawed cells were resuspended in 50 mM potassium phosphate buffer (KPi, pH 8, 20 mM imidazole and 100 mM NaCl (buffer A)), with 200 µM PLP.

Lysis was performed by adding BugBuster (Novagen) and incubating for 15 min at 37° C. Once cells were lysed, they were centrifuged to obtain the soluble protein-rich fraction. In the case of TmTrpB (but not for AfTrpB or EcTrpB), the lysate was then incubated at 75° C. for 20 min and was subjected to another centrifugation step. Afterwards, purification was done using a 1-mL histrap HP column in an AKTA purifier FPLC system (GE Healthcare). A linear gradient was used from buffer A to buffer B (50 mM KPi, pH 8, 500 mM imidazole and 100 mM NaCl) and proteins eluted at approximately 140 mM imidazole. Purified proteins were desalted into 50 mM KPi, pH 8, flash-frozen in liquid N2, and stored at −80° C. until further use.

TmTrpA gene was also obtained from IDT and cloned into pET22(b)+ using Gibson Assembly, but without including the C-terminal His-tag. To obtain TmTrpS, both TmTrpA and TmTrpB were independently expressed in $TB_{amp}$, lysed with BugBuster and incubated at 75° C. Afterwards, an SDS-PAGE gel was run to check purity and concentration ratio and the lysates were mixed using a final ratio of 1:3 (TrpB:TrpA). A further Ni-chromatography step was performed, obtaining TmTrpS with a purity of around 95%, as checked by SDS-PAGE electrophoresis. To check that the complex was present as single species, a purified sample of TmTrpS was run in an analytical size exclusion column (Superdex 200 10/300 GL), yielding a single peak. Protein concentrations were determined via the Bradford assay (Bio-Rad).

Library Construction. For TmTrpB, a recombination library of mutations P14L, P19G, I69V, L274S, and T292S was constructed using site-directed mutagenesis by overlap extension (SOE) PCR. Position 321 was omitted, since $PfTrpB^{OB2}$ contains an alanine residue, the one that is present naturally in TmTrpB. In this library, both the native residue and the mutation were allowed at each of the mentioned positions. The mutagenesis primers encoded the mutations and also the corresponding wild-type sequences. Since positions 14 and 19 are very close, they were included on the same mutagenic primer. This way, six fragments were generated by using Phusion polymerase. The fragments were then DpnI digested, gel purified, and used as template for the subsequent assembly PCR using the flanking primers only. The assembly PCR product was cloned into pET22(b)+ between restriction sites NdeI and XhoI.

For EcTrpB recombination library, the process was analogous and the recombined mutations were P18G, P23G, L73V, Y279S, and S326A. In this case, the omitted position was S297, the corresponding residue to T292 in PfTrpB, since it already contains a serine. At this position, $PfTrpB^{OB2}$ contains the mutation T292S (see Example 1, above). For the EcTrpB site saturation library at position S297, three primers were designed which only differed at the mutagenic position. They contained codons NDT (which encodes for Ile, Asn, Ser, Gly, Asp, Val, Arg, His, Leu, Phe, Tyr, and Cys), VHG (which encodes for Met, Thr, Lys, Glu, Ala, Val, Gln, Pro, and Leu) and TGG (Trp), so that all 20 natural amino acids are included. These three primers were mixed in a 12:9:1 ratio according to the 22c-trick. Then, the SOE PCR was performed as described.

Library Screening. For TmTrpB library screening, BL21 E. cloni Express cells carrying TmTrpB wild type and variant plasmids were grown in 96-well deep well plates in 300 µL $TB_{amp}$ at 37° C. and 80% humidity with shaking at 250 rpm overnight. Then, 630 µL $TB_{amp}$ were inoculated with 20 µL of the overnight cultures and allowed to grow at 37° C. and 80% humidity with shaking at 250 rpm for 3 h. After chilling the cultures on ice for 20 min, ITPG was added to a final concentration of 1 mM. Expression was allowed for another 20 h at 20° C. with shaking at 250 rpm. Cells were then centrifuged at 4,000 g for 10 min and frozen at −20° C. For screening, cells were thawed at room temperature and then subjected to lysis by adding 400 µL/well of 200 mM phosphate buffer, pH 8, with 1 mg/mL lysozyme and 0.05 mg/mL DNaseI for 1 h at 37° C. After centrifugation at 5,000 g for 20 min, a 160-µL aliquot of the lysate was transferred into PCR plates (USA Scientific, Ocala, USA), heat-treated for 1 h at 75° C., and then spun again at 1,000 g and 4° C. for 30 min. After the transfer of 40 µL of lysate to a fresh deep well plate, 160 µL of assay buffer (200 mM phosphate buffer, 200 µM indole, 100 mM L-serine, pH 8) were added. Reaction was allowed to run for 15 min at 75° C. and then stopped after addition of 200 µL of $CH_3CN$.

Figure 7:
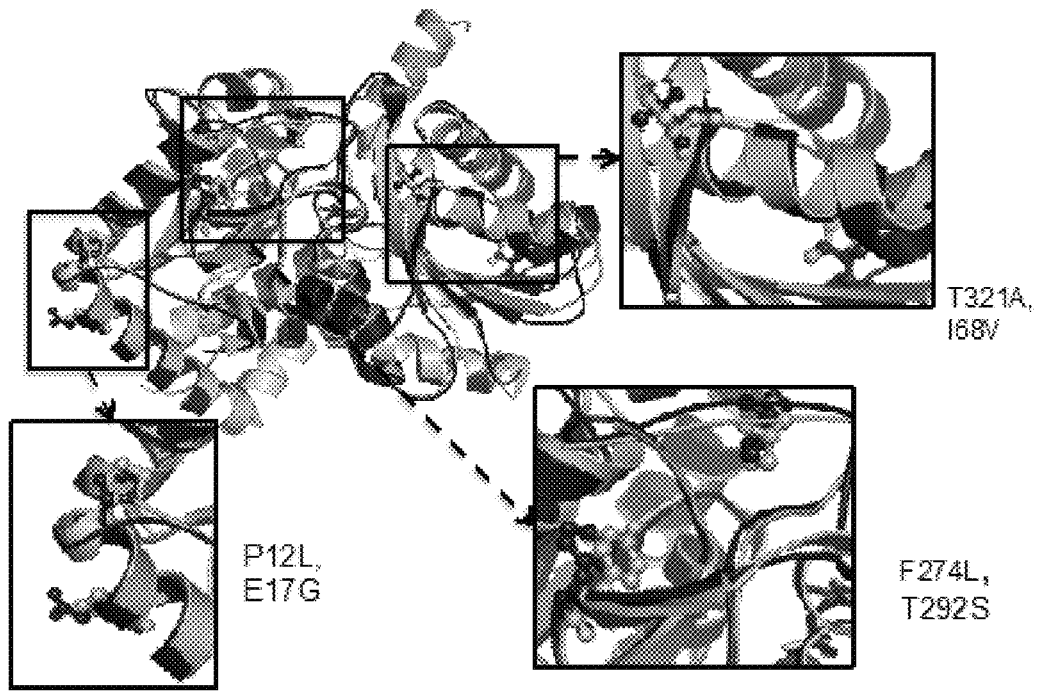
FIG. 7 shows structural alignment of PfTrpB (PDB entry 5DVZ) and EcTrpB (PDB entry 2DH5). The residues mutated in PfTrpB$^{OB2}$ are shown in sticks. To facilitate view, a zoomed detail of the region of the mutations is shown together with a label indicating the mutations.

Based upon the mutations identified in Example 1, experiments were performed to determine if these same/similar mutations could be carried over to other TrpB homologs. A diverse set of TrpB homologs based on a phylogenetic analysis of TrpB: *Archaeoglobus fulgidus* (AfTrpB, 72% sequence identity), *Thermotoga maritima* (TmTrpB, 64%), and *Escherichia coli* (EcTrpB, 57%) were selected. A multiple-sequence alignment with PfTrpB (FIG. 2) showed that several of the residues mutated in PfTrpB$^{OB2}$ (for list of mutations see Table 2) were not conserved among the four homologs, reinforcing the fact that allosteric networks are not well-conserved in evolution, even when activity and structure are conserved (FIG. 7). Indeed, the homologs from Tm and Ec each contained a mutation from PfTrpB$^{OB2}$ in their native sequences (A321 in TmTrpB and S297 in EcTrpB).

The three TrpB homologs and their corresponding 0B2 variants were expressed and purified, and then their kinetic properties ($k_{cat}$ and $K_M$ of indole) were measured. AfTrpB$^{OB2}$ exhibited a 7-fold increase in $k_{cat}$ and a 20-fold increase in $k_{cat}/K_M$ (Table 4, entry 3) compared to wild type (Table 4, entry 4). Notably, this homolog has the highest sequence identity with PfTrpB. Since it was proposed that the 0B2 mutations mimicked the effects of TrpA-binding for PfTrpB, tests were performed to determine whether AfTrpB$^{OB2}$ was being activated through an analogous mechanism. The UV-vis spectra of the enzymes was recorded before and after adding L-serine, relying on the diagnostic spectrum of the PLP cofactor to report the steady state population of the catalytic intermediates. After addition of L-serine, the spectrum of AfTrpB displayed a shift in $\lambda_{max}$ from 412 nm to 428 nm, indicating the formation of the external aldimine with serine, E(Aex$_1$). Conversely, the spectrum of AfTrpB$^{OB2}$ revealed a shift in $\lambda_{max}$ to 350 nm, which corresponds to the amino-acrylate intermediate, E(A-A). This latter spectrum is almost identical to that of AfTrpS, suggesting that the mutations are indeed mimicking the effect of the TrpA-binding and further supporting that the 0B2 mutations have a similar effect in both species.

TABLE 4

Kinetic parameters of the Pf and Af homologs.[a]

| Entry | Enzyme | $k_{cat}$ (s$^{-1}$) | $K_M$ (µM) indole) | $k_{cat}/K_M$ (µM$^{-1}$ s$^{-1}$ indole) |
|---|---|---|---|---|
| 1[b] | PfTrpB$^{OB2}$ | 2.9 | 8.7 | 330 |
| 2 | PfTrpB$^{WT}$ | 0.31 | 77 | 4.0 |
| 3[c] | AfTrpB$^{OB2}$ | 0.51 | 4.8 | 110 |
| 4 | AfTrpB$^{WT}$ | 0.074 | 12 | 6.0 |

[a]Measurement temperatures were 75° C. for Pf and 60° C. for Af.
[b]Contains the mutations P12L, E17G, I68V, F274S, T292S, and S321A.
[c]Contains the mutations (ADD 0B2 mutations)

Figure 8:
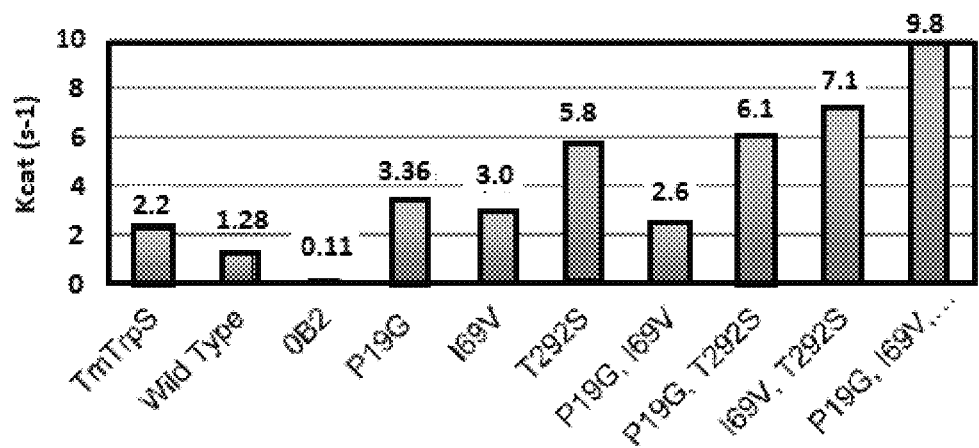
FIG. 8 shows the $k_{cat}$ values of TmTrpS and all TmTrpB studied variants. The mutation is labeled below each bar.
Figure 9:
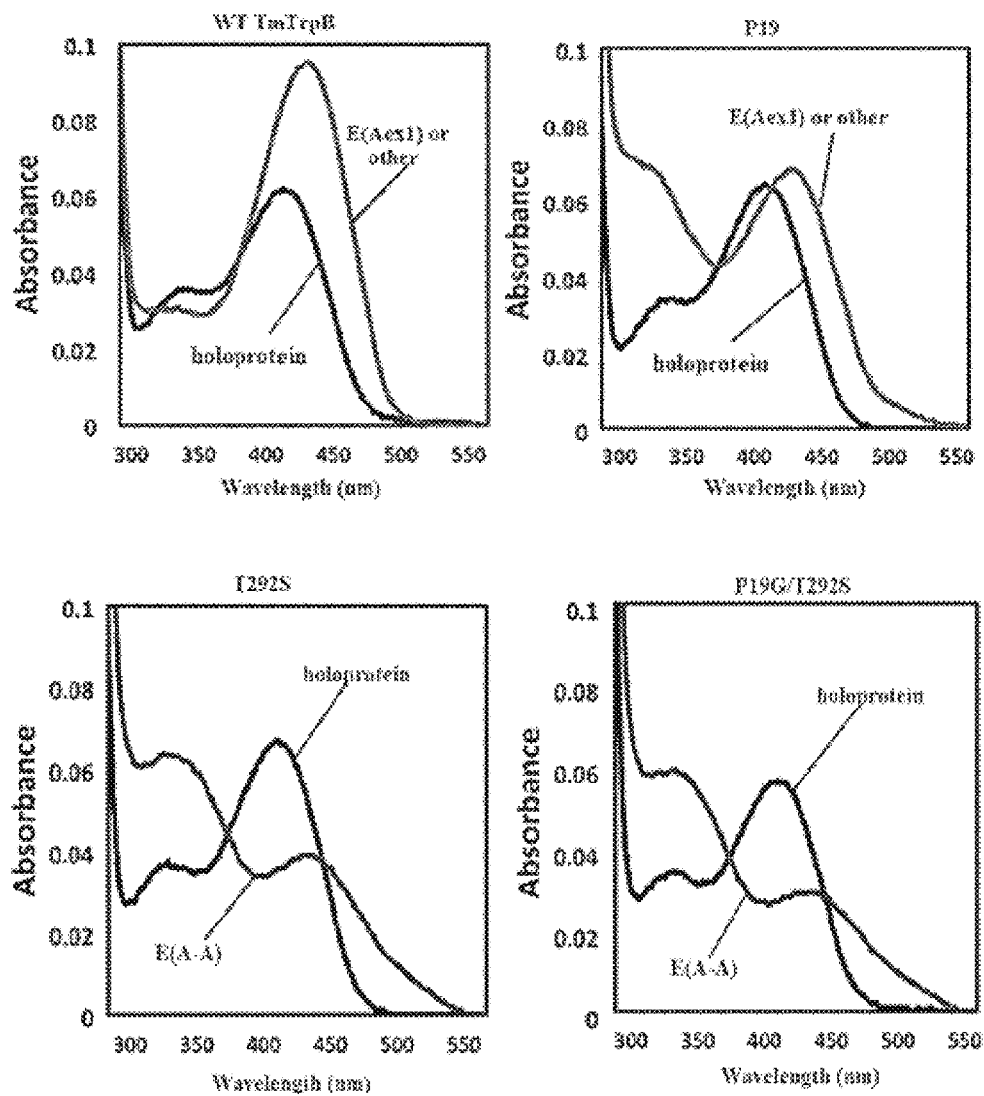
FIG. 9 shows UV-vis spectra of TmTrpS and all TmTrpB studied variants. The mutation is labeled below each graph. Spectra with the holo-protein are represented. To facilitate view, the registered spectra after addition of L-serine are represented when they resemble the E(A-A) characteristic spectrum and either the E(Aex$_1$) or a spectrum not fully equivalent to the E(A-A).
Figure 9:
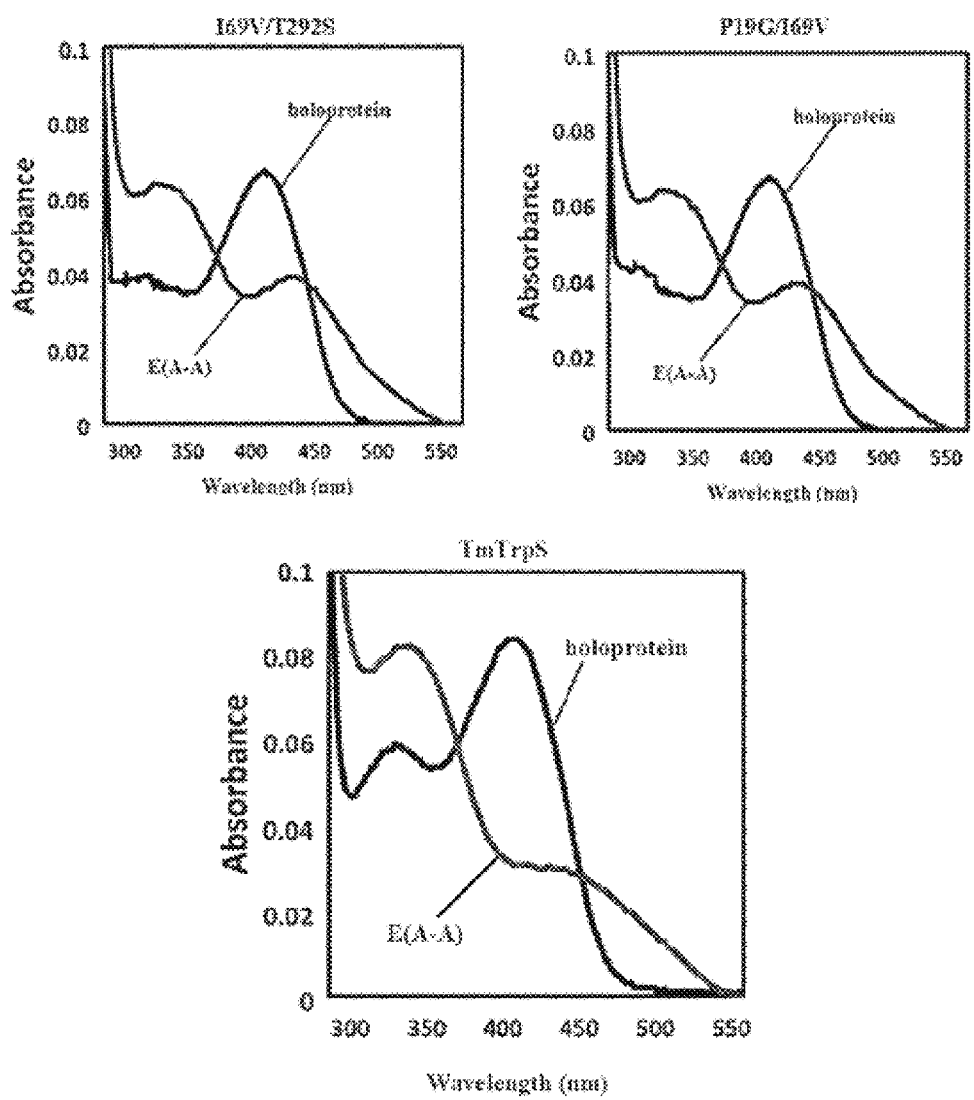

The next homolog, TmTrpB, was examined. This enzyme already contains the 0B2 mutation A321 in its native sequence, but when the other five mutations were incorporated, the $k_{cat}$ was reduced to just 10% of the wild-type activity (Table 5, entries 1 and 2), suggesting that some residues' contributions to allosteric signaling had changed throughout divergent evolution. To investigate whether a subset of the 0B2 mutations would still prove to be activating, or whether the allosteric mechanism had fundamentally changed compared to PfTrpB, a recombination library of the 0B2 mutations in TmTrpB was constructed. Three mutations (P19G, I69V, and T292S) were able to improve activity with respect to wild type. Of these the variant with all three mutations was the most active, with an 8-fold increased $k_{cat}$ and a 10-fold improved $k_{cat}/K_M$ (Table 5, entry 3). Notably, the T292S mutant by itself had a 4-fold increase in $k_{cat}$ and a 6-fold increase in $k_{cat}/K_M$ (Table 5, entry 4). Although all combinations of these mutations led to improved $k_{cat}$ values (FIG. 8) only the variants with T292S gave a UV-vis spectrum with a prominent peak at 350 nm (FIG. 9). The variants without the T292S mutation lacked this probative absorbance peak, but the decrease at 428 nm and concomitant increase at 350 nm are consistent with a similar, though less pronounced activation.

TABLE 5

Kinetic parameters of activated Tm variants. [a]

| Entry | Enzyme | $k_{cat}$ (s$^{-1}$) | $K_M$ (µM) indole) | $k_{cat}/K_M$ (µM$^{-1}$ s$^{-1}$ indole) |
|---|---|---|---|---|
| 1 | TmTrpB$^{OB2}$ [b] | 0.11 | 72 | 2.0 |
| 2 | TmTrpB$^{WT}$ | 1.3 | 33 | 39 |
| 3 | TmTrpB$^{triple}$ [c] | 9.8 | 26 | 380 |
| 4 | TmTrpB$^{T292S}$ | 5.8 | 25 | 230 |
| 5 | TmTrpS | 2.2 | 44 | 50 |

[a] Measurement temperature was 75° C.
[b] Contains the mutations P14L, P19G, I69V, L274S and T292S.
[c] Contains the mutations P19G, I69V, and T292S.

The primacy of the T292S mutation was also observed in Pf, where this mutation restored the $k_{cat}$ of the isolated PfTrpB to that of the PfTrpS complex. In Tm, this single mutation increased the $k_{cat}$ by 3-fold more than TmTrpA binding (Table 5, entry 5). Hence, the same mutations may activate different homologs, but their degree of activation is not conserved.

Mutational activation of the most distant homolog, EcTrpB (57% identity), posed an exceptional challenge. A recombination library of the 0B2 mutations in EcTrpB yielded no variants with enhanced activity and only a few with similar activity as wild type. Notably, the Thr-Ser mutation that has been present in all of the most-active variants was not possible for EcTrpB because a serine is natively present at this position (S297). Other mutations were tested to determine whether they may be activating here, but a site-saturation library confirmed that serine is the optimal residue at that position.

All of the activating mutations for PfTrpB$^{OB2}$ were originally discovered from a library of random PfTrpB mutants. Attention was drawn to the PfTrpB double mutant M144T and N166D; not only is this variant almost as active as PfTrpB$^{T292S}$, but these two residues reside in the region that mediates communication between TrpA and TrpB (the so-called COMM domain). In addition, these residues are almost universally conserved. It was hypothesized that the effects of mutational perturbation at these sites might be conserved throughout evolution as well. Thus, these were transferred into the three homologs and were pleased to see that all variants showed higher $k_{cat}$ values than wild type (Table 6).

Once again, the degree of activation was different for each of the homologs, as reflected in their kinetics and the steady state distribution of intermediates upon addition of L-serine. In particular, the double mutant Pf, Af, and EcTrpB enzymes still accumulated the $E(Aex_1)$ intermediate but mutation of the TmTrpB enzyme, which natively accumulates a mixed population of $E(Aex_1)$ and $E(A-A)$, completely shifts the spectrum such that it shows the characteristic amino-acrylate signal. These data suggest that this double mutation ($TmTrpB^{M145T\ N167D}$) is also activating the enzyme through allosteric mimicry, and that these effects are conserved throughout evolution.

TABLE 6

Kinetic parameters of homologous double mutants.[a]

| Entry | Enzyme | $k_{cat}$ ($s^{-1}$) | $K_M$ (μM indole) | $k_{cat}/K_M$ (μM$^{-1}$ s$^{-1}$ indole) |
| --- | --- | --- | --- | --- |
| 1 | PfTrpB$^{M144T\ N166T}$ | 0.83 | 42 | 20 |
| 2 | AfTrpB$^{M156T\ N178T}$ | 0.34 | 11 | 31 |
| 3 | TmTrpB$^{M145T\ N167T}$ | 3.3 | 32 | 100 |
| 4 | EcTrpB$^{M149T\ N171T}$ | 0.34 | 18 | 19 |

[a] Measurements temperatures were 75° C. for Pf and Tm, 60° C. for Af, and 37° C. for Ec.

Screens of these variants against challenging substrates were performed to identify variants with activity greater than PfTrpB$^{0B2}$ that could serve as parents for further evolution. Halogenated tryptophan derivatives comprise a product class of particular interest was used. Not only can halogens have a tremendous effect on a compound's properties, such as biological activity, but they can also serve as handles for further diversification through cross-coupling. Halotryptophans are also useful tools for chemical biology because they can probe structural features like n-cation interactions and serve as fluorophores to facilitate the study of protein dynamics. As such, the use of TrpS to synthesize halotryptophans has been investigated extensively. In previous studies, however, substitution at the 5-position of indole with anything larger than fluorine led to a dramatic decrease in reactivity. The panel of stand-alone TrpB enzymes was screened for activity on 5-haloindoles (6, Scheme 1) and observed that TmTrpB$^{M145T\ N167D}$ showed unusually high activity in the formation of the corresponding tryptophan derivatives (7, Scheme 1). Thus one can access 5-chloro and 5-bromotryptophan in 75% or greater yields.

Scheme 1.
Biocatalytic synthesis of 5-halotryptophans using TmTrpB$^{M145T\ N167T}$.

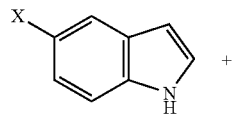

6a, X = Br
b, X = Cl

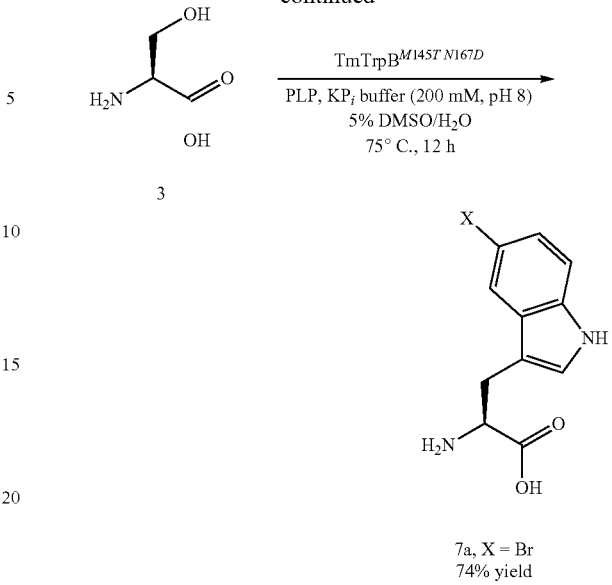

7a, X = Br
74% yield
7b, X = Cl
94% yield

Example 3

General. Chemicals and reagents were purchased from commercial suppliers (Sigma-Aldrich, VWR, Chem-Impex International, Alfa Aesar) and used without further purification unless otherwise noted. Multitron shakers (Infors) were used for cell growth. UV-vis spectra were collected on a UV1800 Shimadzu spectrophotometer (Shimadzu). LC-MS data were collected on an Agilent 1290 UHPLC with 6140 MS detector (Agilent Technologies).

Cloning, expression, and purification of PfTrpB. The gene encoding PfTrpB (UNIPROT ID Q8U093) was previously codon-optimized for Escherichia coli and cloned into pET22(b)+ with a C-terminal his6-tag. Expression and purification protocols for the new variants reported here were analogous to those described above. Briefly, a single colony of E. coli BL21 E. cloni Express cells (Lucigen) harboring the PfTrpB plasmid was used to inoculate a 5 mL culture of Terrific Broth with 100 μg/mL ampicillin (TB$_{amp}$) and incubated over night at 37° C. and 250 rpm. This culture was used to inoculate a 500-mL TB$_{amp}$ expression cultures, which was incubated 250 rpm and 37° C. for ~3 h or until an OD$_{600}$ of 0.8 was reached. Cultures were chilled on ice for 20 min and expression was induced by the addition of 500 mM isopropyl β-D-thiogalactopyranoside (IPTG) to a final concentration of 1 mM and continued to grow at 250 rpm and 20° C. for another 20 h. Cells were harvested at 4° C. and 5000 g for 10 min; the pellets were frozen at −20° C. until further use.

For preparation as a heat treated lysate, frozen cell pellets were thawed at room temperature and resuspended in 50 mM potassium phosphate buffer, pH 8.0, with 200 μM PLP, 1 mg/mL Hen egg white lysozyme, and 0.02 mg/mL DNAse. After vortexing, cells were lysed with BugBuster (Novagen) according to the manufacturer's recommendations, and the cleared lysates were centrifuged at 20,000 g and 4° C. for 10 min. The lysate was then incubated at 75° C. for 10 min, centrifuged again as described above and buffer exchanged into 50 mM potassium phosphate buffer pH 8.0, snap-frozen in liquid N2 and stored at −80° C. until further use.

For purification, frozen cell pellets where thawed and treated as above with modification of the lysis buffer: 50 mM phosphate buffer, pH 8, with 20 mM imidazole and 100 mM NaCl (buffer A), with 200 µM PLP. The heat-treated lysate was applied to a 1-mL histrap HP column. The purification was performed with an AKTA purifier FPLC system (GE Healthcare). PfTrpB eluted during a linear gradient from buffer A to buffer B (50 mM phosphate buffer with 500 mM imidazole and 100 mM NaCl, pH 8) at 140 mM imidazole. Purified PfTrpB was desalted into 50 mM phosphate buffer, pH 8, frozen in liquid N2, and store at −80° C. until further use.

Purified protein concentrations were determined via the Bradford assay (Bio-Rad). The concentration of PfTrpB$^{2B9}$ in heat treated lysates was determined by specific activity. Tryptophan formation was monitored at 75° C. over 1 min at 290 nm using $\Delta\varepsilon_{290}=1.89$ mM$^{-1}$ cm$^{-1}$.[2] The assay buffer contained 200 mM potassium phosphate pH 8, and 5 µM PLP. Using purified PfTrpB$^{2B9}$, we recorded an activity of 0.9 s$^{-1}$ with 400 µM Ind and 20 mM Ser. Using this parameter, 375 mg L$^{-1}$ of PfTrpB$^{2B9}$ active catalyst were prepared as a heat-treated lysate.

Library Construction. The error-prone PCR library was constructed with 200, 300 and 400 µM MnCl$_2$ as the mutagen using the gene for PfTrpB$^{4D11}$ as the parent. The recombination library of hits found from the random mutagenesis studies (I16V, Q89L, F95L, L182P, Y192H, and V384A) was constructed using site-directed mutagenesis by overlap extension (SOE) PCR. The library was constructed from fragments that were DpnI digested, gel purified, and used as template for the subsequent assembly PCR using the flanking primers only. The assembly PCR product served as template for a second round of PCRs generating the fragments carrying the remaining mutations, followed by the same procedure as described above. Each library was cloned into pET22(b)+ between restriction sites NdeI and XhoI in frame with the C-terminal his-tag for expression in E. coli BL21 E. cloni Express cells.

High-Throughput Screening. For high-throughput expression, BL21 E. cloni Express cells carrying PfTrpB$^{4D11}$ and variant plasmids were grown in 96-well deep well plates in 300 µL TB$_{amp}$ at 37° C. and 80% humidity with shaking at 250 rpm overnight. TB$_{amp}$ expression cultures (630 µL) were inoculated with 20 µL of the overnight cultures and continued to grow at 37° C. and 80% humidity with shaking at 250 rpm for 3 h. Expression was induced with the addition of ITPG to a final concentration of 1 mM to pre-chilled (20 min on ice-water bath) cultures. The expression continued for another 20 h at 20° C. with shaking at 250 rpm. Cells were then centrifuged at 4000 g for 10 min and frozen at −20° C. over night. For screening, cells were allowed to thaw at room temperature and then lysed in buffer consisting of 200 mM phosphate buffer, pH 8, with 1 mg/mL lysozyme and 0.05 mg/mL DNaseI. To increase the enzyme concentration, 350 µL/well was used for the error-prone library and 400 µL/well was used for the recombination library. Cells were lysed via incubation 37° C. for 1 h. After centrifugation at 5000 g for 20 min, a 180-µL aliquot of the lysate (160-µL aliquot for recombination) was transferred into PCR plates (USA Scientific, Ocala, USA), heat-treated for 1 h at 75° C., and then spun again at 1,000 g and 4° C. for 30 min. After the addition of 120-µL assay buffer (200 mM phosphate buffer, 20 mM indole, 0.75 mM L-threonine, pH 8) to 80 µL of cleared, heat-treated lysates in UV-transparent assay plates (Evergreen Scientific), the plates were sealed and formation of β-MeTrp took place at 75° C. for up to 45 min (generation 1: 30 min, generation 2: 45 min). The reactions were then arrested by incubation in an ice-water bath, and the amount of β-MeTrp formed was recorded at 290 nm with a plate reader (Tecan Infinite M200).

Low enzyme activity in the first generation led to a relatively high error in the assay (CV 50%) and only the nine hits with activity 2.5-fold greater than parent were selected for subsequent sequencing and rescreening. One of the hits was revealed to be the parent sequence and three contained only silent mutations. Cultures of each hit containing missense mutations were grown in triplicate on 5 mL scale and expression and lysis proceeded in the same manner as described in the Cloning, Expression and Purification section above. Reactions using 10 µM protein as heat-treated lysate (determined by Bradford assay) and 20 mM each substrate were run for 1 h at 75° C. and quenched by dilution to 50% ACN. Samples were analyzed by quantitation of product on HPLC and the increase in activity relative to parent are shown in Table 7.

TABLE 7

Activity of hits from random mutagenesis library relative to parent

| Variant | Fold Improvement | Mutations |
|---|---|---|
| PfTrpB$^{4D11}$ | 1.0 (parent) | |
| PfTrpB$^{3C7}$ | 1.5 | I16V, Q89L |
| PfTrpB$^{4H5}$ | 0.9 | L182P |
| PfTrpB$^{4G1}$ | 2.4 | F95L |
| PfTrpB$^{4E9}$ | 1.2 | V384A |
| PfTrpB$^{2A9}$ | 1.3 | Y192H |

Improvement measured as increase in β-MeTrp formation after 60 min reaction at 75° C.

For the second generation, each of the silent mutations identified through error-prone were added to the PfTrpB$^{4D11}$ plasmid and the resultant construct was found to have higher expression under the growth conditions of the high-throughput screen, but not when grown at larger scale in a shaking flask. Nonetheless, this construct was used as the parent for the recombination libraries (described above) which were screened under similar conditions as the random mutagenesis libraries. Many potentially activated proteins were identified from the recombination library but rescreening the top five hits showed only a single protein, PfTrpB$^{2B9}$ had activity that was greater than the most active variant from the random mutagenesis library (Table 8).

TABLE 8

Activity of hits from recombination library relative to parent

| Variant | Fold Improvement | Mutations |
|---|---|---|
| PfTrpB$^{4G1}$ | 1.0 (parent) | F95L |
| PfTrpB$^{1B5}$ | 0.3 | I16V, F95L, L182P, V384A |
| PfTrpB$^{1F4}$ | 0.8 | I16V, F95L, Y192H, V384A |
| PfTrpB$^{3H2}$ | <0.01 | I16V, A93V, F95L, Y192H, V384A |
| PfTrpB$^{1E4}$ | <0.01 | I16V, Q89L, F95L, L182P, V384A |
| PfTrpB$^{2B9}$ | 1.7 | I16V, F95L, V384A |

Improvement measured as increase in β-MeTrp formation after 90 min reaction at 75° C.

UV-Vis Spectroscopy. Spectra were collected between 550 and 250 nm on a UV1800 Shimadzu spectrophotometer (Shimadzu) using 20 µM of enzyme in 200 mM potassium phosphate pH 8.0 in a quartz cuvette. Samples were incubated at 75° C. for >3 min to ensure a stable temperature was reached. Stage I of the reaction was initiated by addition of 20 mM L-threonine, and the spectra were measured in <15 s to limit production of α-ketobutyrate from deamination of L-threonine, which absorbs at 320 nm.

Total Turnover Number (TTN) Determination. Measurements were made using HPLC and LC-MS instruments. The amount of Trp formed was measured at 280 nm using a standard curve with trichlorobenzene as internal standard. Measurement of the UV-absorption spectrum of β-MeTrp showed an identical spectrum (Figure SN), and the same curve employed for both products while determining the TTN for the catalysts engineered for activity with Ser. Later, it was found that the conversion could be measured by monitoring at 277 nm, the isosbestic point for the conversion of indole to L-Trp or β-MeTrp, and calculating the ratio of product peak to the sum of the substrate and product peaks. This method is insensitive to loading volume and results agreed with measurements using a standard curve. This method of TTN determination is accurate when there are no competing reactions with indole or product, which was observed for the conditions employed here. This same technique was used to determine the TTN of the PfTrpB$^{2B9}$ reaction with different nucleophiles. The isosbestic point for the conversion of substrate to product was measured using a time course UV-vis analysis of the reaction catalyzed by PfTrpB$^{2B9}$ using L-Ser as the amino acid source because the reactions are significantly faster than with L-Thr and the β-Me group does not change the absorbance spectrum of the product (Table 9). Reactions were set up in triplicate using a total volume of 150 μL with 25 mM nucleophile and 250 mM L-Thr in 200 mM potassium phosphate pH 8.0 in borosilicate glass vials, as plastics can absorb indoles at high temperatures. Before addition of enzyme, all reagents were transferred into a Coy anaerobic chamber with <1 ppm $O_2$ to rapidly exchange the atmosphere in the headspace of the vials to 95/5% $N_2/H_2$, which limits competing non-catalytic oxidation of indoles. Enzyme was added in the anaerobic environment with varied catalyst loading to ensure a robust product signal in subsequent analysis. Reaction vessels were capped before being removed from the anaerobic chamber and incubated in a 75° C. water bath for 24 hours. Reactions were quenched the next day by addition of 1 volume (150 μL) of 100% ACN, mixing, and allowing to rest at room temperature for 10 min. Quenched solutions were then diluted 5-fold with 40% ACN in water and analyzed via LC-MS. In all cases, auxiliary peaks that would indicate non-catalytic degradation of substrate were present at only low levels, contributing to <1% of the total integration signal for a given wavelength. For 7-azaindole, a second peak with m/z=220 was observed that was also found in larger scale reactions and whose properties are consistent with an N-alkylated product.

TABLE 9

TTN of β-substitution reaction with L-Thr with different nucleophiles

| Nucleophile | Isosbestic Point (nm) | Catalyst Loading (%) | TTN |
|---|---|---|---|
| Indole | 277 | 0.01 | 8200 ± 1600 |
| 2-Methylindole | 279 | 0.01 | 6400 ± 1400 |
| 6-Methylindole | 273 | 0.01 | 1100 ± 100 |
| 4-Fluoroindole | 267 | 0.1 | 378 ± 8 |
| 5-Fluoroindole | 282 | 0.01 | 1300 ± 280 |
| Indazole | 276 | 0.04 | 500 ± 40 |
| 7-Azaindole | 292 | 0.1 | C-alkylation - 220 ± 40<br>N-alkylation - 32 ± 3 |

Activity measured via LC-MS and conversion as the ratio of substrate to total peak intensity at the isosbestic point after 24 hour reaction at 75° C.

Protein Crystallography. Identification of PfTrpB crystallization conditions are described above, and crystals routinely grown in as sitting drops against a 1 mL reservoir of 15-25% PEG3350 and 0.1 M Na HEPES pH 7.85 with mother liquor comprised of 1.5 μL of 8.0 mg/mL PfTrpB and 1.5 μL of well solution. Ligand-bound structures were determined by soaking crystals of PfTrpB with 100 mM L-threonine for 2 min. Crystals were cryo-protected through oil immersion in Fomblin Y (Sigma) and flash frozen in liquid N2 until diffraction. Diffraction data were collected remotely at the Stanford Synchrotron Radiation Laboratories on beamline 12-2. Crystals routinely diffracted at or below 2.0 Å and the data were integrated and scaled using XDS and AIMLESS. A resolution cutoff of CC1/2>0.3 was applied along the strongest axis of diffraction. These data contributed to model quality as judged by $R_{free}$ in the final bin <0.4. The structure was solved using molecular replacement with PHASER, as implemented in CCP4. The search model comprised a single monomer of PfTrpB (PDB ID: 5DW3) subjected to 10 cycles of geometric idealization in Refmac5 and removal of all ligands. Model building was performed in Coot beginning with data processed at 2.4 Å, followed by subsequent inclusion of increasingly higher resolution shells of data with relaxed geometric constraints. Refinement was performed using REFMAC5. The MolProbity server was used to identify rotamer flips and to identify clashes. After the protein, ligand, and solvent atoms were built TLS operators were added to refinement, which resulted in substantial improvements in $R_{free}$ for the models. The structure is deposited with PDB ID: 5IXJ (incorporated herein by reference).

Identification β-Methyl Amino Acid Products. The identities of the amino acid products were confirmed by $^1$H NMR and high-resolution mass spectrometry (HRMS). Proton NMR spectra were recorded on a Varian 300 MHz or Brucker 400 MHz spectrometer. Proton chemical shifts are reported in ppm (δ) relative to tetramethylsilane and calibrated using the residual solvent resonance (DMSO, δ 2.50 ppm; $CD_3OD$, δ 3.31 ppm; $D_2O$, δ 4.79 ppm). Data are reported as follows: chemical shift (multiplicity [singlet (s), doublet (d), doublet of doublets (dd), doublet of doublets of doublets (ddd), triplet (t), triplet of doublets (td)], coupling constants [Hz], integration). Fluorine NMR spectra were recorded on a 300 MHz (282 MHz) spectrometer without proton decoupling. Fluorine chemical shifts are reported in ppm relative to $FCCl_3$ (δ 0.00 ppm) and were calibrated automatically by the spectrometer using the solvent deuterium lock signal. High-resolution mass spectra were obtained using fast atom bombardment JMS-600H High Resolution Mass Spectrometer (JEOL).

Reaction with Heat-Treated Lysate: Reactions were conducted using PfTrpB$^{2B9}$, which was prepared by heat-treatment as described above. The protein was used as a solution in potassium phosphate buffer (50 mM, pH 8.0) and the concentration varied between preps between 97 μM and 670 μM, as determined by specific activity. Threonine was added as a solid and PLP was used as a 15 mM aqueous solution.

Generally, reactions were conducted in 2-3 mL volume with the following reagents added sequentially: 0.1 M indole analog, 1.0 M threonine, 0.2 M potassium phosphate buffer pH 8.0 with 5% dimethyl sulfoxide, and a five-fold molar excess of PLP to enzyme. Finally, the enzyme solution was added and the vial was capped and immersed in a water bath that had been equilibrated to 75° C. After 16-24 h, the reaction mixture was allowed to cool to room temperature, then purified directly on C-18 silica (20 mL column volume) using a Isolera automated column instrument (Biotage) with 0% to 100% acetonitrile/H$_2$O.

To identify the best parent enzyme for optimization, we first measured production of β-MeTrp using purified enzymes from each generation in the evolution if PfTrpB$^{OB2}$. Wild-type PfTrpB was an inefficient catalyst, performing just 66 turnovers in 24 hours (Table 10, entry 1). This activity was enhanced approximately 6-fold with the single point mutation T292S (Table 10, entry 2), and further to ~420 TTN with the enzyme PfTrpB$^{4D11}$ (Table 10, entry 3), which incorporates four additional mutations. However, PfTrpB$^{OB2}$, which has higher Trp synthase activity than PfTrpB$^{4D11}$ exhibited a decrease in activity (Table 10, entry 4) and we therefore selected PfTrpB$^{4D11}$ as the parent for subsequent evolution.

TABLE 10

Total turnovers catalyzed by TrpB enzymes prior to evolution for activity with L-threonine.

| Entry | Enzyme | Turnovers |
|---|---|---|
| 1 | PfTrpB$^{WT}$ | 66 |
| 2 | PfTrpB$^{T292S}$ | 420 |
| 3 | PfTrpB$^{4D11}$ | 660 |
| 4 | PfTrpB2$^{180}$ | |

Activity measured using 1 μM purified enzyme in 0.2 M potassium phosphate buffer pH 8.0 with 20 mM of each reactant, L-threonine and indole, with a 24 h reaction at 75° C.

Previous studies have shown that the catalytic activity of TrpB is governed by open-close transitions of the communication (COMM) domain, and mutations that alter this dynamic in the reactivated subunits are distributed throughout the protein structure. As such, random mutagenesis was applied for the first round of evolution for activity on Thr. To determine an optimal mutational load, the retention of function of 352 clones was measured with different mutation rates. In this process, six missense mutations were identified in five clones with at least a 2-fold increase in V$_{max}$, obviating the need for screening a more expansive library. The most active clone from this library, PfTrpB$^{4G1}$, increased activity ~3.8-fold and contained the single mutation F95L, which abuts the COMM domain. Notably, the enzyme PfTrpB$^{3C7}$ contained two mutations, I16V and Q89L, of which the former is adjacent to the E17G mutation already present in the parent enzyme. The six missense mutations found to be activating for activity on Thr were subjected to recombination, which resulted in the final variant PfTrpB$^{2B9}$. Three mutations, F95L, I16V, and V384A were retained in this enzymes, which is eight mutations away from wild-type and has at least a 6,000-fold boost in productivity. This increase is, in part, due to an increase in expression of soluble protein from ~80 mg PfTrpB per L media, to ~350 mg of PfTrpB$^{2B9}$, indicating at least a 1,400-fold increase in catalytic efficiency with Thr.

To assess the molecular basis of this new activity, UV-vis spectroscopy was used, which reports on the steady state distribution of the PLP-bound intermediates in the catalytic cycle. When Ser is added to PfTrpB in its open conformation, λ$_{max}$ shifts from 412 nm to 428 nm, corresponding to transimination of the lysine-bound internal aldimine, E(Ain), to a Ser-bound external aldimine, E(Aex$_1$). However, addition of 20 mM Thr to PfTrpB did not result in any spectral shift indicative of Thr binding. This experiment, however, cannot rule out that Thr binds non-covalently and that E(Aex$_1$) is simply no longer favored. Thr was soaked into crystals of PfTrpB and diffraction yielded a 1.54-Å structure that clearly shows Thr does indeed bind non-covalently. The Thr hydroxyl forms a 2.7-Å hydrogen bond with the sidechain of Asp300, an interaction that is also observed in the Ser external aldimine. Modeling of a hypothetical Thr external aldimine that maintains the Asp300 hydrogen bond reveals a strong steric clash between the Thr methyl group and the backbone carbonyl of Gly298, accounting for the lack of E(Aex$_1$) observed by UV-vis spectroscopy.

UV-vis spectroscopy was used to probe the basis for enhanced activity through directed evolution and addition of 20 mM Thr to each generation of engineered proteins resulted in a clear trend. The 412 nm peak decreases while a new absorbance band at 350 nm with a broad shoulder out to 550 nm appears, consistent with accumulation of the electrophilic amino acrylate species E(A-A). A similar phenomenon was observed with the directed evolution for independent TrpB function, however comparison of the Ser- and Thr-bound PfTrpB$^{4D11}$ spectra clearly indicate that the E(Aex$_1$) and E(A-A) with Thr are much less stable.

The engineered PfTrpB$^{2B9}$ enzyme has several desirable features as a catalyst for β-MeTrp production. It is robustly expressed in E. coli, can be prepared in a moderately pure form as a heat-treated lysate, and its thermal stability permits high reaction temperatures, routinely up to 75° C., which greatly increases the solubility of hydrophobic substrates. However, in reactions with one equivalent each of indole and Thr, only 44% conversion to product, corresponding to 2220 turnovers was observed. A clue explaining this low conversion came from UV-vis spectroscopy, which revealed that addition of Thr to PfTrpB$^{2B9}$ results in a time-dependent increase in absorbance at 320 nm, while the remainder of the spectrum remains constant. This was attributed to α-keto butyrate production from the well-described deamination reaction that results when a nucleophile does not add into C-β and E(Ain) is reformed through transimination. The precise timing of the subsequent steps is unknown, but the net effect is an abortive reaction wherein the amino acrylate hydrolyses to form α-keto butyrate and ammonium. Thus, additional equivalents of Thr was added to the β-substitution reaction with indole, which enabled complete conversion of indole to β-MeTrp and up to 8,200 total turnovers.

With these reaction conditions in hand, a characterization of the substrate scope of the reaction with Thr was performed. A small panel of indole-like nucleophiles were screened for reaction with PfTrpB$^{OB2}$ and Ser, and a significant boosts in activity was observed. This was expanded on this panel of nucleophiles and tests for activity with PfTrpB$^{2B9}$ using an excess of Thr was performed. Reactions were run to intermediate yield to determine the TTN with a given nucleophile and the identity of the products was established with a separate preparative-scale reaction using 100 mM nucleophile, 1.0 M Thr, and 0.02-0.25 mol % PfTrpB$^{2B9}$ catalyst. Good reactivity was observed with the 2-methyl and 6-methyl indole substrates, and decreases in TTN compared to indole demonstrate the active site is sensitive to steric perturbations. To probe the role of electronic effects on the C—C bond forming step, activity was tested with 4-fluoro and 5-fluoroindole, which are more closely isosteric with indole but have decreased electron density in the π-system. Product formation with each substrate and 3.4-fold decreased TTN with the 4-fluoro substrate was observed, which is more electron withdrawing at C-3 than the 5-fluoro substituent. The increased steric constraints of the activity site were again clear, as no activity with the 5-chloro-, 5-bromo-, and 6-hydroxyindoles, which undergo reaction with Ser, was observed. A productive reaction was observed with 7-azaindole, which is a substantially weaker nucleophile than indole, and fewer turnovers were observed. Interestingly, a second product was detected in the reaction with 7-azaindole that was assigned as an N-alkylated product. This regioselectivity is well known with the indazole, which we found reacts exclusively to form the N-alkylated product. Surprisingly, no product formation with indoline was observed, which is a stronger nucleophile than indazole or indole and reacts significantly faster in the reaction with Ser. S-alkylation was also tested using thiophenol and benzyl mercaptan and activity was observed with each substrate, but with low turnover and a conspicuous white precipitate in the reaction. Analysis revealed a late eluting peak in the LC-MS that did not ionize, indicative of oxidative dimerization of the substrate. Inclusion of DTT reduced this side reaction.

The data demonstrate that the disclosure provides a new, non-natural enzymatic route for the biocatalytic production of (2S,3S)-β-MeTrp. This activity lies in the β-subunit of TrpS, which was subsequently engineered for increased activity with Thr as the amino acid donor. The development of the resultant catalyst, PfTrpB$^{2B9}$, was greatly facilitated by previous efforts to simplify the native two-enzyme system and the engineered proteins have high thermal stability and expression in E. coli, enhancing their utility as practical biocatalysts. This enzymatic route to β-MeTrp is dramatically shorter than previous synthetic routes, and also the native 3-enzyme step to this natural metabolite. This highlights the capability of protein engineering to quickly produce complicated molecules from simple precursors, and offers a simple and expandable route for the production of β-methyl ncAA analogs for future studies.

A number of embodiments of the invention have been described. Nevertheless, it will be understood that various modifications may be made without departing from the spirit and scope of the invention. Accordingly, other embodiments are within the scope of the following claims.

What is claimed is:

1. A method for producing a β-methyl-tryptophan or analog thereof, the method comprising:
   (a) providing L-threonine, an indole or indole analog, and a polypeptide consisting of SEQ ID NOs: 10, 12, 14, 16, 18, 20, 22, 24, 26, 28, 30, 32, 34, 36, or 38; and
   (b) admixing the components of (a) in a reaction for a time and under conditions to produce a β-methyl-tryptophan or analog thereof,
   wherein the indole analog is a compound according to Formula I:

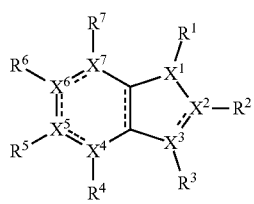

Formula I wherein
$X^1$, $X^2$, and $X^3$ are independently carbon or nitrogen;
$X^4$-$X^7$ are carbon or nitrogen; and
$R^1$-$R^7$ are each independently selected from the group consisting of (i) H, —OH, an alkyl, an aryl, an alkoxy, an alkene, an alkyne, and substitutions of the foregoing, (ii) a sulfur-containing group, (iii) a nitrogen-containing group, (iv) an oxygen-containing group, and (v) a halogen.

2. The method of claim 1, wherein the polypeptide consists of SEQ ID NO: 10.

3. The method of claim 1, wherein the polypeptide consists of SEQ ID NO: 12.

4. The method of claim 1, wherein the polypeptide consists of SEQ ID NO: 14.

5. The method of claim 1, wherein the polypeptide consists of SEQ ID NO: 16.

6. The method of claim 1, wherein the polypeptide consists of SEQ ID NO: 18.

7. The method of claim 1, wherein the polypeptide consists of SEQ ID NO: 20.

8. The method of claim 1, wherein the polypeptide consists of SEQ ID NO: 22.

9. The method of claim 1, wherein the polypeptide consists of SEQ ID NO: 24.

10. The method of claim 1, wherein the polypeptide consists of SEQ ID NO: 26.

11. The method of claim 1, wherein the polypeptide consists of SEQ ID NO: 28.

12. The method of claim 1, wherein the polypeptide consists of SEQ ID NO: 30.

13. The method of claim 1, wherein the polypeptide consists of SEQ ID NO: 32.

14. The method of claim 1, wherein the polypeptide consists of SEQ ID NO: 34.

15. The method of claim 1, wherein the polypeptide consists of SEQ ID NO: 36.

16. The method of claim 1, wherein the polypeptide consists of SEQ ID NO: 38.

* * * * *

SEQUENCE LISTING

```
<160> NUMBER OF SEQ ID NOS: 40

<210> SEQ ID NO 1
<211> LENGTH: 1191
<212> TYPE: DNA
<213> ORGANISM: Pyrococcus furiosus
<220> FEATURE:
<221> NAME/KEY: CDS
<222> LOCATION: (1)..(1191)

<400> SEQUENCE: 1 atg tgg ttc ggt gaa ttt ggt ggt cag tac gtg cca gaa acg ctg att      48
Met Trp Phe Gly Glu Phe Gly Gly Gln Tyr Val Pro Glu Thr Leu Ile
1               5                   10                  15 gaa ccg ctg aaa gag ctg gaa aaa gct tac aaa cgt ttc aaa gat gac      96
Glu Pro Leu Lys Glu Leu Glu Lys Ala Tyr Lys Arg Phe Lys Asp Asp
            20                  25                  30 gaa gaa ttc aat cgt caa ctg aat tac tac ctg aaa acc tgg gca ggt     144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
    50                  55                  60 ggt gct aaa atc tac ctg aaa cgt gaa gac ctg gtt cac ggt ggt gca     240
Gly Ala Lys Ile Tyr Leu Lys Arg Glu Asp Leu Val His Gly Gly Ala
65                  70                  75                  80 cac aag acc aac aac gcc atc ggt cag gca ctg ctg gca aag ttc atg     288
His Lys Thr Asn Asn Ala Ile Gly Gln Ala Leu Leu Ala Lys Phe Met
                85                  90                  95 ggt aaa act cgt ctg atc gct gag acc ggt gct ggt cag cac ggc gta     336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg     432
Met Gly Ala Glu Asp Val Glu Arg Gln Lys Met Asn Val Phe Arg Met
    130                 135                 140 aag ctg ctg ggt gca aac gta att cca gtt aac tcc ggt tct cgc acc     480
Lys Leu Leu Gly Ala Asn Val Ile Pro Val Asn Ser Gly Ser Arg Thr
145                 150                 155                 160
```

```
ctg aaa gac gca atc aac gag gct ctg cgt gat tgg gtg gct act ttt      528
Leu Lys Asp Ala Ile Asn Glu Ala Leu Arg Asp Trp Val Ala Thr Phe
            165                 170                 175 gaa tac acc cac tac ctg atc ggt tcc gtg gtc ggt cca cat ccg tat      576
Glu Tyr Thr His Tyr Leu Ile Gly Ser Val Val Gly Pro His Pro Tyr
        180                 185                 190 ccg acc atc gtt cgt gat ttt cag tct gtt atc ggt cgt gag gct aaa      624
Pro Thr Ile Val Arg Asp Phe Gln Ser Val Ile Gly Arg Glu Ala Lys
    195                 200                 205 gcg cag atc ctg gag gct gaa ggt cag ctg cca gat gta atc gtt gct      672
Ala Gln Ile Leu Glu Ala Glu Gly Gln Leu Pro Asp Val Ile Val Ala
210                 215                 220 tgt gtt ggt ggt ggc tct aac gcg atg ggt atc ttt tac ccg ttc gtg      720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc      768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt      816
Leu Glu Ser Gly Lys His Ser Ala Ser Leu Asn Ala Gly Gln Val Gly
            260                 265                 270 gtg ttc cat ggc atg ctg tcc tac ttt ctg cag gac gaa gaa ggt cag      864
Val Phe His Gly Met Leu Ser Tyr Phe Leu Gln Asp Glu Glu Gly Gln
        275                 280                 285 atc aaa cca act cac tcc atc gca cca ggt ctg gat tat cca ggt gtt      912
Ile Lys Pro Thr His Ser Ile Ala Pro Gly Leu Asp Tyr Pro Gly Val
    290                 295                 300 ggt cca gaa cac gct tac ctg aaa aaa att cag cgt gct gaa tac gtg      960
Gly Pro Glu His Ala Tyr Leu Lys Lys Ile Gln Arg Ala Glu Tyr Val
305                 310                 315                 320 act gta acc gat gaa gaa gca ctg aaa gcg ttc cat gaa ctg agc cgt     1008
Thr Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac     1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta     1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg     1152
Asn Leu Ser Gly Arg Gly Asp Lys Asp Leu Asp Ile Val Leu Lys Val
    370                 375                 380 tct ggc aac gtg ctc gag cac cat cac cat cac cat tga                 1191
Ser Gly Asn Val Leu Glu His His His His His His
385                 390                 395
```

<210> SEQ ID NO 2
<211> LENGTH: 396
<212> TYPE: PRT
<213> ORGANISM: Pyrococcus furiosus

<400> SEQUENCE: 2

```
Met Trp Phe Gly Glu Phe Gly Gly Gln Tyr Val Pro Glu Thr Leu Ile
1               5                   10                  15

Glu Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
```

```
                50              55              60
Gly Ala Lys Ile Tyr Leu Lys Arg Glu Asp Leu Val His Gly Gly Ala
 65                  70                  75                  80

His Lys Thr Asn Asn Ala Ile Gly Gln Ala Leu Leu Ala Lys Phe Met
                 85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Phe His Gly Met Leu Ser Tyr Phe Leu Gln Asp Glu Glu Gly Gln
        275                 280                 285

Ile Lys Pro Thr His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Val
370                 375                 380

Ser Gly Asn Val Leu Glu His His His His His
385                 390                 395

<210> SEQ ID NO 3
<211> LENGTH: 1218
<212> TYPE: DNA
<213> ORGANISM: Archaeoglobus fulgidus
<220> FEATURE:
<221> NAME/KEY: CDS
<222> LOCATION: (1)..(1218)

<400> SEQUENCE: 3 atg cgt tgc tgg ctg gaa aac ctg tct ggc ggt cgt aaa atg aag ttt     48
Met Arg Cys Trp Leu Glu Asn Leu Ser Gly Gly Arg Lys Met Lys Phe
 1               5                  10                  15
```

-continued

| | |
|---|---:|
| ggt gag ttt ggc ggt cgt ttc gtt ccg gag gta ctg atc cca ccg ctg<br>Gly Glu Phe Gly Gly Arg Phe Val Pro Glu Val Leu Ile Pro Pro Leu<br>           20                 25                 30 | 96 |
| gaa gaa ctg gaa aaa gca tat gac cgc ttt aaa gat gat gag gaa ttt<br>Glu Glu Leu Glu Lys Ala Tyr Asp Arg Phe Lys Asp Asp Glu Glu Phe<br>      35               40                 45 | 144 |
| aaa gca cgt ctg gaa tac tac ctg aaa tcc tat gca ggt cgt ccg acc<br>Lys Ala Arg Leu Glu Tyr Tyr Leu Lys Ser Tyr Ala Gly Arg Pro Thr<br>50                 55                 60 | 192 |
| cca ctg tac ttc gct gag aac ctg agc cgt gaa ctg ggc gtc aaa atc<br>Pro Leu Tyr Phe Ala Glu Asn Leu Ser Arg Glu Leu Gly Val Lys Ile<br>65                 70                 75                 80 | 240 |
| tat ctg aaa cgc gaa gac ctg ctg cat ggt ggt gcg cac aaa atc aac<br>Tyr Leu Lys Arg Glu Asp Leu Leu His Gly Gly Ala His Lys Ile Asn<br>               85                 90                 95 | 288 |
| aat acc atc ggt caa gcg ctg ctg gcg aaa ttc atg ggt aaa aag cgt<br>Asn Thr Ile Gly Gln Ala Leu Leu Ala Lys Phe Met Gly Lys Lys Arg<br>              100                105              110 | 336 |
| gtt att gcg gaa acc ggt gca ggt cag cac ggt gtg gcg act gcg atg<br>Val Ile Ala Glu Thr Gly Ala Gly Gln His Gly Val Ala Thr Ala Met<br>        115                120              125 | 384 |
| gct gcg gca ctg ctg ggc ctg gaa gcg gaa att tat atg ggt gct gaa<br>Ala Ala Ala Leu Leu Gly Leu Glu Ala Glu Ile Tyr Met Gly Ala Glu<br>130               135                140 | 432 |
| gac tat gag cgc caa aaa atg aac gtg ttt cgt atg gaa ctg ctg ggt<br>Asp Tyr Glu Arg Gln Lys Met Asn Val Phe Arg Met Glu Leu Leu Gly<br>145               150                155              160 | 480 |
| gcc aaa gtc acc gct gta gaa agc ggt tcc cgt acc ctg aaa gac gca<br>Ala Lys Val Thr Ala Val Glu Ser Gly Ser Arg Thr Leu Lys Asp Ala<br>              165                170              175 | 528 |
| atc aac gag gca ctg cgt gac tgg gtg gaa tct ttc gaa cac act cac<br>Ile Asn Glu Ala Leu Arg Asp Trp Val Glu Ser Phe Glu His Thr His<br>                180                185              190 | 576 |
| tac ctg atc ggt tct gta gta ggt cca cat ccg ttc ccg act atc gtc<br>Tyr Leu Ile Gly Ser Val Val Gly Pro His Pro Phe Pro Thr Ile Val<br>        195                200              205 | 624 |
| cgc gac ttc caa gct gtg atc ggc aag gag gca cgc cgt cag atc atc<br>Arg Asp Phe Gln Ala Val Ile Gly Lys Glu Ala Arg Arg Gln Ile Ile<br>210               215                220 | 672 |
| gaa gcg gaa ggt ggt atg ccg gat gct atc atc gcg tgc gta ggc ggt<br>Glu Ala Glu Gly Gly Met Pro Asp Ala Ile Ile Ala Cys Val Gly Gly<br>225               230                235              240 | 720 |
| ggc tcc aac gct atg ggc atc ttc cac ccg ttc ctg aac gac gac gta<br>Gly Ser Asn Ala Met Gly Ile Phe His Pro Phe Leu Asn Asp Asp Val<br>              245                250              255 | 768 |
| cgt ctg att ggt gta gaa gct ggc ggt gaa ggt atc gaa tct ggt cgt<br>Arg Leu Ile Gly Val Glu Ala Gly Gly Glu Gly Ile Glu Ser Gly Arg<br>        260                265              270 | 816 |
| cat tcc gca agc ctg acc gct ggc tct aaa ggt gtt ctg cac ggt atg<br>His Ser Ala Ser Leu Thr Ala Gly Ser Lys Gly Val Leu His Gly Met<br>275               280                285 | 864 |
| ctg agc tat ttc ctg cag gac gaa gag ggt atg atg ctg gac acc cac<br>Leu Ser Tyr Phe Leu Gln Asp Glu Glu Gly Met Met Leu Asp Thr His<br>290               295                300 | 912 |
| tcc gta tct gca ggt ctg gat tat ccg ggt gtt ggt ccg gaa cac gcc<br>Ser Val Ser Ala Gly Leu Asp Tyr Pro Gly Val Gly Pro Glu His Ala<br>305               310                315              320 | 960 |
| tac ctg aag gaa acg ggt cgt tgt gag tac gtt acc gta aat gac gaa<br>Tyr Leu Lys Glu Thr Gly Arg Cys Glu Tyr Val Thr Val Asn Asp Glu | 1008 |

-continued

```
                       325                 330                 335
gaa gcg ctg cgt gct ttc aaa acc ctg tcc aaa ctg gaa ggt atc att    1056
Glu Ala Leu Arg Ala Phe Lys Thr Leu Ser Lys Leu Glu Gly Ile Ile
        340                 345                 350 cct gcg ctg gaa tcc gct cac gcc att gca tat gct atg aaa atg gcc    1104
Pro Ala Leu Glu Ser Ala His Ala Ile Ala Tyr Ala Met Lys Met Ala
                355                 360                 365 gag gaa atg cag cgt gat gat gtg ctg gtt gta aac ctg tcc ggt cgt    1152
Glu Glu Met Gln Arg Asp Asp Val Leu Val Val Asn Leu Ser Gly Arg
370                 375                 380 ggc gat aaa gat atg gac atc gta cgt cgt cgt ctg gct ctc gag cac    1200
Gly Asp Lys Asp Met Asp Ile Val Arg Arg Arg Leu Ala Leu Glu His
385                 390                 395                 400 cac cac cac cac cac tga                                            1218
His His His His His
            405

<210> SEQ ID NO 4
<211> LENGTH: 405
<212> TYPE: PRT
<213> ORGANISM: Archaeoglobus fulgidus

<400> SEQUENCE: 4

Met Arg Cys Trp Leu Glu Asn Leu Ser Gly Gly Arg Lys Met Lys Phe
1               5                   10                  15

Gly Glu Phe Gly Gly Arg Phe Val Pro Glu Val Leu Ile Pro Pro Leu
            20                  25                  30

Glu Glu Leu Glu Lys Ala Tyr Asp Arg Phe Lys Asp Asp Glu Glu Phe
        35                  40                  45

Lys Ala Arg Leu Glu Tyr Tyr Leu Lys Ser Tyr Ala Gly Arg Pro Thr
    50                  55                  60

Pro Leu Tyr Phe Ala Glu Asn Leu Ser Arg Glu Leu Gly Val Lys Ile
65                  70                  75                  80

Tyr Leu Lys Arg Glu Asp Leu Leu His Gly Gly Ala His Lys Ile Asn
                85                  90                  95

Asn Thr Ile Gly Gln Ala Leu Leu Ala Lys Phe Met Gly Lys Lys Arg
            100                 105                 110

Val Ile Ala Glu Thr Gly Ala Gly Gln His Gly Val Ala Thr Ala Met
        115                 120                 125

Ala Ala Ala Leu Leu Gly Leu Glu Ala Glu Ile Tyr Met Gly Ala Glu
    130                 135                 140

Asp Tyr Glu Arg Gln Lys Met Asn Val Phe Arg Met Glu Leu Leu Gly
145                 150                 155                 160

Ala Lys Val Thr Ala Val Glu Ser Gly Ser Arg Thr Leu Lys Asp Ala
                165                 170                 175

Ile Asn Glu Ala Leu Arg Asp Trp Val Glu Ser Phe Glu His Thr His
            180                 185                 190

Tyr Leu Ile Gly Ser Val Val Gly Pro His Pro Phe Pro Thr Ile Val
        195                 200                 205

Arg Asp Phe Gln Ala Val Ile Gly Lys Glu Ala Arg Arg Gln Ile Ile
    210                 215                 220

Glu Ala Glu Gly Gly Met Pro Asp Ala Ile Ile Ala Cys Val Gly Gly
225                 230                 235                 240

Gly Ser Asn Ala Met Gly Ile Phe His Pro Phe Leu Asn Asp Asp Val
                245                 250                 255

Arg Leu Ile Gly Val Glu Ala Gly Gly Glu Gly Ile Glu Ser Gly Arg
```

```
                    260                 265                 270
His Ser Ala Ser Leu Thr Ala Gly Ser Lys Gly Val Leu His Gly Met
            275                 280                 285

Leu Ser Tyr Phe Leu Gln Asp Glu Glu Gly Met Met Leu Asp Thr His
            290                 295                 300

Ser Val Ser Ala Gly Leu Asp Tyr Pro Gly Val Gly Pro Glu His Ala
305                 310                 315                 320

Tyr Leu Lys Glu Thr Gly Arg Cys Glu Tyr Val Thr Val Asn Asp Glu
                325                 330                 335

Glu Ala Leu Arg Ala Phe Lys Thr Leu Ser Lys Leu Glu Gly Ile Ile
            340                 345                 350

Pro Ala Leu Glu Ser Ala His Ala Ile Ala Tyr Ala Met Lys Met Ala
            355                 360                 365

Glu Glu Met Gln Arg Asp Asp Val Leu Val Val Asn Leu Ser Gly Arg
            370                 375                 380

Gly Asp Lys Asp Met Asp Ile Val Arg Arg Leu Ala Leu Glu His
385                 390                 395                 400

His His His His His
            405

<210> SEQ ID NO 5
<211> LENGTH: 1194
<212> TYPE: DNA
<213> ORGANISM: Thermotoga maritima
<220> FEATURE:
<221> NAME/KEY: CDS
<222> LOCATION: (1)..(1194)

<400> SEQUENCE: 5 atg aaa ggc tac ttc ggt ccg tac ggt ggc cag tac gtg ccg gaa atc          48
Met Lys Gly Tyr Phe Gly Pro Tyr Gly Gly Gln Tyr Val Pro Glu Ile
1               5                   10                  15 ctg atg cca gct ctg gaa gaa ctg gaa gct gcg tac gaa gaa atc atg          96
Leu Met Pro Ala Leu Glu Glu Leu Glu Ala Ala Tyr Glu Glu Ile Met
                20                  25                  30 aaa gat gag tct ttc tgg aaa gaa ttc aat gac ctg ctg cgc gat tat         144
Lys Asp Glu Ser Phe Trp Lys Glu Phe Asn Asp Leu Leu Arg Asp Tyr
            35                  40                  45 gcg ggt cgt ccg act ccg ctg tac ttc gca cgt cgt ctg tcc gaa aaa         192
Ala Gly Arg Pro Thr Pro Leu Tyr Phe Ala Arg Arg Leu Ser Glu Lys
        50                  55                  60 tac ggt gct cgc atc tat ctg aaa cgt gaa gac ctg ctg cat act ggt         240
Tyr Gly Ala Arg Ile Tyr Leu Lys Arg Glu Asp Leu Leu His Thr Gly
65                  70                  75                  80 gcg cat aaa atc aat aac gct atc ggc cag gtt ctg ctg gca aaa aaa         288
Ala His Lys Ile Asn Asn Ala Ile Gly Gln Val Leu Leu Ala Lys Lys
                85                  90                  95 atg ggc aaa acc cgt atc att gct gaa acg ggt gct ggt cag cac ggc         336
Met Gly Lys Thr Arg Ile Ile Ala Glu Thr Gly Ala Gly Gln His Gly
                100                 105                 110 gta gca act gct acc gca gca gcg ctg ttc ggt atg gaa tgt gta atc         384
Val Ala Thr Ala Thr Ala Ala Ala Leu Phe Gly Met Glu Cys Val Ile
            115                 120                 125 tat atg ggc gaa gaa gac acg atc cgc cag aaa ccg aac gtt gaa cgt         432
Tyr Met Gly Glu Glu Asp Thr Ile Arg Gln Lys Pro Asn Val Glu Arg
        130                 135                 140 atg aaa ctg ctg ggt gct aaa gtt gta ccg gta aaa tcc ggt agc cgt         480
Met Lys Leu Leu Gly Ala Lys Val Val Pro Val Lys Ser Gly Ser Arg
145                 150                 155                 160
```

```
acc ctg aaa gac gca att aac gaa gct ctg cgt gac tgg att acc aac      528
Thr Leu Lys Asp Ala Ile Asn Glu Ala Leu Arg Asp Trp Ile Thr Asn
            165                 170                 175 ctg cag acc acc tat tac gtg atc ggc tct gtg gtt ggt ccg cat cca      576
Leu Gln Thr Thr Tyr Tyr Val Ile Gly Ser Val Val Gly Pro His Pro
        180                 185                 190 tat ccg att atc gta cgt aac ttc caa aag gtt atc ggc gaa gag acc      624
Tyr Pro Ile Ile Val Arg Asn Phe Gln Lys Val Ile Gly Glu Glu Thr
195                 200                 205 aaa aaa cag att ctg gaa aaa gaa ggc cgt ctg ccg gac tac atc gtt      672
Lys Lys Gln Ile Leu Glu Lys Glu Gly Arg Leu Pro Asp Tyr Ile Val
    210                 215                 220 gcg tgc gtg ggt ggt ggt tct aac gct gcc ggt atc ttc tat ccg ttt      720
Ala Cys Val Gly Gly Gly Ser Asn Ala Ala Gly Ile Phe Tyr Pro Phe
225                 230                 235                 240 atc gat tct ggt gtg aag ctg atc ggc gta gaa gcc ggt ggc gaa ggt      768
Ile Asp Ser Gly Val Lys Leu Ile Gly Val Glu Ala Gly Gly Glu Gly
            245                 250                 255 ctg gaa acc ggt aaa cat gcg gct tct ctg ctg aaa ggt aaa atc ggc      816
Leu Glu Thr Gly Lys His Ala Ala Ser Leu Leu Lys Gly Lys Ile Gly
        260                 265                 270 tac ctg cac ggt tct aag acg ttc gtt ctg cag gat gac tgg ggt caa      864
Tyr Leu His Gly Ser Lys Thr Phe Val Leu Gln Asp Asp Trp Gly Gln
275                 280                 285 gtt cag gtg acg cac tcc gtc tcc gct ggc ctg gac tac tcc ggt gtc      912
Val Gln Val Thr His Ser Val Ser Ala Gly Leu Asp Tyr Ser Gly Val
    290                 295                 300 ggt ccg gaa cac gcc tat tgg cgt gag acc ggt aaa gtg ctg tac gat      960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc     1008
Ala Val Thr Asp Glu Glu Ala Leu Asp Ala Phe Ile Glu Leu Ser Arg
            325                 330                 335 ctg gaa ggc atc atc cca gcc ctg gag tct tct cac gca ctg gct tat     1056
Leu Glu Gly Ile Ile Pro Ala Leu Glu Ser Ser His Ala Leu Ala Tyr
        340                 345                 350 ctg aag aag atc aac atc aag ggt aaa gtt gtg gtg gtt aat ctg tct     1104
Leu Lys Lys Ile Asn Ile Lys Gly Lys Val Val Val Val Asn Leu Ser
355                 360                 365 ggt cgt ggt gac aag gat ctg gaa tct gta ctg aac cac ccg tat gtt     1152
Gly Arg Gly Asp Lys Asp Leu Glu Ser Val Leu Asn His Pro Tyr Val
    370                 375                 380 cgc gaa cgc atc cgc ctc gag cac cac cac cac cac cac tga             1194
Arg Glu Arg Ile Arg Leu Glu His His His His His His
385                 390                 395

<210> SEQ ID NO 6
<211> LENGTH: 397
<212> TYPE: PRT
<213> ORGANISM: Thermotoga maritima

<400> SEQUENCE: 6

Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
```

```
                     50                  55                  60
Tyr Gly Ala Arg Ile Tyr Leu Lys Arg Glu Asp Leu Leu His Thr Gly
 65                  70                  75                  80

Ala His Lys Ile Asn Asn Ala Ile Gly Gln Val Leu Leu Ala Lys Lys
                 85                  90                  95

Met Gly Lys Thr Arg Ile Ile Ala Glu Thr Gly Ala Gly Gln His Gly
            100                 105                 110

Val Ala Thr Ala Thr Ala Ala Leu Phe Gly Met Glu Cys Val Ile
            115                 120                 125

Tyr Met Gly Glu Glu Asp Thr Ile Arg Gln Lys Pro Asn Val Glu Arg
            130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
            195                 200                 205

Lys Lys Gln Ile Leu Glu Lys Glu Gly Arg Leu Pro Asp Tyr Ile Val
            210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
            275                 280                 285

Val Gln Val Thr His Ser Val Ser Ala Gly Leu Asp Tyr Ser Gly Val
            290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
            370                 375                 380

Arg Glu Arg Ile Arg Leu Glu His His His His His
385                 390                 395

<210> SEQ ID NO 7
<211> LENGTH: 1218
<212> TYPE: DNA
<213> ORGANISM: Escherichia coli
<220> FEATURE:
<221> NAME/KEY: CDS
<222> LOCATION: (1)..(1218)

<400> SEQUENCE: 7 atg act act ctg ctg aac ccg tac ttc ggt gag ttc ggt ggt atg tac    48
Met Thr Thr Leu Leu Asn Pro Tyr Phe Gly Glu Phe Gly Gly Met Tyr
 1               5                   10                  15
```

-continued

| | |
|---|---|
| gtg cca cag atc ctg atg cct gcg ctg cgc cag ctg gag gag gcg ttt<br>Val Pro Gln Ile Leu Met Pro Ala Leu Arg Gln Leu Glu Glu Ala Phe<br>20 25 30 | 96 |
| gtt agc gcc cag aaa gat ccg gag ttc cag gct cag ttc aac gac ctg<br>Val Ser Ala Gln Lys Asp Pro Glu Phe Gln Ala Gln Phe Asn Asp Leu<br>35 40 45 | 144 |
| ctg aaa aac tat gct ggt cgt ccg acc gcg ctg acg aaa tgc cag aac<br>Leu Lys Asn Tyr Ala Gly Arg Pro Thr Ala Leu Thr Lys Cys Gln Asn<br>50 55 60 | 192 |
| atc act gct ggt acg aac acc acc ctg tac ctg aag cgt gag gac ctg<br>Ile Thr Ala Gly Thr Asn Thr Thr Leu Tyr Leu Lys Arg Glu Asp Leu<br>65 70 75 80 | 240 |
| ctg cat ggt ggt gcg cac aaa acc aac cag gtc ctg ggt caa gca ctg<br>Leu His Gly Gly Ala His Lys Thr Asn Gln Val Leu Gly Gln Ala Leu<br>85 90 95 | 288 |
| ctg gca aaa cgt atg ggc aaa act gaa att att gcg gaa acg ggt gca<br>Leu Ala Lys Arg Met Gly Lys Thr Glu Ile Ile Ala Glu Thr Gly Ala<br>100 105 110 | 336 |
| ggt cag cac ggt gta gct tct gcg ctg gcc agc gca ctg ctg ggt ctg<br>Gly Gln His Gly Val Ala Ser Ala Leu Ala Ser Ala Leu Leu Gly Leu<br>115 120 125 | 384 |
| aag tgt cgt atc tat atg ggt gcg aaa gat gtg gag cgt cag tct ccg<br>Lys Cys Arg Ile Tyr Met Gly Ala Lys Asp Val Glu Arg Gln Ser Pro<br>130 135 140 | 432 |
| aac gta ttc cgc atg cgt ctg atg ggt gca gaa gtg atc ccg gta cac<br>Asn Val Phe Arg Met Arg Leu Met Gly Ala Glu Val Ile Pro Val His<br>145 150 155 160 | 480 |
| tct ggt tcc gca act ctg aaa gac gca tgt aat gaa gca ctg cgt gac<br>Ser Gly Ser Ala Thr Leu Lys Asp Ala Cys Asn Glu Ala Leu Arg Asp<br>165 170 175 | 528 |
| tgg tcc ggt tct tat gaa act gct cac tac atg ctg ggc acc gca gct<br>Trp Ser Gly Ser Tyr Glu Thr Ala His Tyr Met Leu Gly Thr Ala Ala<br>180 185 190 | 576 |
| ggt cct cac ccg tac ccg acc atc gta cgt gaa ttc cag cgc atg att<br>Gly Pro His Pro Tyr Pro Thr Ile Val Arg Glu Phe Gln Arg Met Ile<br>195 200 205 | 624 |
| ggt gaa gaa acc aaa gcg cag atc ctg gaa cgt gaa ggt cgc ctg cca<br>Gly Glu Glu Thr Lys Ala Gln Ile Leu Glu Arg Glu Gly Arg Leu Pro<br>210 215 220 | 672 |
| gat gcg gtg atc gcg tgc gta ggt ggt ggt tcc aac gcg atc ggt atg<br>Asp Ala Val Ile Ala Cys Val Gly Gly Gly Ser Asn Ala Ile Gly Met<br>225 230 235 240 | 720 |
| ttc gct gat ttc atc aac gaa acc aac gtt ggc ctg att ggt gta gaa<br>Phe Ala Asp Phe Ile Asn Glu Thr Asn Val Gly Leu Ile Gly Val Glu<br>245 250 255 | 768 |
| cca ggt ggc cac ggc att gaa act ggc gag cac ggt gca cct ctg aaa<br>Pro Gly Gly His Gly Ile Glu Thr Gly Glu His Gly Ala Pro Leu Lys<br>260 265 270 | 816 |
| cac ggt cgc gta ggc att tac ttc ggt atg aaa gct ccg atg atg cag<br>His Gly Arg Val Gly Ile Tyr Phe Gly Met Lys Ala Pro Met Met Gln<br>275 280 285 | 864 |
| act gaa gac ggt cag atc gaa gaa tct tac tcc att tct gca ggt ctg<br>Thr Glu Asp Gly Gln Ile Glu Glu Ser Tyr Ser Ile Ser Ala Gly Leu<br>290 295 300 | 912 |
| gac ttc ccg tct gtt ggt ccg caa cac gca tat ctg aac tct acc ggt<br>Asp Phe Pro Ser Val Gly Pro Gln His Ala Tyr Leu Asn Ser Thr Gly<br>305 310 315 320 | 960 |
| cgt gcg gac tac gtg tct atc act gac gac gag gct ctg gag gcc ttt<br>Arg Ala Asp Tyr Val Ser Ile Thr Asp Asp Glu Ala Leu Glu Ala Phe | 1008 |

```
                     325                 330                 335
aaa act ctg tgc ctg cac gaa ggt atc att cca gct ctg gaa tcc agc      1056
Lys Thr Leu Cys Leu His Glu Gly Ile Ile Pro Ala Leu Glu Ser Ser
        340                 345                 350 cac gca ctg gca cac gca ctg aaa atg atg cgt gaa aac cca gac aaa      1104
His Ala Leu Ala His Ala Leu Lys Met Met Arg Glu Asn Pro Asp Lys
            355                 360                 365 gaa cag ctg ctg gtg gtt aac ctg agc ggt cgt ggt gac aag gat atc      1152
Glu Gln Leu Leu Val Val Asn Leu Ser Gly Arg Gly Asp Lys Asp Ile
370                 375                 380 ttc acg gtt cac gac atc ctg aag gct cgt ggt gaa atc ctc gag cac      1200
Phe Thr Val His Asp Ile Leu Lys Ala Arg Gly Glu Ile Leu Glu His
385                 390                 395                 400 cac cac cac cac cac tga                                              1218
His His His His His
            405

<210> SEQ ID NO 8
<211> LENGTH: 405
<212> TYPE: PRT
<213> ORGANISM: Escherichia coli

<400> SEQUENCE: 8

Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110

Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
    130                 135                 140

Asn Val Phe Arg Met Arg Leu Met Gly Ala Glu Val Ile Pro Val His
145                 150                 155                 160

Ser Gly Ser Ala Thr Leu Lys Asp Ala Cys Asn Glu Ala Leu Arg Asp
                165                 170                 175

Trp Ser Gly Ser Tyr Glu Thr Ala His Tyr Met Leu Gly Thr Ala Ala
            180                 185                 190

Gly Pro His Pro Tyr Pro Thr Ile Val Arg Glu Phe Gln Arg Met Ile
        195                 200                 205

Gly Glu Glu Thr Lys Ala Gln Ile Leu Glu Arg Glu Gly Arg Leu Pro
    210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
```

```
                        260                 265                 270
His Gly Arg Val Gly Ile Tyr Phe Gly Met Lys Ala Pro Met Met Gln
            275                 280                 285

Thr Glu Asp Gly Gln Ile Glu Glu Ser Tyr Ser Ile Ser Ala Gly Leu
            290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
            340                 345                 350

His Ala Leu Ala His Ala Leu Lys Met Met Arg Glu Asn Pro Asp Lys
            355                 360                 365

Glu Gln Leu Leu Val Val Asn Leu Ser Gly Arg Gly Asp Lys Asp Ile
            370                 375                 380

Phe Thr Val His Asp Ile Leu Lys Ala Arg Gly Glu Ile Leu Glu His
385                 390                 395                 400

His His His His
            405

<210> SEQ ID NO 9
<211> LENGTH: 1191
<212> TYPE: DNA
<213> ORGANISM: Artificial Sequence
<220> FEATURE:
<223> OTHER INFORMATION: PfTrpBT292S
<220> FEATURE:
<221> NAME/KEY: CDS
<222> LOCATION: (1)..(1191)

<400> SEQUENCE: 9 atg tgg ttc ggt gaa ttt ggt ggt cag tac gtg cca gaa acg ctg att      48
Met Trp Phe Gly Glu Phe Gly Gly Gln Tyr Val Pro Glu Thr Leu Ile
1               5                   10                  15 gaa ccg ctg aaa gag ctg gaa aaa gct tac aaa cgt ttc aaa gat gac      96
Glu Pro Leu Lys Glu Leu Glu Lys Ala Tyr Lys Arg Phe Lys Asp Asp
                20                  25                  30 gaa gaa ttc aat cgt caa ctg aat tac tac ctg aaa acc tgg gca ggt     144
Glu Glu Phe Asn Arg Gln Leu Asn Tyr Tyr Leu Lys Thr Trp Ala Gly
            35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
        50                  55                  60 ggt gct aaa atc tac ctg aaa cgt gaa gac ctg gtt cac ggt ggt gca     240
Gly Ala Lys Ile Tyr Leu Lys Arg Glu Asp Leu Val His Gly Gly Ala
65                  70                  75                  80 cac aag acc aac aac gcc atc ggt cag gca ctg ctg gca aag ttc atg     288
His Lys Thr Asn Asn Ala Ile Gly Gln Ala Leu Leu Ala Lys Phe Met
                85                  90                  95 ggt aaa act cgt ctg atc gct gag acc ggt gct ggt cag cac ggc gta     336
Gly Lys Thr Arg Leu Ile Ala Glu Thr Gly Ala Gly Gln His Gly Val
                100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
            115                 120                 125 atg ggt gct gag gac gta gaa cgt cag aaa atg aac gta ttc cgt atg     432
Met Gly Ala Glu Asp Val Glu Arg Gln Lys Met Asn Val Phe Arg Met
        130                 135                 140 aag ctg ctg ggt gca aac gta att cca gtt aac tcc ggt tct cgc acc     480
```

```

Lys Leu Leu Gly Ala Asn Val Ile Pro Val Asn Ser Gly Ser Arg Thr
145                 150                 155                 160 ctg aaa gac gca atc aac gag gct ctg cgt gat tgg gtg gct act ttt      528
Leu Lys Asp Ala Ile Asn Glu Ala Leu Arg Asp Trp Val Ala Thr Phe
                165                 170                 175 gaa tac acc cac tac ctg atc ggt tcc gtg gtc ggt cca cat ccg tat      576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa      624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct      672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg      720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc      768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt      816
Leu Glu Ser Gly Lys His Ser Ala Ser Leu Asn Ala Gly Gln Val Gly
            260                 265                 270 gtg ttc cat ggc atg ctg tcc tac ttt ctg cag gac gaa gaa ggt cag      864
Val Phe His Gly Met Leu Ser Tyr Phe Leu Gln Asp Glu Glu Gly Gln
        275                 280                 285 atc aaa cca agc cac tcc atc gca cca ggt ctg gat tat cca ggt gtt      912
Ile Lys Pro Ser His Ser Ile Ala Pro Gly Leu Asp Tyr Pro Gly Val
    290                 295                 300 ggt cca gaa cac gct tac ctg aaa aaa att cag cgt gct gaa tac gtg      960
Gly Pro Glu His Ala Tyr Leu Lys Lys Ile Gln Arg Ala Glu Tyr Val
305                 310                 315                 320 act gta acc gat gaa gaa gca ctg aaa gcg ttc cat gaa ctg agc cgt     1008
Thr Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac     1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta     1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg     1152
Asn Leu Ser Gly Arg Gly Asp Lys Asp Leu Asp Ile Val Leu Lys Val
    370                 375                 380 tct ggc aac gtg ctc gag cac cat cac cat cac cat tga                 1191
Ser Gly Asn Val Leu Glu His His His His His His
385                 390                 395

<210> SEQ ID NO 10
<211> LENGTH: 396
<212> TYPE: PRT
<213> ORGANISM: Artificial Sequence
<220> FEATURE:
<223> OTHER INFORMATION: Synthetic Construct

<400> SEQUENCE: 10

Met Trp Phe Gly Glu Phe Gly Gly Gln Tyr Val Pro Glu Thr Leu Ile
1               5                   10                  15

Glu Pro Leu Lys Glu Leu Glu Lys Ala Tyr Lys Arg Phe Lys Asp Asp
            20                  25                  30
```

```
Glu Glu Phe Asn Arg Gln Leu Asn Tyr Tyr Leu Lys Thr Trp Ala Gly
             35                  40                  45

Arg Pro Thr Pro Leu Tyr Tyr Ala Lys Arg Leu Thr Glu Lys Ile Gly
 50                  55                  60

Gly Ala Lys Ile Tyr Leu Lys Arg Glu Asp Leu Val His Gly Gly Ala
 65                  70                  75                  80

His Lys Thr Asn Asn Ala Ile Gly Gln Ala Leu Leu Ala Lys Phe Met
                 85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Phe His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Val
370                 375                 380

Ser Gly Asn Val Leu Glu His His His His His
385                 390                 395
```

<210> SEQ ID NO 11
<211> LENGTH: 1191
<212> TYPE: DNA
<213> ORGANISM: Artificial Sequence
<220> FEATURE:
<223> OTHER INFORMATION: PfTrpB0B2
<220> FEATURE:
<221> NAME/KEY: CDS
<222> LOCATION: (1)..(1191)

<400> SEQUENCE: 11

```
atg tgg ttc ggt gaa ttt ggt ggt cag tac gtg cta gaa acg ctg att      48
Met Trp Phe Gly Glu Phe Gly Gly Gln Tyr Val Leu Glu Thr Leu Ile
1               5                   10                  15 gga ccc ctg aaa gag ctg gaa aaa gct tac aaa cgt ttc aaa gat gac      96
Gly Pro Leu Lys Glu Leu Glu Lys Ala Tyr Lys Arg Phe Lys Asp Asp
            20                  25                  30 gaa gaa ttc aat cgt caa ctg aat tac tac ctg aaa acc tgg gca ggt     144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca     240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ttc atg     288
His Lys Thr Asn Asn Ala Ile Gly Gln Ala Leu Leu Ala Lys Phe Met
                85                  90                  95 ggt aaa act cgt ctg atc gct gag acc ggt gct ggt cag cac ggc gta     336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg     432
Met Gly Ala Glu Asp Val Glu Arg Gln Lys Met Asn Val Phe Arg Met
    130                 135                 140 aag ctg ctg ggt gca aac gta att cca gtt aac tcc ggt tct cgc acc     480
Lys Leu Leu Gly Ala Asn Val Ile Pro Val Asn Ser Gly Ser Arg Thr
145                 150                 155                 160 ctg aaa gac gca atc aac gag gct ctg cgt gat tgg gtg gct acc ttt     528
Leu Lys Asp Ala Ile Asn Glu Ala Leu Arg Asp Trp Val Ala Thr Phe
                165                 170                 175 gaa tac acc cac tac cta atc ggt tcc gtg gtc ggt cca cat ccg tat     576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa     624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct     672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg     720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc     768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt     816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag     864
Val Ser His Gly Met Leu Ser Tyr Phe Leu Gln Asp Glu Glu Gly Gln
        275                 280                 285 atc aaa cca agc cac tcc atc gca cca ggt ctg gat tat cca ggt gtt     912
Ile Lys Pro Ser His Ser Ile Ala Pro Gly Leu Asp Tyr Pro Gly Val
    290                 295                 300
```

```
ggt cca gaa cac gct tac ctg aaa aaa att cag cgt gct gaa tac gtg    960
Gly Pro Glu His Ala Tyr Leu Lys Lys Ile Gln Arg Ala Glu Tyr Val
305             310                 315                 320 gct gta acc gat gaa gaa gca ctg aaa gcg ttc cat gaa ctg agc cgt   1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac   1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta   1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg   1152
Asn Leu Ser Gly Arg Gly Asp Lys Asp Leu Asp Ile Val Leu Lys Val
    370                 375                 380 tct ggc aac gtg ctc gag cac cat cac cat cac cat tga               1191
Ser Gly Asn Val Leu Glu His His His His His His
385                 390                 395
```

```
<210> SEQ ID NO 12
<211> LENGTH: 396
<212> TYPE: PRT
<213> ORGANISM: Artificial Sequence
<220> FEATURE:
<223> OTHER INFORMATION: Synthetic Construct

<400> SEQUENCE: 12

Met Trp Phe Gly Glu Phe Gly Gly Gln Tyr Val Leu Glu Thr Leu Ile
1               5                   10                  15

Gly Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Phe Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240
```

```
Asn Asp Lys Lys Val Lys Leu Val Gly Val Glu Ala Gly Gly Lys Gly
            245                 250                 255

Leu Glu Ser Gly Lys His Ser Ala Ser Leu Asn Ala Gly Gln Val Gly
        260                 265                 270

Val Ser His Gly Met Leu Ser Tyr Phe Leu Gln Asp Glu Glu Gly Gln
    275                 280                 285

Ile Lys Pro Ser His Ser Ile Ala Pro Gly Leu Asp Tyr Pro Gly Val
290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
            325                 330                 335

Thr Glu Gly Ile Ile Pro Ala Leu Glu Ser Ala His Ala Val Ala Tyr
        340                 345                 350

Ala Met Lys Leu Ala Lys Glu Met Ser Arg Asp Glu Ile Ile Ile Val
    355                 360                 365

Asn Leu Ser Gly Arg Gly Asp Lys Asp Leu Asp Ile Val Leu Lys Val
370                 375                 380

Ser Gly Asn Val Leu Glu His His His His His His
385                 390                 395

<210> SEQ ID NO 13
<211> LENGTH: 1191
<212> TYPE: DNA
<213> ORGANISM: Artificial Sequence
<220> FEATURE:
<223> OTHER INFORMATION: PfTrpB4G1
<220> FEATURE:
<221> NAME/KEY: CDS
<222> LOCATION: (1)..(1191)

<400> SEQUENCE: 13 atg tgg ttc ggt gaa ttt ggt ggt cag tac gtg cca gaa acg ctg att     48
Met Trp Phe Gly Glu Phe Gly Gly Gln Tyr Val Pro Glu Thr Leu Ile
1               5                   10                  15 gga ccc ctg aaa gag ctg gaa aaa gct tac aaa cgt ttc aaa gat gac     96
Gly Pro Leu Lys Glu Leu Glu Lys Ala Tyr Lys Arg Phe Lys Asp Asp
            20                  25                  30 gaa gaa ttc aat cgt caa ctg aat tac tac ctg aaa acc tgg gca ggt    144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt    192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca    240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg    288
His Lys Thr Asn Asn Ala Ile Gly Gln Ala Leu Leu Ala Lys Leu Met
                85                  90                  95 ggt aaa act cgt ctg atc gct gag acc ggt gct ggt cag cac ggc gta    336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac    384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg    432
Met Gly Ala Glu Asp Val Glu Arg Gln Lys Met Asn Val Phe Arg Met
    130                 135                 140
```

| | | |
|---|---|---|
| aag ctg ctg ggt gca aac gta att cca gtt aac tcc ggt tct cgc acc<br>Lys Leu Leu Gly Ala Asn Val Ile Pro Val Asn Ser Gly Ser Arg Thr<br>145                    150                 155               160 | | 480 |
| ctg aaa gac gca atc aac gag gct ctg cgt gat tgg gtg gct acc ttt<br>Leu Lys Asp Ala Ile Asn Glu Ala Leu Arg Asp Trp Val Ala Thr Phe<br>                 165                 170                 175 | | 528 |
| gaa tac acc cac tac cta atc ggt tcc gtg gtc ggt cca cat ccg tat<br>Glu Tyr Thr His Tyr Leu Ile Gly Ser Val Val Gly Pro His Pro Tyr<br>                 180                 185                 190 | | 576 |
| ccg acc atc gtt cgt gat ttt cag tct gtt atc ggt cgt gag gct aaa<br>Pro Thr Ile Val Arg Asp Phe Gln Ser Val Ile Gly Arg Glu Ala Lys<br>               195                 200                 205 | | 624 |
| gcg cag atc ctg gag gct gaa ggt cag ctg cca gat gta atc gtt gct<br>Ala Gln Ile Leu Glu Ala Glu Gly Gln Leu Pro Asp Val Ile Val Ala<br>210                    215                 220 | | 672 |
| tgt gtt ggt ggt ggc tct aac gcg atg ggt atc ttt tac ccg ttc gtg<br>Cys Val Gly Gly Gly Ser Asn Ala Met Gly Ile Phe Tyr Pro Phe Val<br>225                    230                 235               240 | | 720 |
| aac gac aaa aaa gtt aag ctg gtt ggc gtt gag gct ggt ggt aaa ggc<br>Asn Asp Lys Lys Val Lys Leu Val Gly Val Glu Ala Gly Gly Lys Gly<br>                 245                 250                 255 | | 768 |
| ctg gaa tct ggt aag cat tcc gct agc ctg aac gca ggt cag gtt ggt<br>Leu Glu Ser Gly Lys His Ser Ala Ser Leu Asn Ala Gly Gln Val Gly<br>                 260                 265                 270 | | 816 |
| gtg tcc cat ggc atg ctg tcc tac ttt ctg cag gac gaa gaa ggt cag<br>Val Ser His Gly Met Leu Ser Tyr Phe Leu Gln Asp Glu Glu Gly Gln<br>                 275                 280                 285 | | 864 |
| atc aaa cca agc cac tcc atc gca cca ggt ctg gat tat cca ggt gtt<br>Ile Lys Pro Ser His Ser Ile Ala Pro Gly Leu Asp Tyr Pro Gly Val<br>290                    295                 300 | | 912 |
| ggt cca gaa cac gct tac ctg aaa aaa att cag cgt gct gaa tac gtg<br>Gly Pro Glu His Ala Tyr Leu Lys Lys Ile Gln Arg Ala Glu Tyr Val<br>305                    310                 315               320 | | 960 |
| gct gta acc gat gaa gaa gca ctg aaa gcg ttc cat gaa ctg agc cgt<br>Ala Val Thr Asp Glu Glu Ala Leu Lys Ala Phe His Glu Leu Ser Arg<br>                 325                 330                 335 | | 1008 |
| acc gaa ggt atc atc cca gct ctg gaa tct gcg cat gct gtg gct tac<br>Thr Glu Gly Ile Ile Pro Ala Leu Glu Ser Ala His Ala Val Ala Tyr<br>                 340                 345                 350 | | 1056 |
| gct atg aaa ctg gct aag gaa atg tct cgt gat gag atc atc atc gta<br>Ala Met Lys Leu Ala Lys Glu Met Ser Arg Asp Glu Ile Ile Ile Val<br>                 355                 360                 365 | | 1104 |
| aac ctg tct ggt cgt ggt gac aaa gac ctg gat att gtt ctg aaa gtg<br>Asn Leu Ser Gly Arg Gly Asp Lys Asp Leu Asp Ile Val Leu Lys Val<br>370                    375                 380 | | 1152 |
| tct ggc aac gtg ctc gag cac cat cac cat cac cat tga<br>Ser Gly Asn Val Leu Glu His His His His His His<br>385                    390                 395 | | 1191 |

<210> SEQ ID NO 14
<211> LENGTH: 396
<212> TYPE: PRT
<213> ORGANISM: Artificial Sequence
<220> FEATURE:
<223> OTHER INFORMATION: Synthetic Construct

<400> SEQUENCE: 14

Met Trp Phe Gly Glu Phe Gly Gly Gln Tyr Val Pro Glu Thr Leu Ile
1                 5                    10                  15

Gly Pro Leu Lys Glu Leu Glu Lys Ala Tyr Lys Arg Phe Lys Asp Asp
                 20                 25                 30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
    50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Leu Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
            115                 120                 125

Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
            195                 200                 205

Ala Gln Ile Leu Glu Ala Glu Gly Gln Leu Pro Asp Val Ile Val Ala
            210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
            275                 280                 285

Ile Lys Pro Ser His Ser Ile Ala Pro Gly Leu Asp Tyr Pro Gly Val
            290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
            355                 360                 365

Asn Leu Ser Gly Arg Gly Asp Lys Asp Leu Asp Ile Val Leu Lys Val
            370                 375                 380

Ser Gly Asn Val Leu Glu His His His His His
385                 390                 395

<210> SEQ ID NO 15
<211> LENGTH: 1191
<212> TYPE: DNA
<213> ORGANISM: Artificial Sequence
<220> FEATURE:
<223> OTHER INFORMATION: PfTrpB4D11
<220> FEATURE:
<221> NAME/KEY: CDS

<222> LOCATION: (1)..(1191)

<400> SEQUENCE: 15

```
atg tgg ttc ggt gaa ttt ggt ggt cag tac gtg cca gaa acg ctg att        48
Met Trp Phe Gly Glu Phe Gly Gly Gln Tyr Val Pro Glu Thr Leu Ile
1               5                   10                  15 gga ccc ctg aaa gag ctg gaa aaa gct tac aaa cgt ttc aaa gat gac        96
Gly Pro Leu Lys Glu Leu Glu Lys Ala Tyr Lys Arg Phe Lys Asp Asp
            20                  25                  30 gaa gaa ttc aat cgt caa ctg aat tac tac ctg aaa acc tgg gca ggt       144
Glu Glu Phe Asn Arg Gln Leu Asn Tyr Tyr Leu Lys Thr Trp Ala Gly
        35                  40                  45 cgt cca acc cca ctg tac tac gca aaa cgc ctg act gaa aaa atc ggt       192
Arg Pro Thr Pro Leu Tyr Tyr Ala Lys Arg Leu Thr Glu Lys Ile Gly
    50                  55                  60 ggt gct aaa gtc tac ctg aaa cgt gaa gac ctg gtt cac ggt ggt gca       240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ttc atg       288
His Lys Thr Asn Asn Ala Ile Gly Gln Ala Leu Leu Ala Lys Phe Met
                85                  90                  95 ggt aaa act cgt ctg atc gct gag acc ggt gct ggt cag cac ggc gta       336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac       384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg       432
Met Gly Ala Glu Asp Val Glu Arg Gln Lys Met Asn Val Phe Arg Met
    130                 135                 140 aag ctg ctg ggt gca aac gta att cca gtt aac tcc ggt tct cgc acc       480
Lys Leu Leu Gly Ala Asn Val Ile Pro Val Asn Ser Gly Ser Arg Thr
145                 150                 155                 160 ctg aaa gac gca atc aac gag gct ctg cgt gat tgg gtg gct act ttt       528
Leu Lys Asp Ala Ile Asn Glu Ala Leu Arg Asp Trp Val Ala Thr Phe
                165                 170                 175 gaa tac acc cac tac cta atc ggt tcc gtg gtc ggt cca cat ccg tat       576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa       624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct       672
Ala Gln Ile Leu Glu Ala Glu Gly Gln Leu Pro Asp Val Ile Val Ala
    210                 215                 220 tgt gtt ggt ggt ggc tct aac gcg atg ggt atc ttt tac ccg ttc gtg       720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc       768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt       816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag       864
Val Ser His Gly Met Leu Ser Tyr Phe Leu Gln Asp Glu Glu Gly Gln
        275                 280                 285 atc aaa cca agc cac tcc atc gca cca ggt ctg gat tat cca ggt gtt       912
Ile Lys Pro Ser His Ser Ile Ala Pro Gly Leu Asp Tyr Pro Gly Val
    290                 295                 300
```

```
ggt cca gaa cac gct tac ctg aaa aaa att cag cgt gct gaa tac gtg        960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt       1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac      1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta      1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg      1152
Asn Leu Ser Gly Arg Gly Asp Lys Asp Leu Asp Ile Val Leu Lys Val
    370                 375                 380 tct ggc aac gtg ctc gag cac cat cac cat cac cat tga                  1191
Ser Gly Asn Val Leu Glu His His His His His His
385                 390                 395
```

<210> SEQ ID NO 16
<211> LENGTH: 396
<212> TYPE: PRT
<213> ORGANISM: Artificial Sequence
<220> FEATURE:
<223> OTHER INFORMATION: Synthetic Construct

<400> SEQUENCE: 16

```
Met Trp Phe Gly Glu Phe Gly Gly Gln Tyr Val Pro Glu Thr Leu Ile
1               5                   10                  15

Gly Pro Leu Lys Glu Leu Glu Lys Ala Tyr Lys Arg Phe Lys Asp Asp
                20                  25                  30

Glu Glu Phe Asn Arg Gln Leu Asn Tyr Tyr Leu Lys Thr Trp Ala Gly
            35                  40                  45

Arg Pro Thr Pro Leu Tyr Tyr Ala Lys Arg Leu Thr Glu Lys Ile Gly
        50                  55                  60

Gly Ala Lys Val Tyr Leu Lys Arg Glu Asp Leu Val His Gly Gly Ala
65                  70                  75                  80

His Lys Thr Asn Asn Ala Ile Gly Gln Ala Leu Leu Ala Lys Phe Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240
```

```
Asn Asp Lys Lys Val Lys Leu Val Gly Val Glu Ala Gly Gly Lys Gly
            245                 250                 255

Leu Glu Ser Gly Lys His Ser Ala Ser Leu Asn Ala Gly Gln Val Gly
        260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
        290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Val
        370                 375                 380

Ser Gly Asn Val Leu Glu His His His His His His
385                 390                 395

<210> SEQ ID NO 17
<211> LENGTH: 1191
<212> TYPE: DNA
<213> ORGANISM: Artificial Sequence
<220> FEATURE:
<223> OTHER INFORMATION: PfTrpB2B9
<220> FEATURE:
<221> NAME/KEY: CDS
<222> LOCATION: (1)..(1191)

<400> SEQUENCE: 17 atg tgg ttc ggt gaa ttt ggt ggt cag tac gtg cca gaa acg ctg gtt      48
Met Trp Phe Gly Glu Phe Gly Gly Gln Tyr Val Pro Glu Thr Leu Val
1               5                   10                  15 gga ccc ctg aaa gag ctg gaa aaa gct tac aaa cgt ttc aaa gat gac      96
Gly Pro Leu Lys Glu Leu Glu Lys Ala Tyr Lys Arg Phe Lys Asp Asp
                20                  25                  30 gaa gaa ttc aat cgt cag ctg aat tac tac ctg aaa acc tgg gca ggt     144
Glu Glu Phe Asn Arg Gln Leu Asn Tyr Tyr Leu Lys Thr Trp Ala Gly
            35                  40                  45 cgt cca acc cca ctg tac tac gca aaa cgc ctg act gaa aaa atc ggt     192
Arg Pro Thr Pro Leu Tyr Tyr Ala Lys Arg Leu Thr Glu Lys Ile Gly
        50                  55                  60 ggt gct aaa gtc tac ctg aaa cgt gaa gac ctg gtt cac ggt ggt gca     240
Gly Ala Lys Val Tyr Leu Lys Arg Glu Asp Leu Val His Gly Gly Ala
65                  70                  75                  80 cac aag acc aac aac gcc atc ggt cag gca ctg ctg gca aag ctc atg     288
His Lys Thr Asn Asn Ala Ile Gly Gln Ala Leu Leu Ala Lys Leu Met
                85                  90                  95 ggt aaa act cgt ctg atc gct gag acc ggt gct ggt cag cac ggc gta     336
Gly Lys Thr Arg Leu Ile Ala Glu Thr Gly Ala Gly Gln His Gly Val
            100                 105                 110 gcg act gca atg gct ggt gca ctg ctg ggc atg aaa gtg gac att tac     384
Ala Thr Ala Met Ala Gly Ala Leu Leu Gly Met Lys Val Asp Ile Tyr
        115                 120                 125 atg ggt gct gag gac gta gaa cgt cag aaa atg aac gta ttc cgt atg     432
Met Gly Ala Glu Asp Val Glu Arg Gln Lys Met Asn Val Phe Arg Met
        130                 135                 140
```

```
aag ctg ctg ggt gca aac gta att cca gtt aac tcc ggt tct cgc acc       480
Lys Leu Leu Gly Ala Asn Val Ile Pro Val Asn Ser Gly Ser Arg Thr
145                 150                 155                 160 ctg aaa gac gca atc aac gag gct ctg cgt gat tgg gtg gct act ttt       528
Leu Lys Asp Ala Ile Asn Glu Ala Leu Arg Asp Trp Val Ala Thr Phe
                165                 170                 175 gaa tac acc cac tac cta atc ggt tcc gtg gtc ggt cca cat ccg tat       576
Glu Tyr Thr His Tyr Leu Ile Gly Ser Val Val Gly Pro His Pro Tyr
            180                 185                 190 ccg acc atc gtt cgt gat ttt cag tct gtt atc ggt cgt gag gct aaa       624
Pro Thr Ile Val Arg Asp Phe Gln Ser Val Ile Gly Arg Glu Ala Lys
        195                 200                 205 gcg cag atc ctg gag gct gaa ggt cag ctg cca gat gta atc gtt gct       672
Ala Gln Ile Leu Glu Ala Glu Gly Gln Leu Pro Asp Val Ile Val Ala
210                 215                 220 tgt gtt ggt ggt ggc tct aac gcg atg ggt atc ttt tac ccg ttc gtg       720
Cys Val Gly Gly Gly Ser Asn Ala Met Gly Ile Phe Tyr Pro Phe Val
225                 230                 235                 240 aac gac aaa aaa gtt aag ctg gtt ggc gtt gag gct ggt ggt aaa ggc       768
Asn Asp Lys Lys Val Lys Leu Val Gly Val Glu Ala Gly Gly Lys Gly
                245                 250                 255 ctg gaa tct ggt aag cat tcc gct agc ctg aac gca ggt cag gtt ggt       816
Leu Glu Ser Gly Lys His Ser Ala Ser Leu Asn Ala Gly Gln Val Gly
            260                 265                 270 gtg tcc cat ggc atg ctg tcc tac ttt ctg cag gac gaa gaa ggt cag       864
Val Ser His Gly Met Leu Ser Tyr Phe Leu Gln Asp Glu Glu Gly Gln
        275                 280                 285 atc aaa cca agc cac tcc atc gca cca ggt ctg gat tat cca ggt gtt       912
Ile Lys Pro Ser His Ser Ile Ala Pro Gly Leu Asp Tyr Pro Gly Val
290                 295                 300 ggt cca gaa cac gct tac ctg aaa aaa att cag cgt gct gaa tac gtg       960
Gly Pro Glu His Ala Tyr Leu Lys Lys Ile Gln Arg Ala Glu Tyr Val
305                 310                 315                 320 gct gta acc gat gaa gaa gca ctg aaa gcg ttc cat gaa ctg agc cgt      1008
Ala Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac      1056
Thr Glu Gly Ile Ile Pro Ala Leu Glu Ser Ala His Ala Val Ala Tyr
            340                 345                 350 gct atg aaa ctg gct aag gaa atg tcg cgt gat gag atc atc atc gta      1104
Ala Met Lys Leu Ala Lys Glu Met Ser Arg Asp Glu Ile Ile Ile Val
        355                 360                 365 aac ctg tct ggt cgt ggt gac aaa gac ctg gat att gtc ctg aaa gcg      1152
Asn Leu Ser Gly Arg Gly Asp Lys Asp Leu Asp Ile Val Leu Lys Ala
370                 375                 380 tct ggc aac gtg ctc gag cac cac cac cac cac cac tga                  1191
Ser Gly Asn Val Leu Glu His His His His His His
385                 390                 395

<210> SEQ ID NO 18
<211> LENGTH: 396
<212> TYPE: PRT
<213> ORGANISM: Artificial Sequence
<220> FEATURE:
<223> OTHER INFORMATION: Synthetic Construct

<400> SEQUENCE: 18

Met Trp Phe Gly Glu Phe Gly Gly Gln Tyr Val Pro Glu Thr Leu Val
1               5                   10                  15

Gly Pro Leu Lys Glu Leu Glu Lys Ala Tyr Lys Arg Phe Lys Asp Asp
```

```
            20                  25                  30
Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
 50                  55                  60

Gly Ala Lys Val Tyr Leu Lys Arg Glu Asp Leu Val His Gly Gly Ala
 65                  70                  75                  80

His Lys Thr Asn Asn Ala Ile Gly Gln Ala Leu Leu Ala Lys Leu Met
                 85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Met
    130                 135                 140

Lys Leu Leu Gly Ala Asn Val Ile Pro Val Asn Ser Gly Ser Arg Thr
145                 150                 155                 160

Leu Lys Asp Ala Ile Asn Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
225                 230                 235                 240

Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
            260                 265                 270

Val Ser His Gly Met Leu Ser Tyr Phe Leu Gln Asp Glu Glu Gly Gln
        275                 280                 285

Ile Lys Pro Ser His Ser Ile Ala Pro Gly Leu Asp Tyr Pro Gly Val
    290                 295                 300

Gly Pro Glu His Ala Tyr Leu Lys Lys Ile Gln Arg Ala Glu Tyr Val
305                 310                 315                 320

Ala Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Ala
    370                 375                 380

Ser Gly Asn Val Leu Glu His His His His His
385                 390                 395

<210> SEQ ID NO 19
<211> LENGTH: 1191
<212> TYPE: DNA
<213> ORGANISM: Artificial Sequence
<220> FEATURE:
<223> OTHER INFORMATION: PfTrpBM144TN166D
<220> FEATURE:
```

<221> NAME/KEY: CDS
<222> LOCATION: (1)..(1191)

<400> SEQUENCE: 19

| | | | | | | | | | | | | | | | | |
|---|---|---|---|---|---|---|---|---|---|---|---|---|---|---|---|---|
| atg | tgg | ttc | ggt | gaa | ttt | ggt | ggt | cag | tac | gtg | cca | gaa | acg | ctg | att | 48 |
| Met | Trp | Phe | Gly | Glu | Phe | Gly | Gly | Gln | Tyr | Val | Pro | Glu | Thr | Leu | Ile | |
| 1 | | | | 5 | | | | | 10 | | | | | 15 | | |
| gaa | ccg | ctg | aaa | gag | ctg | gaa | aaa | gct | tac | aaa | cgt | ttc | aaa | gat | gac | 96 |
| Glu | Pro | Leu | Lys | Glu | Leu | Glu | Lys | Ala | Tyr | Lys | Arg | Phe | Lys | Asp | Asp | |
| | | | 20 | | | | | 25 | | | | | 30 | | | |
| gaa | gaa | ttc | aat | cgt | caa | ctg | aat | tac | tac | ctg | aaa | acc | tgg | gca | ggt | 144 |
| Glu | Glu | Phe | Asn | Arg | Gln | Leu | Asn | Tyr | Tyr | Leu | Lys | Thr | Trp | Ala | Gly | |
| | 35 | | | | | 40 | | | | | 45 | | | | | |
| cgt | cca | acc | cca | ctg | tac | tac | gca | aaa | cgc | ctg | act | gaa | aaa | atc | ggt | 192 |
| Arg | Pro | Thr | Pro | Leu | Tyr | Tyr | Ala | Lys | Arg | Leu | Thr | Glu | Lys | Ile | Gly | |
| 50 | | | | | 55 | | | | | 60 | | | | | | |
| ggt | gct | aaa | atc | tac | ctg | aaa | cgt | gaa | gac | ctg | gtt | cac | ggt | ggt | gca | 240 |
| Gly | Ala | Lys | Ile | Tyr | Leu | Lys | Arg | Glu | Asp | Leu | Val | His | Gly | Gly | Ala | |
| 65 | | | | 70 | | | | | 75 | | | | | 80 | | |
| cac | aag | acc | aac | aac | gcc | atc | ggt | cag | gca | ctg | ctg | gca | aag | ttc | atg | 288 |
| His | Lys | Thr | Asn | Asn | Ala | Ile | Gly | Gln | Ala | Leu | Leu | Ala | Lys | Phe | Met | |
| | | | | 85 | | | | | 90 | | | | | 95 | | |
| ggt | aaa | act | cgt | ctg | atc | gct | gag | acc | ggt | gct | ggt | cag | cac | ggc | gta | 336 |
| Gly | Lys | Thr | Arg | Leu | Ile | Ala | Glu | Thr | Gly | Ala | Gly | Gln | His | Gly | Val | |
| | | 100 | | | | | 105 | | | | | 110 | | | | |
| gcg | act | gca | atg | gct | ggt | gca | ctg | ctg | ggc | atg | aaa | gtg | gac | att | tac | 384 |
| Ala | Thr | Ala | Met | Ala | Gly | Ala | Leu | Leu | Gly | Met | Lys | Val | Asp | Ile | Tyr | |
| | | 115 | | | | | 120 | | | | | 125 | | | | |
| atg | ggt | gct | gag | gac | gta | gaa | cgt | cag | aaa | atg | aac | gta | ttc | cgt | acg | 432 |
| Met | Gly | Ala | Glu | Asp | Val | Glu | Arg | Gln | Lys | Met | Asn | Val | Phe | Arg | Thr | |
| | 130 | | | | | 135 | | | | | 140 | | | | | |
| aag | ctg | ctg | ggt | gca | aac | gta | att | cca | gtt | aac | tcc | ggt | tct | cgc | acc | 480 |
| Lys | Leu | Leu | Gly | Ala | Asn | Val | Ile | Pro | Val | Asn | Ser | Gly | Ser | Arg | Thr | |
| 145 | | | | | 150 | | | | | 155 | | | | | 160 | |
| ctg | aaa | gac | gca | atc | gac | gag | gct | ctg | cgt | gat | tgg | gtg | gct | act | ttt | 528 |
| Leu | Lys | Asp | Ala | Ile | Asp | Glu | Ala | Leu | Arg | Asp | Trp | Val | Ala | Thr | Phe | |
| | | | | 165 | | | | | 170 | | | | | 175 | | |
| gaa | tac | acc | cac | tac | ctg | atc | ggt | tcc | gtg | gtc | ggt | cca | cat | ccg | tat | 576 |
| Glu | Tyr | Thr | His | Tyr | Leu | Ile | Gly | Ser | Val | Val | Gly | Pro | His | Pro | Tyr | |
| | | | 180 | | | | | 185 | | | | | 190 | | | |
| ccg | acc | atc | gtt | cgt | gat | ttt | cag | tct | gtt | atc | ggt | cgt | gag | gct | aaa | 624 |
| Pro | Thr | Ile | Val | Arg | Asp | Phe | Gln | Ser | Val | Ile | Gly | Arg | Glu | Ala | Lys | |
| | | 195 | | | | | 200 | | | | | 205 | | | | |
| gcg | cag | atc | ctg | gag | gct | gaa | ggt | cag | ctg | cca | gat | gta | atc | gtt | gct | 672 |
| Ala | Gln | Ile | Leu | Glu | Ala | Glu | Gly | Gln | Leu | Pro | Asp | Val | Ile | Val | Ala | |
| | 210 | | | | | 215 | | | | | 220 | | | | | |
| tgt | gtt | ggt | ggt | ggc | tct | aac | gcg | atg | ggt | atc | ttt | tac | ccg | ttc | gtg | 720 |
| Cys | Val | Gly | Gly | Gly | Ser | Asn | Ala | Met | Gly | Ile | Phe | Tyr | Pro | Phe | Val | |
| 225 | | | | | 230 | | | | | 235 | | | | | 240 | |
| aac | gac | aaa | aaa | gtt | aag | ctg | gtt | ggc | gtt | gag | gct | ggt | ggt | aaa | ggc | 768 |
| Asn | Asp | Lys | Lys | Val | Lys | Leu | Val | Gly | Val | Glu | Ala | Gly | Gly | Lys | Gly | |
| | | | | 245 | | | | | 250 | | | | | 255 | | |
| ctg | gaa | tct | ggt | aag | cat | tcc | gct | agc | ctg | aac | gca | ggt | cag | gtt | ggt | 816 |
| Leu | Glu | Ser | Gly | Lys | His | Ser | Ala | Ser | Leu | Asn | Ala | Gly | Gln | Val | Gly | |
| | | | 260 | | | | | 265 | | | | | 270 | | | |
| gtg | ttc | cat | ggc | atg | ctg | tcc | tac | ttt | ctg | cag | gac | gaa | gaa | ggt | cag | 864 |
| Val | Phe | His | Gly | Met | Leu | Ser | Tyr | Phe | Leu | Gln | Asp | Glu | Glu | Gly | Gln | |
| | | 275 | | | | | 280 | | | | | 285 | | | | |
| atc | aaa | cca | act | cac | tcc | atc | gca | cca | ggt | ctg | gat | tat | cca | ggt | gtt | 912 |
| Ile | Lys | Pro | Thr | His | Ser | Ile | Ala | Pro | Gly | Leu | Asp | Tyr | Pro | Gly | Val | |

```
                290                 295                 300
ggt cca gaa cac gct tac ctg aaa aaa att cag cgt gct gaa tac gtg      960
Gly Pro Glu His Ala Tyr Leu Lys Lys Ile Gln Arg Ala Glu Tyr Val
305                 310                 315                 320 act gta acc gat gaa gaa gca ctg aaa gcg ttc cat gaa ctg agc cgt     1008
Thr Val Thr Asp Glu Glu Ala Leu Lys Ala Phe His Glu Leu Ser Arg
                325                 330                 335 acc gaa ggt atc atc cca gct ctg gaa tct gcg cat gct gtg gct tac     1056
Thr Glu Gly Ile Ile Pro Ala Leu Glu Ser Ala His Ala Val Ala Tyr
            340                 345                 350 gct atg aaa ctg gct aag gaa atg tct cgt gat gag atc atc atc gta     1104
Ala Met Lys Leu Ala Lys Glu Met Ser Arg Asp Glu Ile Ile Ile Val
        355                 360                 365 aac ctg tct ggt cgt ggt gac aaa gac ctg gat att gtt ctg aaa gtg     1152
Asn Leu Ser Gly Arg Gly Asp Lys Asp Leu Asp Ile Val Leu Lys Val
370                 375                 380 tct ggc aac gtg ctc gag cac cac cac cac cac cac tga                 1191
Ser Gly Asn Val Leu Glu His His His His His His
385                 390                 395
```

<210> SEQ ID NO 20
<211> LENGTH: 396
<212> TYPE: PRT
<213> ORGANISM: Artificial Sequence
<220> FEATURE:
<223> OTHER INFORMATION: Synthetic Construct

<400> SEQUENCE: 20

```
Met Trp Phe Gly Glu Phe Gly Gly Gln Tyr Val Pro Glu Thr Leu Ile
1               5                   10                  15

Glu Pro Leu Lys Glu Leu Glu Lys Ala Tyr Lys Arg Phe Lys Asp Asp
            20                  25                  30

Glu Glu Phe Asn Arg Gln Leu Asn Tyr Tyr Leu Lys Thr Trp Ala Gly
        35                  40                  45

Arg Pro Thr Pro Leu Tyr Tyr Ala Lys Arg Leu Thr Glu Lys Ile Gly
    50                  55                  60

Gly Ala Lys Ile Tyr Leu Lys Arg Glu Asp Leu Val His Gly Gly Ala
65                  70                  75                  80

His Lys Thr Asn Asn Ala Ile Gly Gln Ala Leu Leu Ala Lys Phe Met
                85                  90                  95

Gly Lys Thr Arg Leu Ile Ala Glu Thr Gly Ala Gly Gln His Gly Val
            100                 105                 110

Ala Thr Ala Met Ala Gly Ala Leu Leu Gly Met Lys Val Asp Ile Tyr
        115                 120                 125

Met Gly Ala Glu Asp Val Glu Arg Gln Lys Met Asn Val Phe Arg Thr
    130                 135                 140

Lys Leu Leu Gly Ala Asn Val Ile Pro Val Asn Ser Gly Ser Arg Thr
145                 150                 155                 160

Leu Lys Asp Ala Ile Asp Glu Ala Leu Arg Asp Trp Val Ala Thr Phe
                165                 170                 175

Glu Tyr Thr His Tyr Leu Ile Gly Ser Val Val Gly Pro His Pro Tyr
            180                 185                 190

Pro Thr Ile Val Arg Asp Phe Gln Ser Val Ile Gly Arg Glu Ala Lys
        195                 200                 205

Ala Gln Ile Leu Glu Ala Glu Gly Gln Leu Pro Asp Val Ile Val Ala
    210                 215                 220

Cys Val Gly Gly Gly Ser Asn Ala Met Gly Ile Phe Tyr Pro Phe Val
```

```
                    225                 230                 235                 240
Asn Asp Lys Lys Val Lys Leu Val Gly Val Glu Ala Gly Gly Lys Gly
                245                 250                 255

Leu Glu Ser Gly Lys His Ser Ala Ser Leu Asn Ala Gly Gln Val Gly
                260                 265                 270

Val Phe His Gly Met Leu Ser Tyr Phe Leu Gln Asp Glu Glu Gly Gln
            275                 280                 285

Ile Lys Pro Thr His Ser Ile Ala Pro Gly Leu Asp Tyr Pro Gly Val
        290                 295                 300

Gly Pro Glu His Ala Tyr Leu Lys Lys Ile Gln Arg Ala Glu Tyr Val
305                 310                 315                 320

Thr Val Thr Asp Glu Glu Ala Leu Lys Ala Phe His Glu Leu Ser Arg
                325                 330                 335

Thr Glu Gly Ile Ile Pro Ala Leu Glu Ser Ala His Ala Val Ala Tyr
            340                 345                 350

Ala Met Lys Leu Ala Lys Glu Met Ser Arg Asp Glu Ile Ile Ile Val
        355                 360                 365

Asn Leu Ser Gly Arg Gly Asp Lys Asp Leu Asp Ile Val Leu Lys Val
    370                 375                 380

Ser Gly Asn Val Leu Glu His His His His His His
385                 390                 395

<210> SEQ ID NO 21
<211> LENGTH: 1218
<212> TYPE: DNA
<213> ORGANISM: Artificial Sequence
<220> FEATURE:
<223> OTHER INFORMATION: AfTrpB0B2
<220> FEATURE:
<221> NAME/KEY: CDS
<222> LOCATION: (1)..(1218)

<400> SEQUENCE: 21 atg cgt tgc tgg ctg gaa aac ctg tct ggc ggt cgt aaa atg aag ttt         48
Met Arg Cys Trp Leu Glu Asn Leu Ser Gly Gly Arg Lys Met Lys Phe
1               5                   10                  15 ggt gag ttt ggc ggt cgt ttc gtt ctg gag gta ctg atc gga ccg ctg         96
Gly Glu Phe Gly Gly Arg Phe Val Leu Glu Val Leu Ile Gly Pro Leu
                20                  25                  30 gaa gaa ctg gaa aaa gca tac gac cgc ttt aaa gat gat gag gaa ttt        144
Glu Glu Leu Glu Lys Ala Tyr Asp Arg Phe Lys Asp Asp Glu Glu Phe
            35                  40                  45 aaa gca cgt ctg gaa tac tac ctg aaa tcc tat gca ggt cgt ccg acc        192
Lys Ala Arg Leu Glu Tyr Tyr Leu Lys Ser Tyr Ala Gly Arg Pro Thr
        50                  55                  60 cca ctg tac ttc gct gag aac ctg agc cgt gaa ctg ggc gtc aaa gtc        240
Pro Leu Tyr Phe Ala Glu Asn Leu Ser Arg Glu Leu Gly Val Lys Val
65                  70                  75                  80 tat ctg aaa cgc gaa gac ctg ctg cat ggt ggt gcg cac aaa atc aac        288
Tyr Leu Lys Arg Glu Asp Leu Leu His Gly Gly Ala His Lys Ile Asn
                85                  90                  95 aat acc atc ggt caa gcg ctg ctg gcg aaa ttc atg ggt aaa aag cgt        336
Asn Thr Ile Gly Gln Ala Leu Leu Ala Lys Phe Met Gly Lys Lys Arg
            100                 105                 110 gtt att gcg gaa acc ggt gca ggt cag cac ggt gtg gcg act gcg atg        384
Val Ile Ala Glu Thr Gly Ala Gly Gln His Gly Val Ala Thr Ala Met
        115                 120                 125 gct gcg gca ctg ctg ggc ctg gaa gcg gaa att tat atg ggt gct gaa        432
Ala Ala Ala Leu Leu Gly Leu Glu Ala Glu Ile Tyr Met Gly Ala Glu
```

```
gac tat gag cgc caa aaa atg aac gtg ttt cgt atg gaa ctg ctg ggt      480
Asp Tyr Glu Arg Gln Lys Met Asn Val Phe Arg Met Glu Leu Leu Gly
145                 150                 155                 160 gcc aaa gtc acc gct gta gaa agc ggt tcc cgt acc ctg aaa gac gca      528
Ala Lys Val Thr Ala Val Glu Ser Gly Ser Arg Thr Leu Lys Asp Ala
                165                 170                 175 atc aac gag gca ctg cgt gac tgg gtg gaa tct ttc gaa cac act cac      576
Ile Asn Glu Ala Leu Arg Asp Trp Val Glu Ser Phe Glu His Thr His
            180                 185                 190 tac ctg atc ggt tct gta gta ggt ccg cat ccg ttc ccg act atc gtc      624
Tyr Leu Ile Gly Ser Val Val Gly Pro His Pro Phe Pro Thr Ile Val
        195                 200                 205 cgc gac ttc caa gct gtg atc ggc aag gag gca cgc gtt cag atc atc      672
Arg Asp Phe Gln Ala Val Ile Gly Lys Glu Ala Arg Arg Gln Ile Ile
    210                 215                 220 gaa gcg gaa ggt ggt atg ccg gat gct atc atc gcg tgc gta ggc ggt      720
Glu Ala Glu Gly Gly Met Pro Asp Ala Ile Ile Ala Cys Val Gly Gly
225                 230                 235                 240 ggc tcc aac gct atg ggc atc ttc cac ccg ttc ctg aac gac gac gta      768
Gly Ser Asn Ala Met Gly Ile Phe His Pro Phe Leu Asn Asp Asp Val
                245                 250                 255 cgt ctg att ggt gta gaa gct ggc ggt gaa ggt atc gaa tct ggt cgt      816
Arg Leu Ile Gly Val Glu Ala Gly Gly Glu Gly Ile Glu Ser Gly Arg
            260                 265                 270 cat tcc gca agc ctg acc gct ggc tct aaa ggt gtt tcg cac ggt atg      864
His Ser Ala Ser Leu Thr Ala Gly Ser Lys Gly Val Ser His Gly Met
        275                 280                 285 ctg agc tat ttc ctg cag gac gaa gag ggt atg atg ctg gac agc cat      912
Leu Ser Tyr Phe Leu Gln Asp Glu Glu Gly Met Met Leu Asp Ser His
    290                 295                 300 tcc gta tct gca ggt ctg gat tat ccg ggt gtt ggt ccg gaa cac gcc      960
Ser Val Ser Ala Gly Leu Asp Tyr Pro Gly Val Gly Pro Glu His Ala
305                 310                 315                 320 tac ctg aag gaa acg ggt cgt tgt gag tac gtt gcc gta aat gac gaa     1008
Tyr Leu Lys Glu Thr Gly Arg Cys Glu Tyr Val Ala Val Asn Asp Glu
                325                 330                 335 gaa gcg ctg cgt gct ttc aaa acc ctg tcc aaa ctg gaa ggt atc att     1056
Glu Ala Leu Arg Ala Phe Lys Thr Leu Ser Lys Leu Glu Gly Ile Ile
            340                 345                 350 cct gcg ctg gaa tcc gct cac gcc att gca tac gct atg aaa atg gcc     1104
Pro Ala Leu Glu Ser Ala His Ala Ile Ala Tyr Ala Met Lys Met Ala
        355                 360                 365 gag gaa atg cag cgt gat gat gtg ctg gtt gta aac ctg tcc ggt cgt     1152
Glu Glu Met Gln Arg Asp Asp Val Leu Val Val Asn Leu Ser Gly Arg
    370                 375                 380 ggc gat aaa gat atg gac atc gta cgt cgt cgt ctg gct ctc gag cac     1200
Gly Asp Lys Asp Met Asp Ile Val Arg Arg Arg Leu Ala Leu Glu His
385                 390                 395                 400 cac cac cac cac tga                                                  1218
His His His His His
                405

<210> SEQ ID NO 22
<211> LENGTH: 405
<212> TYPE: PRT
<213> ORGANISM: Artificial Sequence
<220> FEATURE:
<223> OTHER INFORMATION: Synthetic Construct

<400> SEQUENCE: 22
```

```
Met Arg Cys Trp Leu Glu Asn Leu Ser Gly Gly Arg Lys Met Lys Phe
1               5                   10                  15
Gly Glu Phe Gly Gly Arg Phe Val Leu Glu Val Leu Ile Gly Pro Leu
                20                  25                  30
Glu Glu Leu Glu Lys Ala Tyr Asp Arg Phe Lys Asp Asp Glu Glu Phe
            35                  40                  45
Lys Ala Arg Leu Glu Tyr Tyr Leu Lys Ser Tyr Ala Gly Arg Pro Thr
50                      55                  60
Pro Leu Tyr Phe Ala Glu Asn Leu Ser Arg Glu Leu Gly Val Lys Val
65                      70                  75                  80
Tyr Leu Lys Arg Glu Asp Leu Leu His Gly Ala His Lys Ile Asn
                85                  90                  95
Asn Thr Ile Gly Gln Ala Leu Leu Ala Lys Phe Met Gly Lys Lys Arg
                100                 105                 110
Val Ile Ala Glu Thr Gly Ala Gly Gln His Gly Val Ala Thr Ala Met
            115                 120                 125
Ala Ala Ala Leu Leu Gly Leu Glu Ala Glu Ile Tyr Met Gly Ala Glu
        130                 135                 140
Asp Tyr Glu Arg Gln Lys Met Asn Val Phe Arg Met Glu Leu Leu Gly
145                 150                 155                 160
Ala Lys Val Thr Ala Val Glu Ser Gly Ser Arg Thr Leu Lys Asp Ala
            165                 170                 175
Ile Asn Glu Ala Leu Arg Asp Trp Val Glu Ser Phe Glu His Thr His
        180                 185                 190
Tyr Leu Ile Gly Ser Val Val Gly Pro His Pro Phe Pro Thr Ile Val
        195                 200                 205
Arg Asp Phe Gln Ala Val Ile Gly Lys Glu Ala Arg Arg Gln Ile Ile
210                 215                 220
Glu Ala Glu Gly Gly Met Pro Asp Ala Ile Ile Ala Cys Val Gly Gly
225                 230                 235                 240
Gly Ser Asn Ala Met Gly Ile Phe His Pro Phe Leu Asn Asp Asp Val
                245                 250                 255
Arg Leu Ile Gly Val Glu Ala Gly Gly Glu Gly Ile Glu Ser Gly Arg
            260                 265                 270
His Ser Ala Ser Leu Thr Ala Gly Ser Lys Gly Val Ser His Gly Met
        275                 280                 285
Leu Ser Tyr Phe Leu Gln Asp Glu Glu Gly Met Met Leu Asp Ser His
        290                 295                 300
Ser Val Ser Ala Gly Leu Asp Tyr Pro Gly Val Gly Pro Glu His Ala
305                 310                 315                 320
Tyr Leu Lys Glu Thr Gly Arg Cys Glu Tyr Val Ala Val Asn Asp Glu
                325                 330                 335
Glu Ala Leu Arg Ala Phe Lys Thr Leu Ser Lys Leu Glu Gly Ile Ile
            340                 345                 350
Pro Ala Leu Glu Ser Ala His Ala Ile Ala Tyr Ala Met Lys Met Ala
        355                 360                 365
Glu Glu Met Gln Arg Asp Asp Val Leu Val Val Asn Leu Ser Gly Arg
        370                 375                 380
Gly Asp Lys Asp Met Asp Ile Val Arg Arg Arg Leu Ala Leu Glu His
385                 390                 395                 400
His His His His His
                405
```

<210> SEQ ID NO 23
<211> LENGTH: 1218
<212> TYPE: DNA
<213> ORGANISM: Artificial Sequence
<220> FEATURE:
<223> OTHER INFORMATION: AfTrpBM156TN178D
<220> FEATURE:
<221> NAME/KEY: CDS
<222> LOCATION: (1)..(1218)

<400> SEQUENCE: 23

```
atg cgt tgc tgg ctg gaa aac ctg tct ggc ggt cgt aaa atg aag ttt      48
Met Arg Cys Trp Leu Glu Asn Leu Ser Gly Gly Arg Lys Met Lys Phe
1               5                   10                  15 ggt gag ttt ggc ggt cgt ttc gtt ccg gag gta ctg atc cca ccg ctg      96
Gly Glu Phe Gly Gly Arg Phe Val Pro Glu Val Leu Ile Pro Pro Leu
                20                  25                  30 gaa gaa ctg gaa aaa gca tac gac cgc ttt aaa gat gat gag gaa ttt     144
Glu Glu Leu Glu Lys Ala Tyr Asp Arg Phe Lys Asp Asp Glu Glu Phe
            35                  40                  45 aaa gca cgt ctg gaa tac tac ctg aaa tcc tat gca ggt cgt ccg acc     192
Lys Ala Arg Leu Glu Tyr Tyr Leu Lys Ser Tyr Ala Gly Arg Pro Thr
        50                  55                  60 cca ctg tac ttc gct gag aac ctg agc cgt gaa ctg ggc gtc aaa atc     240
Pro Leu Tyr Phe Ala Glu Asn Leu Ser Arg Glu Leu Gly Val Lys Ile
65                  70                  75                  80 tat ctg aaa cgc gaa gac ctg ctg cat ggt ggt gcg cac aaa atc aac     288
Tyr Leu Lys Arg Glu Asp Leu Leu His Gly Gly Ala His Lys Ile Asn
                85                  90                  95 aat acc atc ggt caa gcg ctg ctg gcg aaa ttc atg ggt aaa aag cgt     336
Asn Thr Ile Gly Gln Ala Leu Leu Ala Lys Phe Met Gly Lys Lys Arg
            100                 105                 110 gtt att gcg gaa acc ggt gca ggt cag cac ggt gtg gcg act gcg atg     384
Val Ile Ala Glu Thr Gly Ala Gly Gln His Gly Val Ala Thr Ala Met
        115                 120                 125 gct gcg gca ctg ctg ggc ctg gaa gcg gaa att tat atg ggt gct gaa     432
Ala Ala Ala Leu Leu Gly Leu Glu Ala Glu Ile Tyr Met Gly Ala Glu
    130                 135                 140 gac tat gag cgc caa aaa atg aac gtg ttt cgt acg gaa ctg ctg ggt     480
Asp Tyr Glu Arg Gln Lys Met Asn Val Phe Arg Thr Glu Leu Leu Gly
145                 150                 155                 160 gcc aaa gtc acc gct gta gaa agc ggt tcc cgt acc ctg aaa gac gca     528
Ala Lys Val Thr Ala Val Glu Ser Gly Ser Arg Thr Leu Lys Asp Ala
                165                 170                 175 atc gac gag gca ctg cgt gac tgg gtg gaa tct ttc gaa cac act cac     576
Ile Asp Glu Ala Leu Arg Asp Trp Val Glu Ser Phe Glu His Thr His
            180                 185                 190 tac ctg atc ggt tct gta gta ggt ccg cat ccg ttc ccg act atc gtc     624
Tyr Leu Ile Gly Ser Val Val Gly Pro His Pro Phe Pro Thr Ile Val
        195                 200                 205 cgc gac ttc caa gct gtg atc ggc aag gag gca cgc cgt cag atc atc     672
Arg Asp Phe Gln Ala Val Ile Gly Lys Glu Ala Arg Arg Gln Ile Ile
    210                 215                 220 gaa gcg gaa ggt ggt atg ccg gat gct atc atc gcg tgc gta ggc ggt     720
Glu Ala Glu Gly Gly Met Pro Asp Ala Ile Ile Ala Cys Val Gly Gly
225                 230                 235                 240 ggc tcc aac gct atg ggc atc ttc cac ccg ttc ctg aac gac gac gta     768
Gly Ser Asn Ala Met Gly Ile Phe His Pro Phe Leu Asn Asp Asp Val
                245                 250                 255 cgt ctg att ggt gta gaa gct ggc ggt gaa ggt atc gaa tct ggt cgt     816
Arg Leu Ile Gly Val Glu Ala Gly Gly Glu Gly Ile Glu Ser Gly Arg
```

```
                     260                 265                 270
cat tcc gca agc ctg acc gct ggc tct aaa ggt gtt ctg cac ggt atg        864
His Ser Ala Ser Leu Thr Ala Gly Ser Lys Gly Val Leu His Gly Met
            275                 280                 285 ctg agc tat ttc ctg cag gac gaa gag ggt atg atg ctg gac acc cac        912
Leu Ser Tyr Phe Leu Gln Asp Glu Glu Gly Met Met Leu Asp Thr His
        290                 295                 300 tcc gta tct gca ggt ctg gat tat ccg ggt gtt ggt ccg gaa cac gcc        960
Ser Val Ser Ala Gly Leu Asp Tyr Pro Gly Val Gly Pro Glu His Ala
305                 310                 315                 320 tac ctg aag gaa acg ggt cgt tgt gag tac gtt acc gta aat gac gaa       1008
Tyr Leu Lys Glu Thr Gly Arg Cys Glu Tyr Val Thr Val Asn Asp Glu
                325                 330                 335 gaa gcg ctg cgt gct ttc aaa acc ctg tcc aaa ctg gaa ggt atc att       1056
Glu Ala Leu Arg Ala Phe Lys Thr Leu Ser Lys Leu Glu Gly Ile Ile
            340                 345                 350 cct gcg ctg gaa tcc gct cac gcc att gca tac gct atg aaa atg gcc       1104
Pro Ala Leu Glu Ser Ala His Ala Ile Ala Tyr Ala Met Lys Met Ala
        355                 360                 365 gag gaa atg cag cgt gat gat gtg ctg gtt gta aac ctg tcc ggt cgt       1152
Glu Glu Met Gln Arg Asp Asp Val Leu Val Val Asn Leu Ser Gly Arg
370                 375                 380 ggc gat aaa gat atg gac atc gta cgt cgt cgt ctg gct ctc gag cac       1200
Gly Asp Lys Asp Met Asp Ile Val Arg Arg Arg Leu Ala Leu Glu His
385                 390                 395                 400 cac cac cac cac cac tga                                                1218
His His His His His
            405

<210> SEQ ID NO 24
<211> LENGTH: 405
<212> TYPE: PRT
<213> ORGANISM: Artificial Sequence
<220> FEATURE:
<223> OTHER INFORMATION: Synthetic Construct

<400> SEQUENCE: 24

Met Arg Cys Trp Leu Glu Asn Leu Ser Gly Gly Arg Lys Met Lys Phe
1               5                   10                  15

Gly Glu Phe Gly Gly Arg Phe Val Pro Glu Val Leu Ile Pro Pro Leu
            20                  25                  30

Glu Glu Leu Glu Lys Ala Tyr Asp Arg Phe Lys Asp Asp Glu Glu Phe
        35                  40                  45

Lys Ala Arg Leu Glu Tyr Tyr Leu Lys Ser Tyr Ala Gly Arg Pro Thr
    50                  55                  60

Pro Leu Tyr Phe Ala Glu Asn Leu Ser Arg Glu Leu Gly Val Lys Ile
65                  70                  75                  80

Tyr Leu Lys Arg Glu Asp Leu Leu His Gly Ala His Lys Ile Asn
                85                  90                  95

Asn Thr Ile Gly Gln Ala Leu Leu Ala Lys Phe Met Gly Lys Lys Arg
            100                 105                 110

Val Ile Ala Glu Thr Gly Ala Gly Gln His Gly Val Ala Thr Ala Met
        115                 120                 125

Ala Ala Ala Leu Leu Gly Leu Glu Ala Glu Ile Tyr Met Gly Ala Glu
    130                 135                 140

Asp Tyr Glu Arg Gln Lys Met Asn Val Phe Arg Thr Glu Leu Leu Gly
145                 150                 155                 160

Ala Lys Val Thr Ala Val Glu Ser Gly Ser Arg Thr Leu Lys Asp Ala
```

```
                    165                 170                 175
Ile Asp Glu Ala Leu Arg Asp Trp Val Glu Ser Phe Glu His Thr His
                180                 185                 190

Tyr Leu Ile Gly Ser Val Val Gly Pro His Pro Phe Pro Thr Ile Val
            195                 200                 205

Arg Asp Phe Gln Ala Val Ile Gly Lys Glu Ala Arg Gln Ile Ile
        210                 215                 220

Glu Ala Glu Gly Gly Met Pro Asp Ala Ile Ile Ala Cys Val Gly Gly
225                 230                 235                 240

Gly Ser Asn Ala Met Gly Ile Phe His Pro Phe Leu Asn Asp Asp Val
                245                 250                 255

Arg Leu Ile Gly Val Glu Ala Gly Gly Glu Gly Ile Glu Ser Gly Arg
            260                 265                 270

His Ser Ala Ser Leu Thr Ala Gly Ser Lys Gly Val Leu His Gly Met
        275                 280                 285

Leu Ser Tyr Phe Leu Gln Asp Glu Glu Gly Met Met Leu Asp Thr His
    290                 295                 300

Ser Val Ser Ala Gly Leu Asp Tyr Pro Gly Val Gly Pro Glu His Ala
305                 310                 315                 320

Tyr Leu Lys Glu Thr Gly Arg Cys Glu Tyr Val Thr Val Asn Asp Glu
                325                 330                 335

Glu Ala Leu Arg Ala Phe Lys Thr Leu Ser Lys Leu Glu Gly Ile Ile
            340                 345                 350

Pro Ala Leu Glu Ser Ala His Ala Ile Ala Tyr Ala Met Lys Met Ala
        355                 360                 365

Glu Glu Met Gln Arg Asp Asp Val Leu Val Val Asn Leu Ser Gly Arg
    370                 375                 380

Gly Asp Lys Asp Met Asp Ile Val Arg Arg Leu Ala Leu Glu His
385                 390                 395                 400

His His His His His
            405

<210> SEQ ID NO 25
<211> LENGTH: 1194
<212> TYPE: DNA
<213> ORGANISM: Artificial Sequence
<220> FEATURE:
<223> OTHER INFORMATION: TmTrpBT292S
<220> FEATURE:
<221> NAME/KEY: CDS
<222> LOCATION: (1)..(1194)

<400> SEQUENCE: 25 atg aaa ggc tac ttc ggt ccg tac ggt ggc cag tac gtg cca gaa atc       48
Met Lys Gly Tyr Phe Gly Pro Tyr Gly Gly Gln Tyr Val Pro Glu Ile
1               5                   10                  15 ctg atg cca gct ctg gaa gaa ctg gaa gct gcg tac gaa gaa atc atg       96
Leu Met Pro Ala Leu Glu Glu Leu Glu Ala Ala Tyr Glu Glu Ile Met
                20                  25                  30 aaa gat gag tct ttc tgg aaa gaa ttc aat gac ctg ctg cgc gat tat      144
Lys Asp Glu Ser Phe Trp Lys Glu Phe Asn Asp Leu Leu Arg Asp Tyr
            35                  40                  45 gcg ggt cgt ccg act ccg ctg tac ttc gca cgt cgt ctg tcc gaa aaa      192
Ala Gly Arg Pro Thr Pro Leu Tyr Phe Ala Arg Arg Leu Ser Glu Lys
        50                  55                  60 tac ggt gct cgc atc tat ctg aaa cgt gaa gac ctg ctg cat act ggt      240
Tyr Gly Ala Arg Ile Tyr Leu Lys Arg Glu Asp Leu Leu His Thr Gly
65                  70                  75                  80
```

-continued

| | |
|---|---|
| gcg cat aaa atc aat aac gct atc ggc cag gtt ctg ctg gca aaa aaa<br>Ala His Lys Ile Asn Asn Ala Ile Gly Gln Val Leu Leu Ala Lys Lys<br>                     85                              90                       95 | 288 |
| atg ggc aaa acc cgt atc att gct gaa acg ggt gct ggt cag cac ggc<br>Met Gly Lys Thr Arg Ile Ile Ala Glu Thr Gly Ala Gly Gln His Gly<br>                100                       105                      110 | 336 |
| gta gca act gct acc gca gca gcg ctg ttc ggt atg gaa tgt gta atc<br>Val Ala Thr Ala Thr Ala Ala Ala Leu Phe Gly Met Glu Cys Val Ile<br>            115                       120                      125 | 384 |
| tat atg ggc gaa gaa gac acg atc cgc cag aaa ccg aac gtt gaa cgt<br>Tyr Met Gly Glu Glu Asp Thr Ile Arg Gln Lys Pro Asn Val Glu Arg<br>130                       135                      140 | 432 |
| atg aaa ctg ctg ggt gct aaa gtt gta ccg gta aaa tcc ggt agc cgt<br>Met Lys Leu Leu Gly Ala Lys Val Val Pro Val Lys Ser Gly Ser Arg<br>145                     150                       155                    160 | 480 |
| acc ctg aaa gac gca att aac gaa gct ctg cgt gac tgg att acc aac<br>Thr Leu Lys Asp Ala Ile Asn Glu Ala Leu Arg Asp Trp Ile Thr Asn<br>                165                       170                    175 | 528 |
| ctg cag acc acc tat tac gtg atc ggc tct gtg gtt ggt ccg cat cca<br>Leu Gln Thr Thr Tyr Tyr Val Ile Gly Ser Val Val Gly Pro His Pro<br>                      180                       185                    190 | 576 |
| tat ccg att atc gta cgt aac ttc caa aag gtt atc ggc gaa gag acc<br>Tyr Pro Ile Ile Val Arg Asn Phe Gln Lys Val Ile Gly Glu Glu Thr<br>            195                       200                    205 | 624 |
| aaa aaa cag att ctg gaa aaa gaa ggc cgt ctg ccg gac tac atc gtt<br>Lys Lys Gln Ile Leu Glu Lys Glu Gly Arg Leu Pro Asp Tyr Ile Val<br>210                     215                      220 | 672 |
| gcg tgc gtg ggt ggt ggt tct aac gct gcc ggt atc ttc tat ccg ttt<br>Ala Cys Val Gly Gly Gly Ser Asn Ala Ala Gly Ile Phe Tyr Pro Phe<br>225                   230                       235                    240 | 720 |
| atc gat tct ggt gtg aag ctg atc ggc gta gaa gcc ggt ggc gaa ggt<br>Ile Asp Ser Gly Val Lys Leu Ile Gly Val Glu Ala Gly Gly Glu Gly<br>                      245                       250                    255 | 768 |
| ctg gaa acc ggt aaa cat gcg gct tct ctg ctg aaa ggt aaa atc ggc<br>Leu Glu Thr Gly Lys His Ala Ala Ser Leu Leu Lys Gly Lys Ile Gly<br>            260                       265                    270 | 816 |
| tac tta cac ggt tct aag acg ttc gtt ctg cag gat gac tgg ggt caa<br>Tyr Leu His Gly Ser Lys Thr Phe Val Leu Gln Asp Asp Trp Gly Gln<br>                275                       280                    285 | 864 |
| gtt cag gtg agc cac tcc gtc tcc gct ggc ctg gac tac tcc ggt gtc<br>Val Gln Val Ser His Ser Val Ser Ala Gly Leu Asp Tyr Ser Gly Val<br>            290                       295                    300 | 912 |
| ggt ccg gaa cac gcc tat tgg cgt gag acc ggt aaa gtg ctg tac gat<br>Gly Pro Glu His Ala Tyr Trp Arg Glu Thr Gly Lys Val Leu Tyr Asp<br>305                     310                      315                    320 | 960 |
| gct gtg acc gat gaa gaa gct ctg gac gca ttc atc gaa ctg tct cgc<br>Ala Val Thr Asp Glu Glu Ala Leu Asp Ala Phe Ile Glu Leu Ser Arg<br>                      325                       330                    335 | 1008 |
| ctg gaa ggc atc atc cca gcc ctg gag tct tct cac gca ctg gct tat<br>Leu Glu Gly Ile Ile Pro Ala Leu Glu Ser Ser His Ala Leu Ala Tyr<br>                      340                       345                    350 | 1056 |
| ctg aag aag atc aac atc aag ggt aaa gtt gtg gtg gtt aat ctg tct<br>Leu Lys Lys Ile Asn Ile Lys Gly Lys Val Val Val Val Asn Leu Ser<br>                         355                       360                    365 | 1104 |
| ggt cgt ggt gac aag gat ctg gaa tct gta ctg aac cac ccg tat gtt<br>Gly Arg Gly Asp Lys Asp Leu Glu Ser Val Leu Asn His Pro Tyr Val<br>370                     375                      380 | 1152 |
| cgc gaa cgc atc cgc ctc gag cac cac cac cac cac cac tga<br>Arg Glu Arg Ile Arg Leu Glu His His His His His His | 1194 |

```
385                 390                 395
```

<210> SEQ ID NO 26
<211> LENGTH: 397
<212> TYPE: PRT
<213> ORGANISM: Artificial Sequence
<220> FEATURE:
<223> OTHER INFORMATION: Synthetic Construct

<400> SEQUENCE: 26

```
Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Val Asn Leu Ser
```

```
                    355                 360                 365
Gly Arg Gly Asp Lys Asp Leu Glu Ser Val Leu Asn His Pro Tyr Val
            370                 375                 380

Arg Glu Arg Ile Arg Leu Glu His His His His His His
385                 390                 395

<210> SEQ ID NO 27
<211> LENGTH: 1194
<212> TYPE: DNA
<213> ORGANISM: Artificial Sequence
<220> FEATURE:
<223> OTHER INFORMATION: TmTrpBP19G
<220> FEATURE:
<221> NAME/KEY: CDS
<222> LOCATION: (1)..(1194)

<400> SEQUENCE: 27 atg aaa ggc tac ttc ggt ccg tac ggt ggc cag tac gtg cca gaa atc     48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg    96
Leu Met Gly Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat   144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa   192
Ala Gly Arg Pro Thr Pro Leu Tyr Phe Ala Arg Arg Leu Ser Glu Lys
    50                  55                  60 tac ggt gct cgc atc tat ctg aaa cgt gaa gac ctg ctg cat act ggt   240
Tyr Gly Ala Arg Ile Tyr Leu Lys Arg Glu Asp Leu Leu His Thr Gly
65                  70                  75                  80 gcg cat aaa atc aat aac gct atc ggc cag gtt ctg ctg gca aaa aaa   288
Ala His Lys Ile Asn Asn Ala Ile Gly Gln Val Leu Leu Ala Lys Lys
                85                  90                  95 atg ggc aaa acc cgt atc att gct gaa acg ggt gct ggt cag cac ggc   336
Met Gly Lys Thr Arg Ile Ile Ala Glu Thr Gly Ala Gly Gln His Gly
            100                 105                 110 gta gca act gct acc gca gca gcg ctg ttc ggt atg gaa tgt gta atc   384
Val Ala Thr Ala Thr Ala Ala Ala Leu Phe Gly Met Glu Cys Val Ile
        115                 120                 125 tat atg ggc gaa gaa gac acg atc cgc cag aaa ccg aac gtt gaa cgt   432
Tyr Met Gly Glu Glu Asp Thr Ile Arg Gln Lys Pro Asn Val Glu Arg
    130                 135                 140 atg aaa ctg ctg ggt gct aaa gtt gta ccg gta aaa tcc ggt agc cgt   480
Met Lys Leu Leu Gly Ala Lys Val Val Pro Val Lys Ser Gly Ser Arg
145                 150                 155                 160 acc ctg aaa gac gca att aac gaa gct ctg cgt gac tgg att acc aac   528
Thr Leu Lys Asp Ala Ile Asn Glu Ala Leu Arg Asp Trp Ile Thr Asn
                165                 170                 175 ctg cag acc acc tat tac gtg atc ggc tct gtg gtt ggt ccg cat cca   576
Leu Gln Thr Thr Tyr Tyr Val Ile Gly Ser Val Val Gly Pro His Pro
            180                 185                 190 tat ccg att atc gta cgt aac ttc caa aag gtt atc ggc gaa gag acc   624
Tyr Pro Ile Ile Val Arg Asn Phe Gln Lys Val Ile Gly Glu Glu Thr
        195                 200                 205 aaa aaa cag att ctg gaa aaa gaa ggc cgt ctg ccg gac tac atc gtt   672
Lys Lys Gln Ile Leu Glu Lys Glu Gly Arg Leu Pro Asp Tyr Ile Val
    210                 215                 220 gcg tgc gtg ggt ggt ggt tct aac gct gcc ggt atc ttc tat ccg ttt   720
Ala Cys Val Gly Gly Gly Ser Asn Ala Ala Gly Ile Phe Tyr Pro Phe
```

```
                225                 230                 235                 240
atc gat tct ggt gtg aag ctg atc ggc gta gaa gcc ggt ggc gaa ggt      768
Ile Asp Ser Gly Val Lys Leu Ile Gly Val Glu Ala Gly Gly Glu Gly
                    245                 250                 255 ctg gaa acc ggt aaa cat gcg gct tct ctg ctg aaa ggt aaa atc ggc      816
Leu Glu Thr Gly Lys His Ala Ala Ser Leu Leu Lys Gly Lys Ile Gly
                260                 265                 270 tac tta cac ggt tct aag acg ttc gtt ctg cag gat gac tgg ggt caa      864
Tyr Leu His Gly Ser Lys Thr Phe Val Leu Gln Asp Asp Trp Gly Gln
            275                 280                 285 gtt cag gtg acg cac tcc gtc tcc gct ggc ctg gac tac tcc ggt gtc      912
Val Gln Val Thr His Ser Val Ser Ala Gly Leu Asp Tyr Ser Gly Val
        290                 295                 300 ggt ccg gaa cac gcc tat tgg cgt gag acc ggt aaa gtg ctg tac gat      960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc     1008
Ala Val Thr Asp Glu Glu Ala Leu Asp Ala Phe Ile Glu Leu Ser Arg
                    325                 330                 335 ctg gaa ggc atc atc cca gcc ctg gag tct tct cac gca ctg gct tat     1056
Leu Glu Gly Ile Ile Pro Ala Leu Glu Ser Ser His Ala Leu Ala Tyr
                340                 345                 350 ctg aag aag atc aac atc aag ggt aaa gtt gtg gtg gtt aat ctg tct     1104
Leu Lys Lys Ile Asn Ile Lys Gly Lys Val Val Val Val Asn Leu Ser
            355                 360                 365 ggt cgt ggt gac aag gat ctg gaa tct gta ctg aac cac ccg tat gtt     1152
Gly Arg Gly Asp Lys Asp Leu Glu Ser Val Leu Asn His Pro Tyr Val
        370                 375                 380 cgc gaa cgc atc cgc ctc gag cac cac cac cac cac cac tga             1194
Arg Glu Arg Ile Arg Leu Glu His His His His His His
385                 390                 395

<210> SEQ ID NO 28
<211> LENGTH: 397
<212> TYPE: PRT
<213> ORGANISM: Artificial Sequence
<220> FEATURE:
<223> OTHER INFORMATION: Synthetic Construct

<400> SEQUENCE: 28

Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
    130                 135                 140
```

```
Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
370                 375                 380

Arg Glu Arg Ile Arg Leu Glu His His His His His
385                 390                 395

<210> SEQ ID NO 29
<211> LENGTH: 1194
<212> TYPE: DNA
<213> ORGANISM: Artificial Sequence
<220> FEATURE:
<223> OTHER INFORMATION: TmTrpBP19GT292S
<220> FEATURE:
<221> NAME/KEY: CDS
<222> LOCATION: (1)..(1194)

<400> SEQUENCE: 29 atg aaa ggc tac ttc ggt ccg tac ggt ggc cag tac gtg cca gaa atc    48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg    96
Leu Met Gly Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat   144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa   192
Ala Gly Arg Pro Thr Pro Leu Tyr Phe Ala Arg Arg Leu Ser Glu Lys
    50                  55                  60 tac ggt gct cgc atc tat ctg aaa cgt gaa gac ctg ctg cat act ggt   240
Tyr Gly Ala Arg Ile Tyr Leu Lys Arg Glu Asp Leu Leu His Thr Gly
```

```
                65                  70                  75                  80
gcg cat aaa atc aat aac gct atc ggc cag gtt ctg ctg gca aaa aaa       288
Ala His Lys Ile Asn Asn Ala Ile Gly Gln Val Leu Leu Ala Lys Lys
                    85                  90                  95 atg ggc aaa acc cgt atc att gct gaa acg ggt gct ggt cag cac ggc       336
Met Gly Lys Thr Arg Ile Ile Ala Glu Thr Gly Ala Gly Gln His Gly
                100                 105                 110 gta gca act gct acc gca gca gcg ctg ttc ggt atg gaa tgt gta atc       384
Val Ala Thr Ala Thr Ala Ala Ala Leu Phe Gly Met Glu Cys Val Ile
                    115                 120                 125 tat atg ggc gaa gaa gac acg atc cgc cag aaa ccg aac gtt gaa cgt       432
Tyr Met Gly Glu Glu Asp Thr Ile Arg Gln Lys Pro Asn Val Glu Arg
        130                 135                 140 atg aaa ctg ctg ggt gct aaa gtt gta ccg gta aaa tcc ggt agc cgt       480
Met Lys Leu Leu Gly Ala Lys Val Val Pro Val Lys Ser Gly Ser Arg
145                 150                 155                 160 acc ctg aaa gac gca att aac gaa gct ctg cgt gac tgg att acc aac       528
Thr Leu Lys Asp Ala Ile Asn Glu Ala Leu Arg Asp Trp Ile Thr Asn
                    165                 170                 175 ctg cag acc acc tat tac gtg atc ggc tct gtg gtt ggt ccg cat cca       576
Leu Gln Thr Thr Tyr Tyr Val Ile Gly Ser Val Val Gly Pro His Pro
                    180                 185                 190 tat ccg att atc gta cgt aac ttc caa aag gtt atc ggc gaa gag acc       624
Tyr Pro Ile Ile Val Arg Asn Phe Gln Lys Val Ile Gly Glu Glu Thr
                195                 200                 205 aaa aaa cag att ctg gaa aaa gaa ggc cgt ctg ccg gac tac atc gtt       672
Lys Lys Gln Ile Leu Glu Lys Glu Gly Arg Leu Pro Asp Tyr Ile Val
        210                 215                 220 gcg tgc gtg ggt ggt ggt tct aac gct gcc ggt atc ttc tat ccg ttt       720
Ala Cys Val Gly Gly Gly Ser Asn Ala Ala Gly Ile Phe Tyr Pro Phe
225                 230                 235                 240 atc gat tct ggt gtg aag ctg atc ggc gta gaa gcc ggt ggc gaa ggt       768
Ile Asp Ser Gly Val Lys Leu Ile Gly Val Glu Ala Gly Gly Glu Gly
                    245                 250                 255 ctg gaa acc ggt aaa cat gcg gct tct ctg ctg aaa ggt aaa atc ggc       816
Leu Glu Thr Gly Lys His Ala Ala Ser Leu Leu Lys Gly Lys Ile Gly
                    260                 265                 270 tac tta cac ggt tct aag acg ttc gtt ctg cag gat gac tgg ggt caa       864
Tyr Leu His Gly Ser Lys Thr Phe Val Leu Gln Asp Asp Trp Gly Gln
                275                 280                 285 gtt cag gtg agc cac tcc gtc tcc gct ggc ctg gac tac tcc ggt gtc       912
Val Gln Val Ser His Ser Val Ser Ala Gly Leu Asp Tyr Ser Gly Val
        290                 295                 300 ggt ccg gaa cac gcc tat tgg cgt gag acc ggt aaa gtg ctg tac gat       960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc      1008
Ala Val Thr Asp Glu Glu Ala Leu Asp Ala Phe Ile Glu Leu Ser Arg
                    325                 330                 335 ctg gaa ggc atc atc cca gcc ctg gag tct tct cac gca ctg gct tat      1056
Leu Glu Gly Ile Ile Pro Ala Leu Glu Ser Ser His Ala Leu Ala Tyr
                    340                 345                 350 ctg aag aag atc aac atc aag ggt aaa gtt gtg gtg gtt aat ctg tct      1104
Leu Lys Lys Ile Asn Ile Lys Gly Lys Val Val Val Val Asn Leu Ser
                355                 360                 365 ggt cgt ggt gac aag gat ctg gaa tct gta ctg aac cac ccg tat gtt      1152
Gly Arg Gly Asp Lys Asp Leu Glu Ser Val Leu Asn His Pro Tyr Val
        370                 375                 380 cgc gaa cgc atc cgc ctc gag cac cac cac cac cac cac tga              1194
```

Arg Glu Arg Ile Arg Leu Glu His His His His His His
385                 390                 395

<210> SEQ ID NO 30
<211> LENGTH: 397
<212> TYPE: PRT
<213> ORGANISM: Artificial Sequence
<220> FEATURE:
<223> OTHER INFORMATION: Synthetic Construct

<400> SEQUENCE: 30

Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Leu Phe Gly Met Glu Cys Val Ile
            115                 120                 125

Tyr Met Gly Glu Glu Asp Thr Ile Arg Gln Lys Pro Asn Val Glu Arg
        130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

-continued

```
Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
370                 375                 380

Arg Glu Arg Ile Arg Leu Glu His His His His His His
385                 390                 395

<210> SEQ ID NO 31
<211> LENGTH: 1194
<212> TYPE: DNA
<213> ORGANISM: Artificial Sequence
<220> FEATURE:
<223> OTHER INFORMATION: TmTrpBP19GI69V
<220> FEATURE:
<221> NAME/KEY: CDS
<222> LOCATION: (1)..(1194)

<400> SEQUENCE: 31 atg aaa ggc tac ttc ggt ccg tac ggt ggc cag tac gtg cca gaa atc        48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg       96
Leu Met Gly Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat      144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa      192
Ala Gly Arg Pro Thr Pro Leu Tyr Phe Ala Arg Arg Leu Ser Glu Lys
    50                  55                  60 tac ggt gct cgc gta tat ctg aaa cgt gaa gac ctg ctg cat act ggt      240
Tyr Gly Ala Arg Val Tyr Leu Lys Arg Glu Asp Leu Leu His Thr Gly
65                  70                  75                  80 gcg cat aaa atc aat aac gct atc ggc cag gtt ctg ctg gca aaa aaa      288
Ala His Lys Ile Asn Asn Ala Ile Gly Gln Val Leu Leu Ala Lys Lys
                85                  90                  95 atg ggc aaa acc cgt atc att gct gaa acg ggt gct ggt cag cac ggc      336
Met Gly Lys Thr Arg Ile Ile Ala Glu Thr Gly Ala Gly Gln His Gly
            100                 105                 110 gta gca act gct acc gca gca gcg ctg ttc ggt atg gaa tgt gta atc      384
Val Ala Thr Ala Thr Ala Ala Ala Leu Phe Gly Met Glu Cys Val Ile
        115                 120                 125 tat atg ggc gaa gaa gac acg atc cgc cag aaa ccg aac gtt gaa cgt      432
Tyr Met Gly Glu Glu Asp Thr Ile Arg Gln Lys Pro Asn Val Glu Arg
    130                 135                 140 atg aaa ctg ctg ggt gct aaa gtt gta ccg gta aaa tcc ggt agc cgt      480
Met Lys Leu Leu Gly Ala Lys Val Val Pro Val Lys Ser Gly Ser Arg
145                 150                 155                 160 acc ctg aaa gac gca att aac gaa gct ctg cgt gac tgg att acc aac      528
Thr Leu Lys Asp Ala Ile Asn Glu Ala Leu Arg Asp Trp Ile Thr Asn
                165                 170                 175 ctg cag acc acc tat tac gtg atc ggc tct gtg gtt ggt ccg cat cca      576
Leu Gln Thr Thr Tyr Tyr Val Ile Gly Ser Val Val Gly Pro His Pro
            180                 185                 190 tat ccg att atc gta cgt aac ttc caa aag gtt atc ggc gaa gag acc      624
Tyr Pro Ile Ile Val Arg Asn Phe Gln Lys Val Ile Gly Glu Glu Thr
        195                 200                 205 aaa aaa cag att ctg gaa aaa gaa ggt cgt ctg ccg gac tac atc gtt      672
Lys Lys Gln Ile Leu Glu Lys Glu Gly Arg Leu Pro Asp Tyr Ile Val
    210                 215                 220 gcg tgc gtg ggt ggt ggt tct aac gct gcc ggt atc ttc tat ccg ttt      720
Ala Cys Val Gly Gly Gly Ser Asn Ala Ala Gly Ile Phe Tyr Pro Phe
```

```
Ala Cys Val Gly Gly Gly Ser Asn Ala Ala Gly Ile Phe Tyr Pro Phe
225                 230                 235                 240 atc gat tct ggt gtg aag ctg atc ggc gta gaa gcc ggt ggc gaa ggt      768
Ile Asp Ser Gly Val Lys Leu Ile Gly Val Glu Ala Gly Gly Glu Gly
                    245                 250                 255 ctg gaa acc ggt aaa cat gcg gct tct ctg ctg aaa ggt aaa atc ggc      816
Leu Glu Thr Gly Lys His Ala Ala Ser Leu Leu Lys Gly Lys Ile Gly
                260                 265                 270 tac tta cac ggt tct aag acg ttc gtt ctg cag gat gac tgg ggt caa      864
Tyr Leu His Gly Ser Lys Thr Phe Val Leu Gln Asp Asp Trp Gly Gln
            275                 280                 285 gtt cag gtg acg cac tcc gtc tcc gct ggc ctg gac tac tcc ggt gtc      912
Val Gln Val Thr His Ser Val Ser Ala Gly Leu Asp Tyr Ser Gly Val
        290                 295                 300 ggt ccg gaa cac gcc tat tgg cgt gag acc ggt aaa gtg ctg tac gat      960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc     1008
Ala Val Thr Asp Glu Glu Ala Leu Asp Ala Phe Ile Glu Leu Ser Arg
                325                 330                 335 ctg gaa ggc atc atc cca gcc ctg gag tct tct cac gca ctg gct tat     1056
Leu Glu Gly Ile Ile Pro Ala Leu Glu Ser Ser His Ala Leu Ala Tyr
                340                 345                 350 ctg aag aag atc aac atc aag ggt aaa gtt gtg gtg gtt aat ctg tct     1104
Leu Lys Lys Ile Asn Ile Lys Gly Lys Val Val Val Val Asn Leu Ser
            355                 360                 365 ggt cgt ggt gac aag gat ctg gaa tct gta ctg aac cac ccg tat gtt     1152
Gly Arg Gly Asp Lys Asp Leu Glu Ser Val Leu Asn His Pro Tyr Val
        370                 375                 380 cgc gaa cgc atc cgc ctc gag cac cac cac cac cac cac tga              1194
Arg Glu Arg Ile Arg Leu Glu His His His His His His
385                 390                 395

<210> SEQ ID NO 32
<211> LENGTH: 397
<212> TYPE: PRT
<213> ORGANISM: Artificial Sequence
<220> FEATURE:
<223> OTHER INFORMATION: Synthetic Construct

<400> SEQUENCE: 32

Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
                20                  25                  30

Lys Asp Glu Ser Phe Trp Lys Glu Phe Asn Asp Leu Leu Arg Asp Tyr
            35                  40                  45

Ala Gly Arg Pro Thr Pro Leu Tyr Phe Ala Arg Arg Leu Ser Glu Lys
        50                  55                  60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
130                 135                 140
```

```
Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
            165                 170                 175

Leu Gln Thr Thr Tyr Tyr Val Ile Gly Ser Val Val Gly Pro His Pro
        180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
210                 215                 220

Ala Cys Val Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
            245                 250                 255

Leu Glu Thr Gly Lys His Ala Ala Ser Leu Leu Lys Gly Lys Ile Gly
        260                 265                 270

Tyr Leu His Gly Ser Lys Thr Phe Val Leu Gln Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
            325                 330                 335

Leu Glu Gly Ile Ile Pro Ala Leu Glu Ser Ser His Ala Leu Ala Tyr
        340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
370                 375                 380

Arg Glu Arg Ile Arg Leu Glu His His His His His
385                 390                 395
```

<210> SEQ ID NO 33
<211> LENGTH: 1194
<212> TYPE: DNA
<213> ORGANISM: Artificial Sequence
<220> FEATURE:
<223> OTHER INFORMATION: TmTrpBP19GI69VT292S
<220> FEATURE:
<221> NAME/KEY: CDS
<222> LOCATION: (1)..(1194)

<400> SEQUENCE: 33

```
atg aaa ggc tac ttc ggt ccg tac ggt ggc cag tac gtg cca gaa atc    48
Met Lys Gly Tyr Phe Gly Pro Tyr Gly Gly Gln Tyr Val Pro Glu Ile
1               5                   10                  15 ctg atg gga gct ctg gaa gaa ctg gaa gct gcg tac gaa gaa atc atg    96
Leu Met Gly Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat   144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa   192
Ala Gly Arg Pro Thr Pro Leu Tyr Phe Ala Arg Arg Leu Ser Glu Lys
    50                  55                  60 tac ggt gct cgc gta tat ctg aaa cgt gaa gac ctg ctg cat act ggt   240
```

|  |  |  |  |  |  |  |  |  |  |  |  |  |  |  |
|---|---|---|---|---|---|---|---|---|---|---|---|---|---|---|
| Tyr | Gly | Ala | Arg | Val | Tyr | Leu | Lys | Arg | Glu | Asp | Leu | Leu | His | Thr | Gly |
| 65 |  |  |  | 70 |  |  |  | 75 |  |  |  | 80 |

| gcg | cat | aaa | atc | aat | aac | gct | atc | ggc | cag | gtt | ctg | ctg | gca | aaa | aaa | 288 |
|---|---|---|---|---|---|---|---|---|---|---|---|---|---|---|---|---|
| Ala | His | Lys | Ile | Asn | Asn | Ala | Ile | Gly | Gln | Val | Leu | Leu | Ala | Lys | Lys |
|  |  |  |  | 85 |  |  |  |  | 90 |  |  |  |  | 95 |

| atg | ggc | aaa | acc | cgt | atc | att | gct | gaa | acg | ggt | gct | ggt | cag | cac | ggc | 336 |
| Met | Gly | Lys | Thr | Arg | Ile | Ile | Ala | Glu | Thr | Gly | Ala | Gly | Gln | His | Gly |
|  |  |  | 100 |  |  |  |  | 105 |  |  |  |  | 110 |

| gta | gca | act | gct | acc | gca | gca | gcg | ctg | ttc | ggt | atg | gaa | tgt | gta | atc | 384 |
| Val | Ala | Thr | Ala | Thr | Ala | Ala | Ala | Leu | Phe | Gly | Met | Glu | Cys | Val | Ile |
|  |  |  | 115 |  |  |  |  | 120 |  |  |  |  | 125 |

| tat | atg | ggc | gaa | gaa | gac | acg | atc | cgc | cag | aaa | ccg | aac | gtt | gaa | cgt | 432 |
| Tyr | Met | Gly | Glu | Glu | Asp | Thr | Ile | Arg | Gln | Lys | Pro | Asn | Val | Glu | Arg |
|  | 130 |  |  |  |  | 135 |  |  |  |  | 140 |

| atg | aaa | ctg | ctg | ggt | gct | aaa | gtt | gta | ccg | gta | aaa | tcc | ggt | agc | cgt | 480 |
| Met | Lys | Leu | Leu | Gly | Ala | Lys | Val | Val | Pro | Val | Lys | Ser | Gly | Ser | Arg |
| 145 |  |  |  |  | 150 |  |  |  |  | 155 |  |  |  |  | 160 |

| acc | ctg | aaa | gac | gca | att | aac | gaa | gct | ctg | cgt | gac | tgg | att | acc | aac | 528 |
| Thr | Leu | Lys | Asp | Ala | Ile | Asn | Glu | Ala | Leu | Arg | Asp | Trp | Ile | Thr | Asn |
|  |  |  |  | 165 |  |  |  |  | 170 |  |  |  |  | 175 |

| ctg | cag | acc | acc | tat | tac | gtg | atc | ggc | tct | gtg | gtt | ggt | ccg | cat | cca | 576 |
| Leu | Gln | Thr | Thr | Tyr | Tyr | Val | Ile | Gly | Ser | Val | Val | Gly | Pro | His | Pro |
|  |  |  | 180 |  |  |  |  | 185 |  |  |  |  | 190 |

| tat | ccg | att | atc | gta | cgt | aac | ttc | caa | aag | gtt | atc | ggc | gaa | gag | acc | 624 |
| Tyr | Pro | Ile | Ile | Val | Arg | Asn | Phe | Gln | Lys | Val | Ile | Gly | Glu | Glu | Thr |
|  |  | 195 |  |  |  |  | 200 |  |  |  |  | 205 |

| aaa | aaa | cag | att | ctg | gaa | aaa | gaa | ggc | cgt | ctg | ccg | gac | tac | atc | gtt | 672 |
| Lys | Lys | Gln | Ile | Leu | Glu | Lys | Glu | Gly | Arg | Leu | Pro | Asp | Tyr | Ile | Val |
| 210 |  |  |  |  | 215 |  |  |  |  | 220 |

| gcg | tgc | gtg | ggt | ggt | ggt | tct | aac | gct | gcc | ggt | atc | ttc | tat | ccg | ttt | 720 |
| Ala | Cys | Val | Gly | Gly | Gly | Ser | Asn | Ala | Ala | Gly | Ile | Phe | Tyr | Pro | Phe |
| 225 |  |  |  |  | 230 |  |  |  |  | 235 |  |  |  |  | 240 |

| atc | gat | tct | ggt | gtg | aag | ctg | atc | ggc | gta | gaa | gcc | ggt | ggc | gaa | ggt | 768 |
| Ile | Asp | Ser | Gly | Val | Lys | Leu | Ile | Gly | Val | Glu | Ala | Gly | Gly | Glu | Gly |
|  |  |  |  | 245 |  |  |  |  | 250 |  |  |  |  | 255 |

| ctg | gaa | acc | ggt | aaa | cat | gcg | gct | tct | ctg | ctg | aaa | ggt | aaa | atc | ggc | 816 |
| Leu | Glu | Thr | Gly | Lys | His | Ala | Ala | Ser | Leu | Leu | Lys | Gly | Lys | Ile | Gly |
|  |  |  | 260 |  |  |  |  | 265 |  |  |  |  | 270 |

| tac | tta | cac | ggt | tct | aag | acg | ttc | gtt | ctg | cag | gat | gac | tgg | ggt | caa | 864 |
| Tyr | Leu | His | Gly | Ser | Lys | Thr | Phe | Val | Leu | Gln | Asp | Asp | Trp | Gly | Gln |
|  | 275 |  |  |  |  | 280 |  |  |  |  | 285 |

| gtt | cag | gtg | agc | cac | tcc | gtc | tcc | gct | ggc | ctg | gac | tac | tcc | ggt | gtc | 912 |
| Val | Gln | Val | Ser | His | Ser | Val | Ser | Ala | Gly | Leu | Asp | Tyr | Ser | Gly | Val |
|  | 290 |  |  |  |  | 295 |  |  |  |  | 300 |

| ggt | ccg | gaa | cac | gcc | tat | tgg | cgt | gag | acc | ggt | aaa | gtg | ctg | tac | gat | 960 |
| Gly | Pro | Glu | His | Ala | Tyr | Trp | Arg | Glu | Thr | Gly | Lys | Val | Leu | Tyr | Asp |
| 305 |  |  |  |  | 310 |  |  |  |  | 315 |  |  |  |  | 320 |

| gct | gtg | acc | gat | gaa | gaa | gct | ctg | gac | gca | ttc | atc | gaa | ctg | tct | cgc | 1008 |
| Ala | Val | Thr | Asp | Glu | Glu | Ala | Leu | Asp | Ala | Phe | Ile | Glu | Leu | Ser | Arg |
|  |  |  | 325 |  |  |  |  | 330 |  |  |  |  | 335 |

| ctg | gaa | ggc | atc | atc | cca | gcc | ctg | gag | tct | tct | cac | gca | ctg | gct | tat | 1056 |
| Leu | Glu | Gly | Ile | Ile | Pro | Ala | Leu | Glu | Ser | Ser | His | Ala | Leu | Ala | Tyr |
|  |  |  | 340 |  |  |  |  | 345 |  |  |  |  | 350 |

| ctg | aag | aag | atc | aac | atc | aag | ggt | aaa | gtt | gtg | gtg | gtt | aat | ctg | tct | 1104 |
| Leu | Lys | Lys | Ile | Asn | Ile | Lys | Gly | Lys | Val | Val | Val | Val | Asn | Leu | Ser |
|  |  | 355 |  |  |  |  | 360 |  |  |  |  | 365 |

| ggt | cgt | ggt | gac | aag | gat | ctg | gaa | tct | gta | ctg | aac | cac | ccg | tat | gtt | 1152 |
| Gly | Arg | Gly | Asp | Lys | Asp | Leu | Glu | Ser | Val | Leu | Asn | His | Pro | Tyr | Val |
| 370 |  |  |  |  | 375 |  |  |  |  | 380 |

```
cgc gaa cgc atc cgc ctc gag cac cac cac cac cac cac tga              1194
Arg Glu Arg Ile Arg Leu Glu His His His His His His
385                 390                 395
```

<210> SEQ ID NO 34
<211> LENGTH: 397
<212> TYPE: PRT
<213> ORGANISM: Artificial Sequence
<220> FEATURE:
<223> OTHER INFORMATION: Synthetic Construct

<400> SEQUENCE: 34

```
Met Lys Gly Tyr Phe Gly Pro Tyr Gly Gly Gln Tyr Val Pro Glu Ile
1               5                   10                  15

Leu Met Gly Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350
```

```
Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
370                 375                 380

Arg Glu Arg Ile Arg Leu Glu His His His His His His
385                 390                 395

<210> SEQ ID NO 35
<211> LENGTH: 1194
<212> TYPE: DNA
<213> ORGANISM: Artificial Sequence
<220> FEATURE:
<223> OTHER INFORMATION: TmTrpBM145TN167D
<220> FEATURE:
<221> NAME/KEY: CDS
<222> LOCATION: (1)..(1194)

<400> SEQUENCE: 35 atg aaa ggc tac ttc ggt ccg tac ggt ggc cag tac gtg ccg gaa atc     48
Met Lys Gly Tyr Phe Gly Pro Tyr Gly Gly Gln Tyr Val Pro Glu Ile
1               5                   10                  15 ctg atg cca gct ctg gaa gaa ctg gaa gct gcg tac gaa gaa atc atg    96
Leu Met Pro Ala Leu Glu Glu Leu Glu Ala Ala Tyr Glu Glu Ile Met
            20                  25                  30 aaa gat gag tct ttc tgg aaa gaa ttc aat gac ctg ctg cgc gat tat   144
Lys Asp Glu Ser Phe Trp Lys Glu Phe Asn Asp Leu Leu Arg Asp Tyr
        35                  40                  45 gcg ggt cgt ccg act ccg ctg tac ttc gca cgt cgt ctg tcc gaa aaa   192
Ala Gly Arg Pro Thr Pro Leu Tyr Phe Ala Arg Arg Leu Ser Glu Lys
    50                  55                  60 tac ggt gct cgc atc tat ctg aaa cgt gaa gac ctg ctg cat act ggt   240
Tyr Gly Ala Arg Ile Tyr Leu Lys Arg Glu Asp Leu Leu His Thr Gly
65                  70                  75                  80 gcg cat aaa atc aat aac gct atc ggc cag gtt ctg ctg gca aaa aaa   288
Ala His Lys Ile Asn Asn Ala Ile Gly Gln Val Leu Leu Ala Lys Lys
                85                  90                  95 atg ggc aaa acc cgt atc att gct gaa acg ggt gct ggt cag cac ggc   336
Met Gly Lys Thr Arg Ile Ile Ala Glu Thr Gly Ala Gly Gln His Gly
            100                 105                 110 gta gca act gct acc gca gca gcg ctg ttc ggt atg gaa tgt gta atc   384
Val Ala Thr Ala Thr Ala Ala Ala Leu Phe Gly Met Glu Cys Val Ile
        115                 120                 125 tat atg ggc gaa gaa gac acg atc cgc cag aaa ccg aac gtt gaa cgt   432
Tyr Met Gly Glu Glu Asp Thr Ile Arg Gln Lys Pro Asn Val Glu Arg
    130                 135                 140 acg aaa ctg ctg ggt gct aaa gtt gta ccg gta aaa tcc ggt agc cgt   480
Thr Lys Leu Leu Gly Ala Lys Val Val Pro Val Lys Ser Gly Ser Arg
145                 150                 155                 160 acc ctg aaa gac gca att gac gaa gct ctg cgt gac tgg att acc aac   528
Thr Leu Lys Asp Ala Ile Asp Glu Ala Leu Arg Asp Trp Ile Thr Asn
                165                 170                 175 ctg cag acc acc tat tac gtg atc ggc tct gtg gtt ggt ccg cat cca   576
Leu Gln Thr Thr Tyr Tyr Val Ile Gly Ser Val Val Gly Pro His Pro
            180                 185                 190 tat ccg att atc gta cgt aac ttc caa aag gtt atc ggc gaa gag acc   624
Tyr Pro Ile Ile Val Arg Asn Phe Gln Lys Val Ile Gly Glu Glu Thr
        195                 200                 205 aaa aaa cag att ctg gaa aaa gaa ggc cgt ctg ccg gac tac atc gtt   672
Lys Lys Gln Ile Leu Glu Lys Glu Gly Arg Leu Pro Asp Tyr Ile Val
    210                 215                 220
```

```
gcg tgc gtg ggt ggt ggt tct aac gct gcc ggt atc ttc tat ccg ttt    720
Ala Cys Val Gly Gly Gly Ser Asn Ala Ala Gly Ile Phe Tyr Pro Phe
225                 230                 235                 240 atc gat tct ggt gtg aag ctg atc ggc gta gaa gcc ggt ggc gaa ggt    768
Ile Asp Ser Gly Val Lys Leu Ile Gly Val Glu Ala Gly Gly Glu Gly
            245                 250                 255 ctg gaa acc ggt aaa cat gcg gct tct ctg ctg aaa ggt aaa atc ggc    816
Leu Glu Thr Gly Lys His Ala Ala Ser Leu Leu Lys Gly Lys Ile Gly
        260                 265                 270 tac ctg cac ggt tct aag acg ttc gtt ctg cag gat gac tgg ggt caa    864
Tyr Leu His Gly Ser Lys Thr Phe Val Leu Gln Asp Asp Trp Gly Gln
    275                 280                 285 gtt cag gtg acg cac tcc gtc tcc gct ggc ctg gac tac tcc ggt gtc    912
Val Gln Val Thr His Ser Val Ser Ala Gly Leu Asp Tyr Ser Gly Val
290                 295                 300 ggt ccg gaa cac gcc tat tgg cgt gag acc ggt aaa gtg ctg tac gat    960
Gly Pro Glu His Ala Tyr Trp Arg Glu Thr Gly Lys Val Leu Tyr Asp
305                 310                 315                 320 gct gtg acc gat gaa gaa gct ctg gac gca ttc atc gaa ctg tct cgc    1008
Ala Val Thr Asp Glu Glu Ala Leu Asp Ala Phe Ile Glu Leu Ser Arg
            325                 330                 335 ctg gaa ggc atc atc cca gcc ctg gag tct tct cac gca ctg gct tat    1056
Leu Glu Gly Ile Ile Pro Ala Leu Glu Ser Ser His Ala Leu Ala Tyr
        340                 345                 350 ctg aag aag atc aac atc aag ggt aaa gtt gtg gtg gtt aat ctg tct    1104
Leu Lys Lys Ile Asn Ile Lys Gly Lys Val Val Val Val Asn Leu Ser
    355                 360                 365 ggt cgt ggt gac aag gat ctg gaa tct gta ctg aac cac ccg tat gtt    1152
Gly Arg Gly Asp Lys Asp Leu Glu Ser Val Leu Asn His Pro Tyr Val
370                 375                 380 cgc gaa cgc atc cgc ctc gag cac cac cac cac cac cac tga            1194
Arg Glu Arg Ile Arg Leu Glu His His His His His His
385                 390                 395

<210> SEQ ID NO 36
<211> LENGTH: 397
<212> TYPE: PRT
<213> ORGANISM: Artificial Sequence
<220> FEATURE:
<223> OTHER INFORMATION: Synthetic Construct

<400> SEQUENCE: 36

Met Lys Gly Tyr Phe Gly Pro Tyr Gly Gly Gln Tyr Val Pro Glu Ile
1               5                   10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
        35                  40                  45

Ala Gly Arg Pro Thr Pro Leu Tyr Phe Ala Arg Arg Leu Ser Glu Lys
    50                  55                  60

Tyr Gly Ala Arg Ile Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
```

```
        130                 135                 140
Thr Lys Leu Leu Gly Ala Lys Val Val Pro Val Lys Ser Gly Ser Arg
145                 150                 155                 160

Thr Leu Lys Asp Ala Ile Asp Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Thr His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
            340                 345                 350

Leu Lys Lys Ile Asn Ile Lys Gly Lys Val Val Val Asn Leu Ser
        355                 360                 365

Gly Arg Gly Asp Lys Asp Leu Glu Ser Val Leu Asn His Pro Tyr Val
    370                 375                 380

Arg Glu Arg Ile Arg Leu Glu His His His His His His
385                 390                 395

<210> SEQ ID NO 37
<211> LENGTH: 1194
<212> TYPE: DNA
<213> ORGANISM: Artificial Sequence
<220> FEATURE:
<223> OTHER INFORMATION: TmTrpBI69VT292S
<220> FEATURE:
<221> NAME/KEY: CDS
<222> LOCATION: (1)..(1194)

<400> SEQUENCE: 37 atg aaa ggc tac ttc ggt ccg tac ggt ggc cag tac gtg cca gaa atc      48
Met Lys Gly Tyr Phe Gly Pro Tyr Gly Gly Gln Tyr Val Pro Glu Ile
1               5                   10                  15 ctg atg cca gct ctg gaa gaa ctg gaa gct gcg tac gaa gaa atc atg      96
Leu Met Pro Ala Leu Glu Glu Leu Glu Ala Ala Tyr Glu Glu Ile Met
                20                  25                  30 aaa gat gag tct ttc tgg aaa gaa ttc aat gac ctg ctg cgc gat tat     144
Lys Asp Glu Ser Phe Trp Lys Glu Phe Asn Asp Leu Leu Arg Asp Tyr
            35                  40                  45 gcg ggt cgt ccg act ccg ctg tac ttc gca cgt cgt ctg tcc gaa aaa     192
Ala Gly Arg Pro Thr Pro Leu Tyr Phe Ala Arg Arg Leu Ser Glu Lys
        50                  55                  60
```

-continued

| | | | | | | | | | | | | | | | | |
|---|---|---|---|---|---|---|---|---|---|---|---|---|---|---|---|---|
| tac | ggt | gct | cgc | gta | tat | ctg | aaa | cgt | gaa | gac | ctg | ctg | cat | act | ggt | 240 |
| Tyr | Gly | Ala | Arg | Val | Tyr | Leu | Lys | Arg | Glu | Asp | Leu | Leu | His | Thr | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gcg | cat | aaa | atc | aat | aac | gct | atc | ggc | cag | gtt | ctg | ctg | gca | aaa | aaa | 288 |
| Ala | His | Lys | Ile | Asn | Asn | Ala | Ile | Gly | Gln | Val | Leu | Leu | Ala | Lys | Lys | |
| | | | | 85 | | | | 90 | | | | | 95 | | | |

| | | | | | | | | | | | | | | | | |
|---|---|---|---|---|---|---|---|---|---|---|---|---|---|---|---|---|
| atg | ggc | aaa | acc | cgt | atc | att | gct | gaa | acg | ggt | gct | ggt | cag | cac | ggc | 336 |
| Met | Gly | Lys | Thr | Arg | Ile | Ile | Ala | Glu | Thr | Gly | Ala | Gly | Gln | His | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| gta | gca | act | gct | acc | gca | gca | gcg | ctg | ttc | ggt | atg | gaa | tgt | gta | atc | 384 |
| Val | Ala | Thr | Ala | Thr | Ala | Ala | Ala | Leu | Phe | Gly | Met | Glu | Cys | Val | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| tat | atg | ggc | gaa | gaa | gac | acg | atc | cgc | cag | aaa | ccg | aac | gtt | gaa | cgt | 432 |
| Tyr | Met | Gly | Glu | Glu | Asp | Thr | Ile | Arg | Gln | Lys | Pro | Asn | Val | Glu | Arg | |
| | 130 | | | | | 135 | | | | | 140 | | | | | |

| | | | | | | | | | | | | | | | | |
|---|---|---|---|---|---|---|---|---|---|---|---|---|---|---|---|---|
| atg | aaa | ctg | ctg | ggt | gct | aaa | gtt | gta | ccg | gta | aaa | tcc | ggt | agc | cgt | 480 |
| Met | Lys | Leu | Leu | Gly | Ala | Lys | Val | Val | Pro | Val | Lys | Ser | Gly | Ser | Arg | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| acc | ctg | aaa | gac | gca | att | aac | gaa | gct | ctg | cgt | gac | tgg | att | acc | aac | 528 |
| Thr | Leu | Lys | Asp | Ala | Ile | Asn | Glu | Ala | Leu | Arg | Asp | Trp | Ile | Thr | Asn | |
| | | | | 165 | | | | 170 | | | | | 175 | | | |

| | | | | | | | | | | | | | | | | |
|---|---|---|---|---|---|---|---|---|---|---|---|---|---|---|---|---|
| ctg | cag | acc | acc | tat | tac | gtg | atc | ggc | tct | gtg | gtt | ggt | ccg | cat | cca | 576 |
| Leu | Gln | Thr | Thr | Tyr | Tyr | Val | Ile | Gly | Ser | Val | Val | Gly | Pro | His | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| tat | ccg | att | atc | gta | cgt | aac | ttc | caa | aag | gtt | atc | ggc | gaa | gag | acc | 624 |
| Tyr | Pro | Ile | Ile | Val | Arg | Asn | Phe | Gln | Lys | Val | Ile | Gly | Glu | Glu | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| aaa | aaa | cag | att | ctg | gaa | aaa | gaa | ggc | cgt | ctg | ccg | gac | tac | atc | gtt | 672 |
| Lys | Lys | Gln | Ile | Leu | Glu | Lys | Glu | Gly | Arg | Leu | Pro | Asp | Tyr | Ile | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| gcg | tgc | gtg | ggt | ggt | ggt | tct | aac | gct | gcc | ggt | atc | ttc | tat | ccg | ttt | 720 |
| Ala | Cys | Val | Gly | Gly | Gly | Ser | Asn | Ala | Ala | Gly | Ile | Phe | Tyr | Pro | Phe | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| atc | gat | tct | ggt | gtg | aag | ctg | atc | ggc | gta | gaa | gcc | ggt | ggc | gaa | ggt | 768 |
| Ile | Asp | Ser | Gly | Val | Lys | Leu | Ile | Gly | Val | Glu | Ala | Gly | Gly | Glu | Gly | |
| | | | | 245 | | | | 250 | | | | | 255 | | | |

| | | | | | | | | | | | | | | | | |
|---|---|---|---|---|---|---|---|---|---|---|---|---|---|---|---|---|
| ctg | gaa | acc | ggt | aaa | cat | gcg | gct | tct | ctg | ctg | aaa | ggt | aaa | atc | ggc | 816 |
| Leu | Glu | Thr | Gly | Lys | His | Ala | Ala | Ser | Leu | Leu | Lys | Gly | Lys | Ile | Gly | |
| | | | 260 | | | | | 265 | | | | | 270 | | | |

| | | | | | | | | | | | | | | | | |
|---|---|---|---|---|---|---|---|---|---|---|---|---|---|---|---|---|
| tac | tta | cac | ggt | tct | aag | acg | ttc | gtt | ctg | cag | gat | gac | tgg | ggt | caa | 864 |
| Tyr | Leu | His | Gly | Ser | Lys | Thr | Phe | Val | Leu | Gln | Asp | Asp | Trp | Gly | Gln | |
| | | 275 | | | | | 280 | | | | | 285 | | | | |

| | | | | | | | | | | | | | | | | |
|---|---|---|---|---|---|---|---|---|---|---|---|---|---|---|---|---|
| gtt | cag | gtg | agc | cac | tcc | gtc | tcc | gct | ggc | ctg | gac | tac | tcc | ggt | gtc | 912 |
| Val | Gln | Val | Ser | His | Ser | Val | Ser | Ala | Gly | Leu | Asp | Tyr | Ser | Gly | Val | |
| | 290 | | | | | 295 | | | | | 300 | | | | | |

| | | | | | | | | | | | | | | | | |
|---|---|---|---|---|---|---|---|---|---|---|---|---|---|---|---|---|
| ggt | ccg | gaa | cac | gcc | tat | tgg | cgt | gag | acc | ggt | aaa | gtg | ctg | tac | gat | 960 |
| Gly | Pro | Glu | His | Ala | Tyr | Trp | Arg | Glu | Thr | Gly | Lys | Val | Leu | Tyr | Asp | |
| 305 | | | | 310 | | | | | 315 | | | | | 320 | | |

| | | | | | | | | | | | | | | | | |
|---|---|---|---|---|---|---|---|---|---|---|---|---|---|---|---|---|
| gct | gtg | acc | gat | gaa | gaa | gct | ctg | gac | gca | ttc | atc | gaa | ctg | tct | cgc | 1008 |
| Ala | Val | Thr | Asp | Glu | Glu | Ala | Leu | Asp | Ala | Phe | Ile | Glu | Leu | Ser | Arg | |
| | | | 325 | | | | | 330 | | | | | 335 | | | |

| | | | | | | | | | | | | | | | | |
|---|---|---|---|---|---|---|---|---|---|---|---|---|---|---|---|---|
| ctg | gaa | ggc | atc | atc | cca | gcc | ctg | gag | tct | tct | cac | gca | ctg | gct | tat | 1056 |
| Leu | Glu | Gly | Ile | Ile | Pro | Ala | Leu | Glu | Ser | Ser | His | Ala | Leu | Ala | Tyr | |
| | | | | 340 | | | | 345 | | | | | 350 | | | |

| | | | | | | | | | | | | | | | | |
|---|---|---|---|---|---|---|---|---|---|---|---|---|---|---|---|---|
| ctg | aag | aag | atc | aac | atc | aag | ggt | aaa | gtt | gtg | gtt | aat | ctg | tct | | 1104 |
| Leu | Lys | Lys | Ile | Asn | Ile | Lys | Gly | Lys | Val | Val | Val | Asn | Leu | Ser | | |
| | | 355 | | | | | 360 | | | | | 365 | | | | |

| | | | | | | | | | | | | | | | | |
|---|---|---|---|---|---|---|---|---|---|---|---|---|---|---|---|---|
| ggt | cgt | ggt | gac | aag | gat | ctg | gaa | tct | gta | ctg | aac | cac | ccg | tat | gtt | 1152 |
| Gly | Arg | Gly | Asp | Lys | Asp | Leu | Glu | Ser | Val | Leu | Asn | His | Pro | Tyr | Val | |
| | | 370 | | | | | 375 | | | | | 380 | | | | |

-continued

```
cgc gaa cgc atc cgc ctc gag cac cac cac cac cac tga         1194
Arg Glu Arg Ile Arg Leu Glu His His His His His His
385                 390                 395
```

<210> SEQ ID NO 38
<211> LENGTH: 397
<212> TYPE: PRT
<213> ORGANISM: Artificial Sequence
<220> FEATURE:
<223> OTHER INFORMATION: Synthetic Construct

<400> SEQUENCE: 38

```
Met Lys Gly Tyr Phe Gly Pro Tyr Gly Gln Tyr Val Pro Glu Ile
1               5                   10                  15

Leu Met Pro Ala Leu Glu Glu Leu Glu Ala Ala Tyr Glu Glu Ile Met
            20                  25                  30

Lys Asp Glu Ser Phe Trp Lys Glu Phe Asn Asp Leu Leu Arg Asp Tyr
                35                  40                  45

Ala Gly Arg Pro Thr Pro Leu Tyr Phe Ala Arg Arg Leu Ser Glu Lys
            50                  55                  60

Tyr Gly Ala Arg Val Tyr Leu Lys Arg Glu Asp Leu Leu His Thr Gly
65                  70                  75                  80

Ala His Lys Ile Asn Asn Ala Ile Gly Gln Val Leu Leu Ala Lys Lys
                85                  90                  95

Met Gly Lys Thr Arg Ile Ile Ala Glu Thr Gly Ala Gly Gln His Gly
            100                 105                 110

Val Ala Thr Ala Thr Ala Ala Ala Leu Phe Gly Met Glu Cys Val Ile
        115                 120                 125

Tyr Met Gly Glu Glu Asp Thr Ile Arg Gln Lys Pro Asn Val Glu Arg
    130                 135                 140

Met Lys Leu Leu Gly Ala Lys Val Val Pro Val Lys Ser Gly Ser Arg
145                 150                 155                 160

Thr Leu Lys Asp Ala Ile Asn Glu Ala Leu Arg Asp Trp Ile Thr Asn
                165                 170                 175

Leu Gln Thr Thr Tyr Tyr Val Ile Gly Ser Val Val Gly Pro His Pro
            180                 185                 190

Tyr Pro Ile Ile Val Arg Asn Phe Gln Lys Val Ile Gly Glu Glu Thr
        195                 200                 205

Lys Lys Gln Ile Leu Glu Lys Glu Gly Arg Leu Pro Asp Tyr Ile Val
    210                 215                 220

Ala Cys Val Gly Gly Gly Ser Asn Ala Ala Gly Ile Phe Tyr Pro Phe
225                 230                 235                 240

Ile Asp Ser Gly Val Lys Leu Ile Gly Val Glu Ala Gly Gly Glu Gly
                245                 250                 255

Leu Glu Thr Gly Lys His Ala Ala Ser Leu Leu Lys Gly Lys Ile Gly
            260                 265                 270

Tyr Leu His Gly Ser Lys Thr Phe Val Leu Gln Asp Asp Trp Gly Gln
        275                 280                 285

Val Gln Val Ser His Ser Val Ser Ala Gly Leu Asp Tyr Ser Gly Val
    290                 295                 300

Gly Pro Glu His Ala Tyr Trp Arg Glu Thr Gly Lys Val Leu Tyr Asp
305                 310                 315                 320

Ala Val Thr Asp Glu Glu Ala Leu Asp Ala Phe Ile Glu Leu Ser Arg
                325                 330                 335

Leu Glu Gly Ile Ile Pro Ala Leu Glu Ser Ser His Ala Leu Ala Tyr
```

```
                    340                 345                 350
Leu Lys Lys Ile Asn Ile Lys Gly Lys Val Val Val Asn Leu Ser
            355                 360                 365

Gly Arg Gly Asp Lys Asp Leu Glu Ser Val Leu Asn His Pro Tyr Val
370                 375                 380

Arg Glu Arg Ile Arg Leu Glu His His His His His His
385                 390                 395

<210> SEQ ID NO 39
<211> LENGTH: 1218
<212> TYPE: DNA
<213> ORGANISM: Artificial Sequence
<220> FEATURE:
<223> OTHER INFORMATION: EcTrpBM149TN171D
<220> FEATURE:
<221> NAME/KEY: CDS
<222> LOCATION: (1)..(1218)

<400> SEQUENCE: 39 atg act act ctg ctg aac ccg tac ttc ggt gag ttc ggt ggt atg tac      48
Met Thr Thr Leu Leu Asn Pro Tyr Phe Gly Glu Phe Gly Gly Met Tyr
1               5                   10                  15 gtg cca cag atc ctg atg cct gcg ctg cgc cag ctg gag gag gcg ttt      96
Val Pro Gln Ile Leu Met Pro Ala Leu Arg Gln Leu Glu Glu Ala Phe
            20                  25                  30 gtt agc gcc cag aaa gat ccg gag ttc cag gct cag ttc aac gac ctg     144
Val Ser Ala Gln Lys Asp Pro Glu Phe Gln Ala Gln Phe Asn Asp Leu
        35                  40                  45 ctg aaa aac tat gct ggt cgt ccg acc gcg ctg acg aaa tgc cag aac     192
Leu Lys Asn Tyr Ala Gly Arg Pro Thr Ala Leu Thr Lys Cys Gln Asn
    50                  55                  60 atc act gct ggt acg aac acc acc ctg tac ctg aag cgt gag gac ctg     240
Ile Thr Ala Gly Thr Asn Thr Thr Leu Tyr Leu Lys Arg Glu Asp Leu
65                  70                  75                  80 ctg cat ggt ggt gcg cac aaa acc aac cag gtc ctg ggt caa gca ctg     288
Leu His Gly Gly Ala His Lys Thr Asn Gln Val Leu Gly Gln Ala Leu
                85                  90                  95 ctg gca aaa cgt atg ggc aaa act gaa att att gcg gaa acg ggt gca     336
Leu Ala Lys Arg Met Gly Lys Thr Glu Ile Ile Ala Glu Thr Gly Ala
            100                 105                 110 ggt cag cac ggt gta gct tct gcg ctg gcc agc gca ctg ctg ggt ctg     384
Gly Gln His Gly Val Ala Ser Ala Leu Ala Ser Ala Leu Leu Gly Leu
        115                 120                 125 aag tgt cgt atc tat atg ggt gcg aaa gat gtg gag cgt cag tct ccg     432
Lys Cys Arg Ile Tyr Met Gly Ala Lys Asp Val Glu Arg Gln Ser Pro
    130                 135                 140 aac gta ttc cgc aca cgt ctg atg ggt gca gaa gtg atc ccg gta cac     480
Asn Val Phe Arg Thr Arg Leu Met Gly Ala Glu Val Ile Pro Val His
145                 150                 155                 160 tct ggt tcc gca act ctg aaa gac gca tgt gac gaa gca ctg cgt gac     528
Ser Gly Ser Ala Thr Leu Lys Asp Ala Cys Asp Glu Ala Leu Arg Asp
                165                 170                 175 tgg tcc ggt tct tat gaa act gct cac tac atg ctg ggc acc gca gct     576
Trp Ser Gly Ser Tyr Glu Thr Ala His Tyr Met Leu Gly Thr Ala Ala
            180                 185                 190 ggt cct cac ccg tac ccg acc atc gta cgt gaa ttc cag cgc atg att     624
Gly Pro His Pro Tyr Pro Thr Ile Val Arg Glu Phe Gln Arg Met Ile
        195                 200                 205 ggt gaa gaa acc aaa gcg cag atc ctg gaa cgt gaa ggt cgc ctg cca     672
Gly Glu Glu Thr Lys Ala Gln Ile Leu Glu Arg Glu Gly Arg Leu Pro
    210                 215                 220
```

```
gat gcg gtg atc gcg tgc gta ggt ggt ggt tcc aac gcg atc ggt atg    720
Asp Ala Val Ile Ala Cys Val Gly Gly Gly Ser Asn Ala Ile Gly Met
225                 230                 235                 240 ttc gct gat ttc atc aac gaa acc aac gtt ggc ctg att ggt gta gaa    768
Phe Ala Asp Phe Ile Asn Glu Thr Asn Val Gly Leu Ile Gly Val Glu
                245                 250                 255 cca ggt ggc cac ggt att gaa act ggc gag cac ggt gca cct ctg aaa    816
Pro Gly Gly His Gly Ile Glu Thr Gly Glu His Gly Ala Pro Leu Lys
            260                 265                 270 cac ggt cgc gta ggc att tac ttc ggt atg aaa gct ccg atg atg cag    864
His Gly Arg Val Gly Ile Tyr Phe Gly Met Lys Ala Pro Met Met Gln
        275                 280                 285 act gaa gac ggt cag atc gaa gaa tct tac tcc att tct gca ggt ctg    912
Thr Glu Asp Gly Gln Ile Glu Glu Ser Tyr Ser Ile Ser Ala Gly Leu
    290                 295                 300 gac ttc ccg tct gtt ggt ccg caa cac gca tat ctg aac tct acc ggt    960
Asp Phe Pro Ser Val Gly Pro Gln His Ala Tyr Leu Asn Ser Thr Gly
305                 310                 315                 320 cgt gcg gac tac gtg tct atc act gac gac gag gct ctg gag gcc ttt   1008
Arg Ala Asp Tyr Val Ser Ile Thr Asp Asp Glu Ala Leu Glu Ala Phe
                325                 330                 335 aaa act ctg tgc ctg cac gaa ggt atc att cca gct ctg gaa tcc agc   1056
Lys Thr Leu Cys Leu His Glu Gly Ile Ile Pro Ala Leu Glu Ser Ser
            340                 345                 350 cac gca ctg gca cac gca ctg aaa atg atg cgt gaa aac cca gac aaa   1104
His Ala Leu Ala His Ala Leu Lys Met Met Arg Glu Asn Pro Asp Lys
        355                 360                 365 gaa cag ctg ctg gtg gtt aac ctg agc ggt cgt ggt gac aag gat atc   1152
Glu Gln Leu Leu Val Val Asn Leu Ser Gly Arg Gly Asp Lys Asp Ile
    370                 375                 380 ttc acg gtt cac gac atc ctg aag gct cgt ggt gaa atc ctc gag cac   1200
Phe Thr Val His Asp Ile Leu Lys Ala Arg Gly Glu Ile Leu Glu His
385                 390                 395                 400 cac cac cac cac cac tga                                            1218
His His His His His
                405

<210> SEQ ID NO 40
<211> LENGTH: 405
<212> TYPE: PRT
<213> ORGANISM: Artificial Sequence
<220> FEATURE:
<223> OTHER INFORMATION: Synthetic Construct

<400> SEQUENCE: 40

Met Thr Thr Leu Leu Asn Pro Tyr Phe Gly Glu Phe Gly Gly Met Tyr
1               5                   10                  15

Val Pro Gln Ile Leu Met Pro Ala Leu Arg Gln Leu Glu Glu Ala Phe
            20                  25                  30

Val Ser Ala Gln Lys Asp Pro Glu Phe Gln Ala Gln Phe Asn Asp Leu
        35                  40                  45

Leu Lys Asn Tyr Ala Gly Arg Pro Thr Ala Leu Thr Lys Cys Gln Asn
    50                  55                  60

Ile Thr Ala Gly Thr Asn Thr Thr Leu Tyr Leu Lys Arg Glu Asp Leu
65                  70                  75                  80

Leu His Gly Gly Ala His Lys Thr Asn Gln Val Leu Gly Gln Ala Leu
                85                  90                  95

Leu Ala Lys Arg Met Gly Lys Thr Glu Ile Ile Ala Glu Thr Gly Ala
            100                 105                 110
```

```
Gly Gln His Gly Val Ala Ser Ala Leu Ala Ser Ala Leu Leu Gly Leu
        115                 120                 125

Lys Cys Arg Ile Tyr Met Gly Ala Lys Asp Val Glu Arg Gln Ser Pro
        130                 135                 140

Asn Val Phe Arg Thr Arg Leu Met Gly Ala Glu Val Ile Pro Val His
145                 150                 155                 160

Ser Gly Ser Ala Thr Leu Lys Asp Ala Cys Asp Glu Ala Leu Arg Asp
                165                 170                 175

Trp Ser Gly Ser Tyr Glu Thr Ala His Tyr Met Leu Gly Thr Ala Ala
                180                 185                 190

Gly Pro His Pro Tyr Pro Thr Ile Val Arg Glu Phe Gln Arg Met Ile
            195                 200                 205

Gly Glu Glu Thr Lys Ala Gln Ile Leu Glu Arg Gly Arg Leu Pro
        210                 215                 220

Asp Ala Val Ile Ala Cys Val Gly Gly Gly Ser Asn Ala Ile Gly Met
225                 230                 235                 240

Phe Ala Asp Phe Ile Asn Glu Thr Asn Val Gly Leu Ile Gly Val Glu
                245                 250                 255

Pro Gly Gly His Gly Ile Glu Thr Gly Glu His Gly Ala Pro Leu Lys
                260                 265                 270

His Gly Arg Val Gly Ile Tyr Phe Gly Met Lys Ala Pro Met Met Gln
            275                 280                 285

Thr Glu Asp Gly Gln Ile Glu Glu Ser Tyr Ser Ile Ser Ala Gly Leu
        290                 295                 300

Asp Phe Pro Ser Val Gly Pro Gln His Ala Tyr Leu Asn Ser Thr Gly
305                 310                 315                 320

Arg Ala Asp Tyr Val Ser Ile Thr Asp Asp Glu Ala Leu Glu Ala Phe
                325                 330                 335

Lys Thr Leu Cys Leu His Glu Gly Ile Ile Pro Ala Leu Glu Ser Ser
                340                 345                 350

His Ala Leu Ala His Ala Leu Lys Met Met Arg Glu Asn Pro Asp Lys
                355                 360                 365

Glu Gln Leu Leu Val Val Asn Leu Ser Gly Arg Gly Asp Lys Asp Ile
        370                 375                 380

Phe Thr Val His Asp Ile Leu Lys Ala Arg Gly Glu Ile Leu Glu His
385                 390                 395                 400

His His His His
            405
```